(12) United States Patent
Ramkissoon et al.

(10) Patent No.: US 12,285,407 B2
(45) Date of Patent: Apr. 29, 2025

(54) BIS-INDOLYLMETHANE DERIVATIVES AND USES THEREOF

(71) Applicant: The University of The West Indies, St. Augustine (TT)

(72) Inventors: Antonio Ramkissoon, Princes Town (TT); Adash Ramsubhag, St. Augustine (TT); Anderson Maxwell, Tacarigua (TT); Jayaraj Jayaraman, St. Augustine (TT)

(73) Assignee: The University of The West Indies, St. Augustine (TT)

( * ) Notice: Subject to any disclaimer, the term of this patent is extended or adjusted under 35 U.S.C. 154(b) by 832 days.

(21) Appl. No.: 17/294,819

(22) PCT Filed: Nov. 19, 2019

(86) PCT No.: PCT/IB2019/001221
§ 371 (c)(1),
(2) Date: May 18, 2021

(87) PCT Pub. No.: WO2020/104842
PCT Pub. Date: May 28, 2020

(65) Prior Publication Data
US 2021/0401803 A1 Dec. 30, 2021

Related U.S. Application Data

(60) Provisional application No. 62/770,359, filed on Nov. 21, 2018.

(51) Int. Cl.
*A61K 31/4045* (2006.01)
*A61K 45/06* (2006.01)
*A61P 31/04* (2006.01)

(52) U.S. Cl.
CPC .......... *A61K 31/4045* (2013.01); *A61K 45/06* (2013.01); *A61P 31/04* (2018.01)

(58) Field of Classification Search
CPC .............. A61K 31/4045; A61K 31/165; A61K 31/198; A61K 31/343; A61K 45/06; A61K 2300/00; A61P 31/04
See application file for complete search history.

(56) References Cited

U.S. PATENT DOCUMENTS

| 8,580,843 B2 | 11/2013 | Tjalkens et al. |
| 2010/0087504 A1 | 4/2010 | Tjalkens |
| 2016/0037773 A1 | 2/2016 | Qian et al. |

FOREIGN PATENT DOCUMENTS

| WO | WO-99/00381 A1 | 1/1999 |
| WO | WO-2017/161374 A1 | 9/2017 |
| WO | WO-2018/107201 A1 | 6/2018 |

OTHER PUBLICATIONS

Dong et al., "Small molecule mimics of DFTamP1, a database designed anti-Staphylococcal peptide," Bioorganic & Medicinal Chemistry (2017), available online Nov. 30, 2016, vol. 25, pp. 864-869.

(Continued)

*Primary Examiner* — Kortney L. Klinkel
*Assistant Examiner* — Padmaja S Rao
(74) *Attorney, Agent, or Firm* — Wilmer Cutler Pickering Hale and Dorr LLP

(57) ABSTRACT

A pharmaceutical composition is described herein, including an antimicrobial agent and a compound having Formula A, or Formula B. Methods of using the pharmaceutical compositions to treat microbial infection are also described.

(Continued)

A: Untreated
B: Amp only
C: Amp + 5 mg SP-BIM 13
D: Amp + 10 mg SP-BIM 13
E: Amp + 25 mg SP-BIM 13
F: Van only
G: Van + 5 mg SP-BIM 13
H: Van + 10 mg SP-BIM 13
I: Van + 25 mg SP-BIM 13
J: 5 mg SP-BIM 13 only
K: 10 mg SP-BIM 13 only

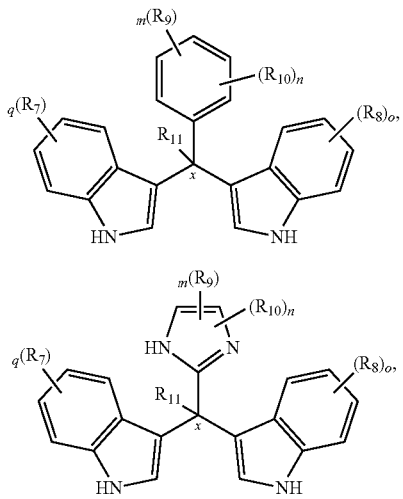

A

B

11 Claims, 53 Drawing Sheets

(56) References Cited

OTHER PUBLICATIONS

Exteded European Search Report mailed Jun. 27, 2022, in the European patent application No. 19887383.8. 13 pages.
Mandal et al., "Novel boronic acid derivatives of bis(indolyl) methane as anti-MRSA agents," Bioorganic & Medicinal Chemistry Letters, available online Mar. 25, 2017, vol. 27, pp. 2135-2138.
Nair et al., "Marine Bacteria, XLVII—Psychrotolerant Bacteria from Extreme Antarctic Habitats as Producers of Rare Bis- and Trisindole Alkaloids," Planta Medica, Jun. 2016, vol. 82(6). 9 pages.
Sarva et al., "Synthesis, antibacterial and anti-inflammatory activity of bis(indolyl)methanes," Chinese Chemical Letters (2016), available online Aug. 24, 2015, vol. 27, pp. 16-20.
Sharma et al., "A new class of bactericidal agents against *S. aureus*, MRSA and VRE derived from bisindolylmethane," Medical Chemistry Research, vol. 23, p. 1643-1653.
Andrews, "Determination of minimum inhibitory concentrations," Journal of Antimicrobial Chemotherapy, Jul. 2001, vol. 48, pp. 5-16.
Berge et al., "Pharmaceutical Salts," Journal of Pharmaceutical Sciences, Jan. 1977, vol. 66, No. 1; pp. 1-19.
Buerge et al., "Handling and Restraint" Chapter 31 in The Laboratory Mouse, Academic Press, Elsevier, Nov. 11, 2004, pp. 517-526.
CLSI document M100-S24, "Performance Standards for Antimicrobial Susceptibility Testing; Twenty-Fourth Informational Supplement" Clinical and Laboratory Standards Institute (CLSI), Wayne, PA: CLSI; Jan. 2014, vol. 34, No. 1. 230 pages.
Deb et al. "An Efficient and Clean Synthesis of Bis(indolyl)methanes in a Protic Solvent at Room Temperature," Tetrahedron Letters, Feb. 27, 2006, vol. 47(9), pp. 1441-1443.
Herold et al, "Ciprofloxacin induces apoptosis and inhibits proliferation of human colorectal carcinoma cells," British Journal of Cancer, Feb. 2022, vol. 86(3), pp. 443-448.
Hirashita, "Condensation of indoles and aldehydes in subcritical water without the addition of catalysts." Bulletin of the Chemical Society of Japan, Sep. 25, 2015, vol. 88(12), pp. 1760-1764.
Imran et al., "Synthesis of novel bisindolylmethane Schiff bases and their antibacterial activity," Molecules, Aug. 6, 2014, vol. 19(8), pp. 11722-11740.
International Search Report and Written Opinion mailed Mar. 9, 2020, in the International Application No. PCT/IB19/01221. 14 pages.
Jassim and Al-Ibadi, "Ampicillin inhibition effect on HCT116 cell line" ResarchGate, Mar. 25, 2017. 7 pages. Retrieved from (https://www.researchgate.net/publication/315619261_Ampicillin_inhibition_effect_on_HCT116_cell_line).
Khodaverdian et al., "Discovery of Antivirulence Agents Against Methicillin-Resistant *Staphylococcus aureus*," Antimicrobial Agents and Chemotherapy, Aug. 2013, vol. 57(8), pp. 3645-3652.
Morrison et al., "The staphylococcal accessory regulator, SarA, is an RNA-binding protein that modulates the mRNA turnover properties of late-exponential and stationary phase *Staphylococcus aureus* cells," Frontiers in Cellular and Infection Microbiology, Mar. 8, 2012, vol. 2(26), pp. 1-11.
Multhoff et al., "Chronic inflammation in cancer development," Frontiers in Immunology, Jan. 12, 2012, vol. 2(98), pp. 1-17.
O'Toole, "Microtiter Dish Biofilm Formation Assay," Journal of Visualized Experiments, Jan. 30, 2011, 47(2437), pp. 1-2.
Velikova et al., "Walk, the Path towards New Antibacterials with Low Potential for Resistance Development," ACS Medicinal Chemistry Letters, Sep. 18, 2013, vol. 4, pp. 891-894.
Wauford, "Hemolysis assay," Portocols.io. Sep. 28, 2016, accessed Feb. 2, 2019. 2 pages.
Wright, "Antibiotic Adjuvants: Rescuing Antibiotics from Resistance," Trends in Microbiology, Nov. 2016, vol. 24, pp. 862-871.
Zheng et al., "The Essential Walk Histidine Kinase and WalR Regulator Differentially Mediate Autolysis of *Staphylococcus aureus* RN4220," J. Nat. Sci. Jun. 2015, 1(6). Author manuscript, pp. 1-14.

SP-BIM 21
CD₃OD
13C

A: Untreated
B: Amp only
C: Amp + 5 mg SP-BIM 13
D: Amp + 10 mg SP-BIM 13
E: Amp + 25 mg SP-BIM 13
F: Van only
G: Van + 5 mg SP-BIM 13
H: Van + 10 mg SP-BIM 13
I: Van + 25 mg SP-BIM 13
J: 5 mg SP-BIM 13 only
K: 10 mg SP-BIM 13 only A: Untreated
B: Amp only (125 mg/kg)
C: Amp (125 mg/kg) + SP-BIM 9 (5 mg/kg)
D: Amp (125 mg/kg) + SP-BIM 9 (10 mg/kg)
E: SP-BIM 9 only (5 mg/kg)
F: SP-BIM 9 only (10 mg/kg)

FIG. 14

'X' = mg/kg; Rep = replicate. Experiments were repeated twice and results given separately as Replicates 1 and 2.

Experiments were repeated twice and results given separately as Replicates 1 and 2.

NA: No antibiotic, SC: Sterile control, NC: No SP-BIM

BIS-INDOLYLMETHANE DERIVATIVES AND USES THEREOF

CROSS-REFERENCE TO RELATED APPLICATIONS

This application is a National Stage Entry of PCT International Application No. PCT/IB2019/001221, filed on Nov. 19, 2019, which claims priority to U.S. Provisional Patent Application No. 62/770,359, filed on Nov. 21, 2018, the contents of each of which are hereby incorporated by reference in their entireties.

INCORPORATION BY REFERENCE

All patents, patent applications, and publications cited herein are hereby incorporated by reference in their entirety in order to more fully describe the state of the art as known to those skilled therein as of the date of the invention described herein.

FIELD OF THE INVENTION

This invention generally relates to compounds and pharmaceutical compositions.

BACKGROUND

There is a need to develop new antibiotics but also to develop new strategies to deal with antibiotic resistance. The problem with antibiotic therapy is that bacteria and other microorganisms will, given time, evolve to become resistant. Large pharmaceutical companies have mostly abandoned antibiotic development because it is both expensive and the investment returns are not as large as those of other chronic illnesses.

Antibiotic adjuvants, also termed "resistance breakers" or "antibiotic potentiators," when co-administered with an antibiotic either block the resistance mechanism of the bacteria or enhance the action of the antibiotic drug. The main antibiotic adjuvants currently marketed are the inhibitors of β-lactamase enzymes produced by drug resistant bacteria to break down β-lactam antibiotics, such as the penicillins. However, there are other resistance mechanisms for β-lactams and other classes of antibiotics for which these adjuvants would have no effect. It seems, then, that even though the idea of antibiotic adjuvants is promising, only a very limited number of these compounds have progressed to clinical applications.

Adjuvants offer an advantage in current antimicrobial therapies as they can either enhance the activity of antibiotics or reduce/block resistance of the pathogen. Antibiotic adjuvants have been broadly classed into three categories: 1A, 1B, and 2. Category 1A adjuvants directly inhibit antibiotic resistance by inactivating enzymes, efflux pump systems, or alternate targets while category 1B adjuvants enhance antibiotic activity by circumventing intrinsic resistance mechanisms, including metabolic pathways or physiology other than direct inhibition of specific resistance elements. Category 2 adjuvants do not directly impact bacteria but rather operate on host properties to potentiate antibiotic action.

SUMMARY

A novel approach for developing antimicrobial agents is to search for new antimicrobial agents and make established antibiotics useful again. One way in which existing antimicrobial agents can become effective against drug resistant pathogens is to develop potentiators that potentiate the antibiotics. Described herein are antimicrobial agents and compounds that potentiate existing antimicrobial agents.

In one aspect, a pharmaceutical composition is disclosed, including an antimicrobial agent and a compound having Formula A or B,

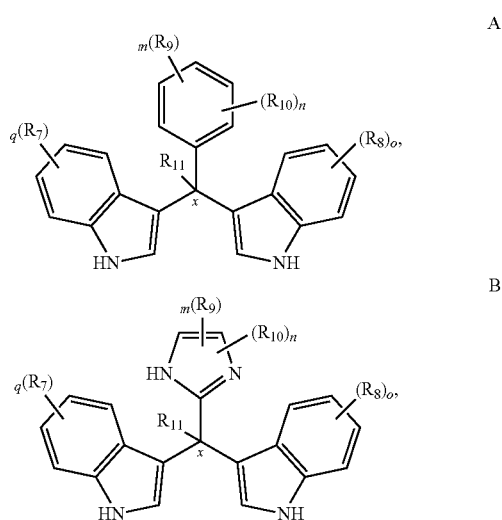

where
each occurrence of $R_9$ is independently selected from the group consisting of $NH_2$, $NO_2$, OH, CHO, halogen, and $C_1$ to $C_6$ alkyl optionally substituted with one or more of halogen, OH, $NH_2$, $NO_2$, or CHO; and where $R_9$ is substituted on the phenyl ring of Formula A or the imidazole ring of Formula B;

m is 0 to 5;

each occurrence of $R_{10}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, $(CH_2)_p$($C_1$ to $C_6$)haloalkyl, or CH(indole)$_2$, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy, or alternatively two $R_{10}$ taken together with the ring atoms they are connected to form a 3-7-membered aromatic ring; where $R_{10}$ is a group substituted on the indole ring and/or the phenyl ring of Formula A or on the indole ring and/or the imidazole ring of Formula B;

each of n, o, p and q is independently an integer from 0 to 4;

$R_7$ and $R_8$ are each independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, or $(CH_2)_p$($C_1$ to $C_6$)haloalkyl, in which said heterocycle contains at least one heteroatom selected from the group consisting of nitrogen, oxygen, and sulfur and may be optionally substituted by from one to three groups which may be the same or different selected from the group consisting of halogen, OH, CN, $(C_1$ to $C_4)$alkyl, $(C_1$ to $C_4)$haloalkyl, and $(C_1$ to $C_4)$alkoxy;

each occurrence of $R_{11}$ is independently H, halogen, OH, CN, $NO_2$, $OCF_3$, $(C_1$ to $C_6)$alkyl, $(C_2$ to $C_6)$alkenyl, $(C_2$ to $C_6)$alkynyl, $(C_1$ to $C_6)$alkoxy, $(C_3$ to $C_7)$cycloalkyl, 3-7-membered heterocycle, $(C_1$ to $C_6)$alkylthio, $NR_aR_b$, $(C_1$ to $C_6)$haloalkyl, $(CH_2)_p(C_3$ to $C_7)$cycloalkyl, $(CH_2)_pOR_a$, $(CH_2)_pSR_a$, or $(CH_2)_pNR_aR_b$, in which said heterocycle includes at least one heteroatom selected from the group consisting of nitrogen, oxygen and sulfur and may be optionally substituted by from one to three groups which may be the same or different selected from the group consisting of halogen, OH, CN, $(C_1$ to $C_4)$alkyl, $(C_1$ to $C_4)$haloalkyl and $(C_1$ to $C_4)$alkoxy;

$R_a$ and $R_b$ are each independently H, $(C_1$ to $C_6)$alkyl, $(C_2$ to $C_6)$alkenyl, or $(C_3$ to $C_7)$cycloalkyl; and x is absent; or alternatively x is a positive charge and $R_{11}$ is absent.

In any one of the embodiments described herein, $R_7$ and $R_8$ are each independently H, halogen, OH, CN, $OCF_3$, $(C_1$ to $C_6)$alkyl, $(C_2$ to $C_6)$alkenyl, $(C_2$ to $C_6)$alkynyl, $(C_1$ to $C_6)$alkoxy, or $(C_3$ to $C_7)$cycloalkyl.

In any one of the embodiments described herein, $R_7$ and $R_8$ are each independently $(C_1$ to $C_6)$alkylthio, $NR_aR_b$, $(C_1$ to $C_6)$haloalkyl, $(CH_2)_p(C_3$ to $C_7)$cycloalkyl, $(CH_2)_pOR_a$, $(CH_2)_pSR_a$, $(CH_2)_pNR_aR_b$, or $(CH_2)_p(C_1$ to $C_6)$haloalkyl.

In any one of the embodiments described herein, $R_7$ and $R_8$ are each independently 3 to 7-membered heterocycle optionally substituted by from one to three groups which may be the same or different selected from the group consisting of halogen, OH, CN, $(C_1$ to $C_4)$alkyl, $(C_1$ to $C_4)$haloalkyl, and $(C_1$ to $C_4)$alkoxy.

In any one of the embodiments described herein, $R_7$ and $R_8$ are each independently $OCH_3$ or $(C_1$ to $C_6)$alkoxy.

In any one of the embodiments described herein, $R_7$ and $R_8$ are each independently H, $(C_1$ to $C_6)$alkyl, $NH_2$, Br, or OH.

In any one of the embodiments described herein, $R_{11}$ is H, halogen, OH, or $(C_1$ to $C_6)$alkyl.

In any one of the embodiments described herein, the compound has the structure of Formula A':

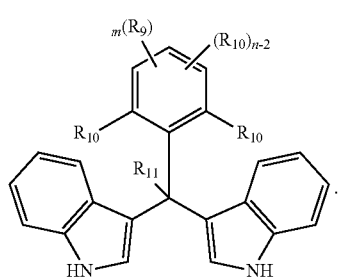

A'

In any one of the embodiments described herein, at least one $R_9$ is selected from the group consisting of $NH_2$, OH, CHO, halogen, and $(C_1$ to $C_6)$alkyl substituted with one or more halogen, $NH_2$, CHO, or OH.

In any one of the embodiments described herein, $R_9$ is independently selected from the group consisting of halogen, $CH_3$, OH, $NH_2$, $NO_2$, CHO, and $C(CH_3)_3$.

In any one of the embodiments described herein, at least one $R_9$ is halogen.

In any one of the embodiments described herein, at least one $R_9$ is F, Cl, or Br.

In any one of the embodiments described herein, at least one $R_9$ is $NH_2$ or $(C_1$ to $C_6)$alkyl substituted with one or more $NH_2$.

In any one of the embodiments described herein, at least one $R_9$ is CHO or $(C_1$ to $C_6)$alkyl substituted with one or more CHO.

In any one of the embodiments described herein, at least one $R_9$ is OH or $(C_1$ to $C_6)$alkyl substituted with one or more OH.

In any one of the embodiments described herein, each occurrence of $R_{10}$ is independently H, halogen, OH, CN, $OCF_3$, $(C_1$ to $C_6)$alkyl, $(C_2$ to $C_6)$alkenyl, $(C_2$ to $C_6)$alkynyl, $(C_1$ to $C_6)$alkoxy, or $(C_3$ to $C_7)$cycloalkyl.

In any one of the embodiments described herein, each occurrence of $R_{10}$ is independently 3-7-membered heterocycle, $(C_1$ to $C_6)$alkylthio, $NR_aR_b$, $(C_1$ to $C_6)$haloalkyl, $(CH_2)_p(C_3$ to $C_7)$cycloalkyl, $(CH_2)_pOR_a$, $(CH_2)_pSR_a$, $(CH_2)_pNR_aR_b$, or $(CH_2)_p(C_1$ to $C_6)$haloalkyl.

In any one of the embodiments described herein, $R_{10}$ is independently selected from the group consisting of halogen, $CH_3$, $N(CH_3)_2$, $NO_2$, CHO, OH, $OCH_3$, $NH_2$, $C(CH_3)_3$, and

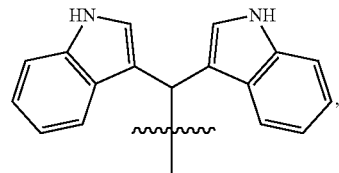 [SMILES: *C(c1c[nH]c2ccccc12)c1c[nH]c2ccccc12]

or where two $R_{10}$ taken together form a 6-membered aromatic ring.

In any one of the embodiments described herein, o and q are each independently 0, 1, or 2.

In any one of the embodiments described herein, o and q are 0.

In any one of the embodiments described herein, m is 1, 2, or 3.

In any one of the embodiments described herein, n is 1 or 2.

In any one of the embodiments described herein, n is 3 or 4.

In any one of the embodiments described herein, n is 0.

In any one of the embodiments described herein, the compound is selected from the compounds in Table 1 or Table 2.

In any one of the embodiments described herein, the compound is

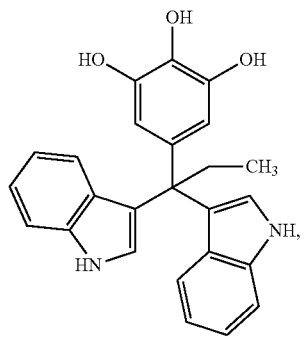

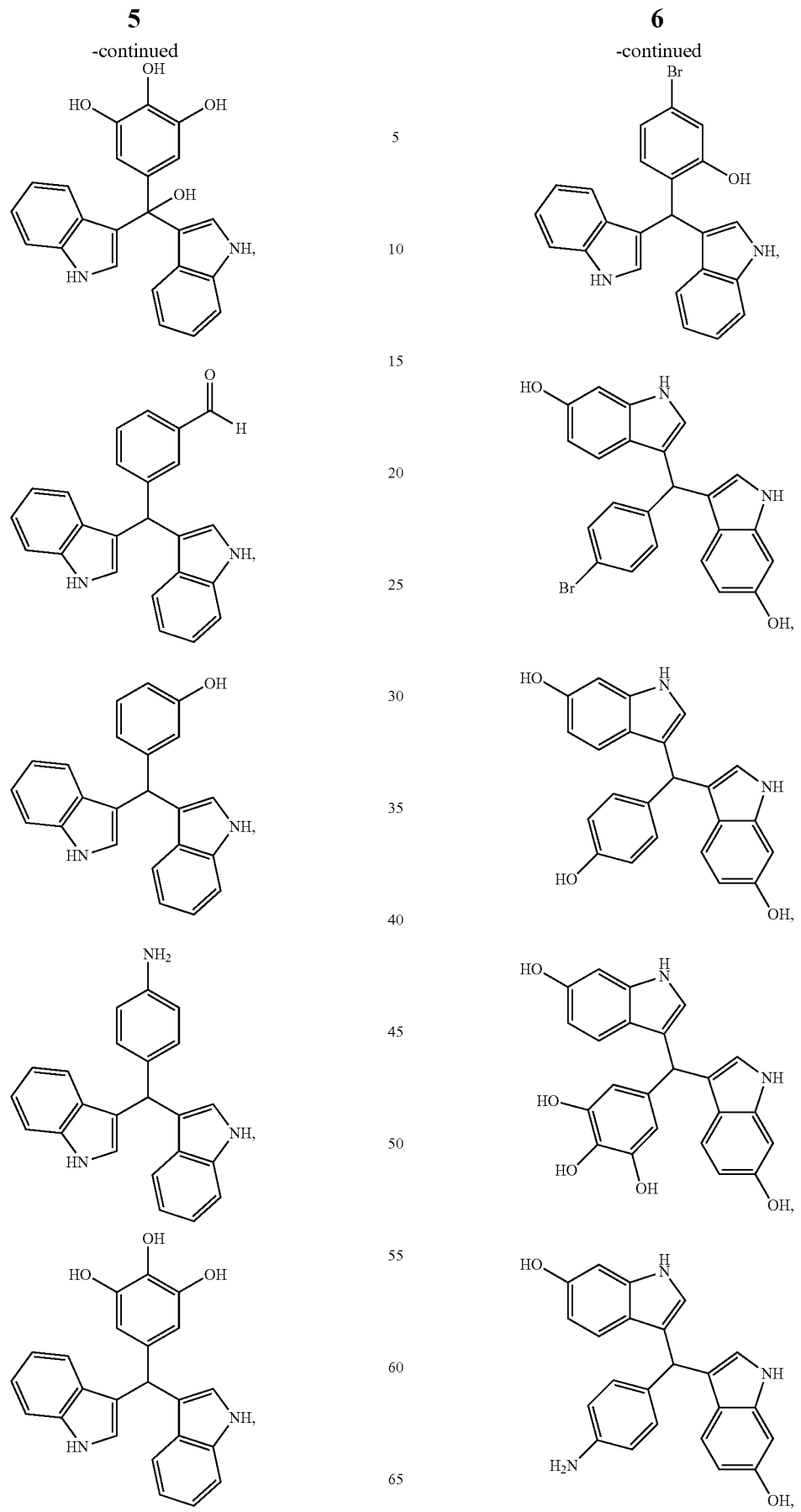

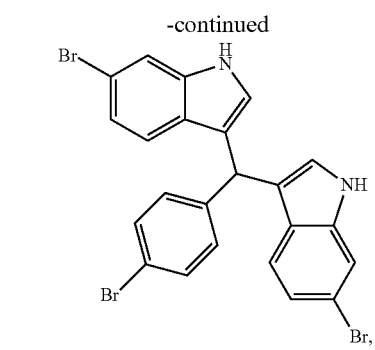
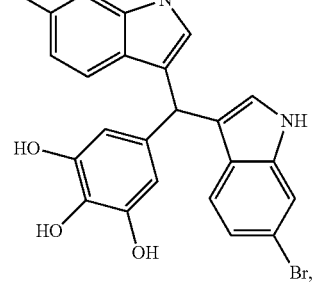
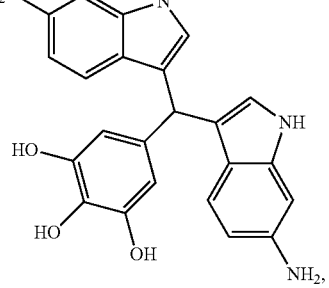
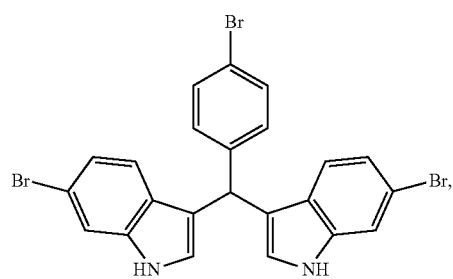
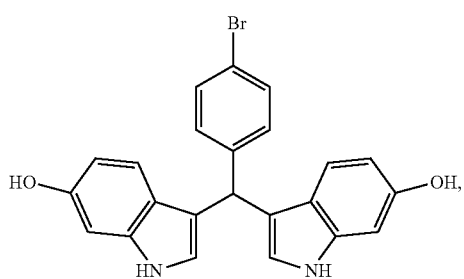
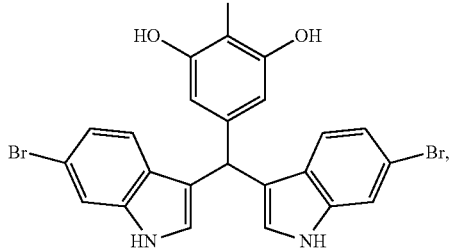
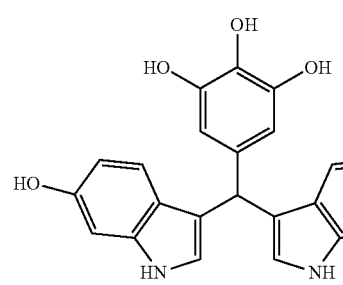
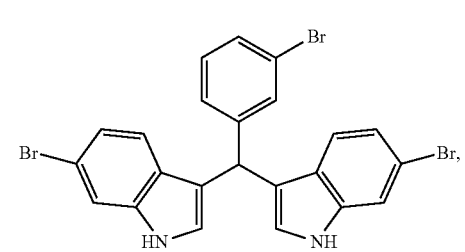
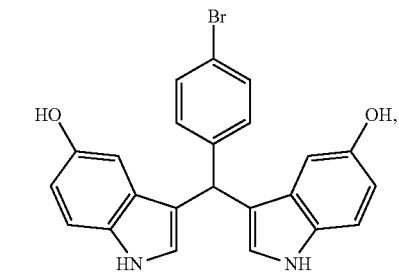
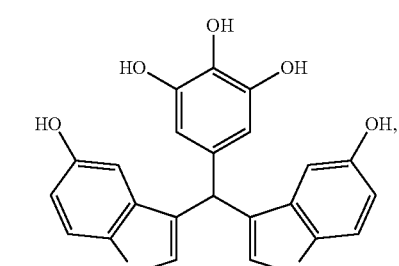
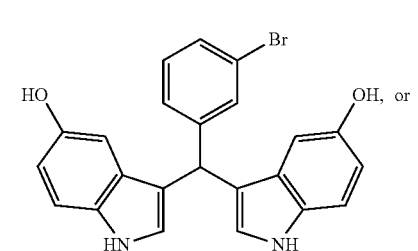

In any one of the embodiments described herein, the compound is

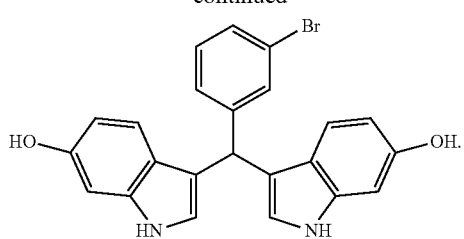

In any one of the embodiments described herein, the antimicrobial agent is an antibacterial agent.

In any one of the embodiments described herein, the antimicrobial agent is an antifungal agent.

In any one of the embodiments described herein, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In any one of the embodiments described herein, the antimicrobial agent is selected from the group consisting of ampicillin, imipenem, cephalexin, erythromycin, aztreonam, trimethoprim, streptomycin, ciprofloxacin, vancomycin, doxycycline, chloramphenicol, and kanamycin.

In any one of the embodiments described herein, the compound is

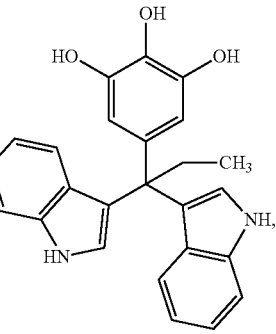

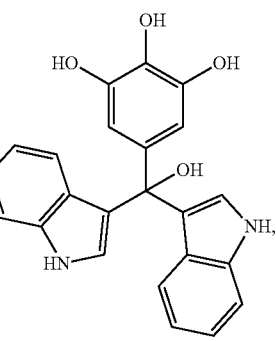

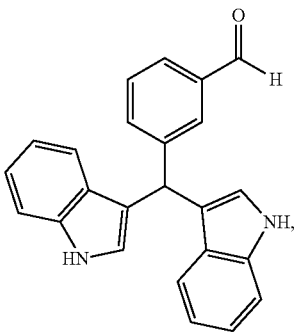

-continued

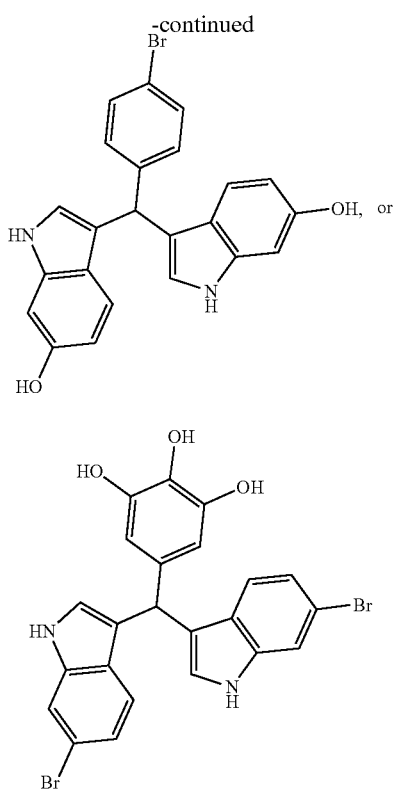

and the antimicrobial agent is selected from the group consisting of ampicillin, imipenem, cephalexin, erythromycin, streptomycin, vancomycin, doxycycline, and kanamycin.

In any one of the embodiments described herein, the compound is

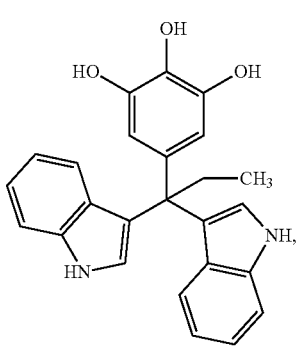

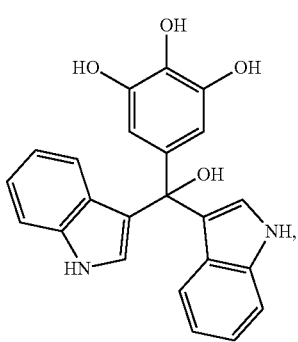

-continued

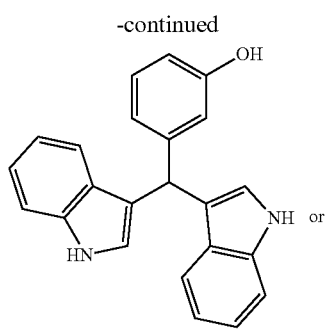

and the antimicrobial agent is selected from the group consisting of ampicillin, imipenem, cephalexin, aztreonam, trimethoprim, streptomycin, ciprofloxacin, vancomycin, doxycycline, and kanamycin.

In any one of the embodiments described herein, the compound is

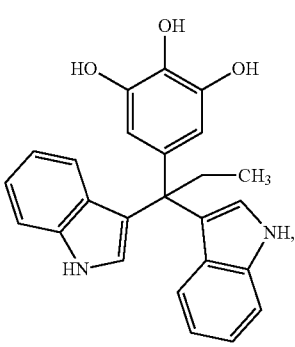

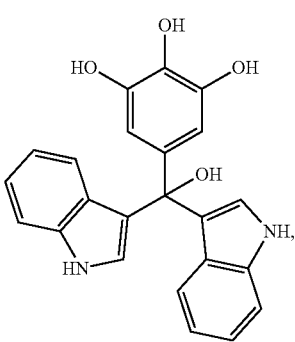

-continued

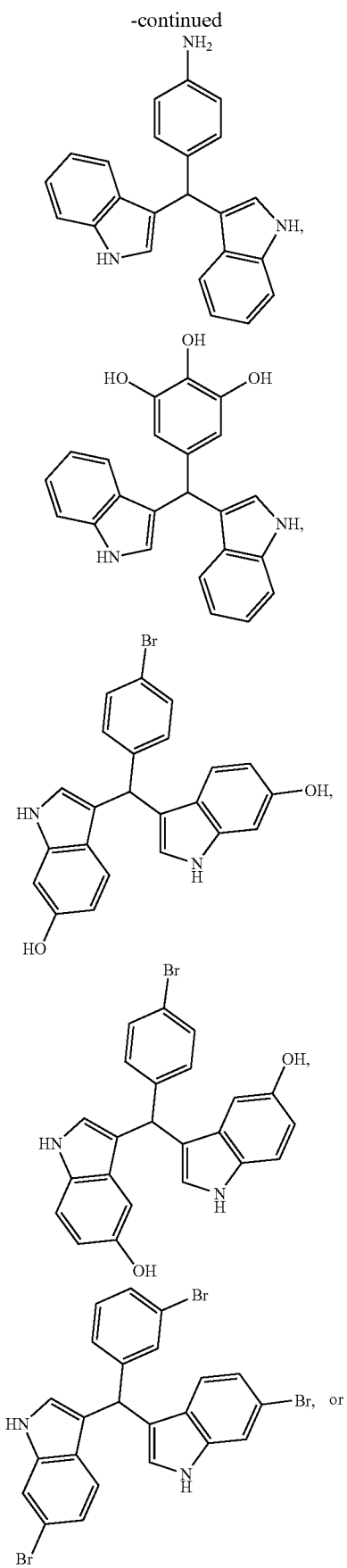

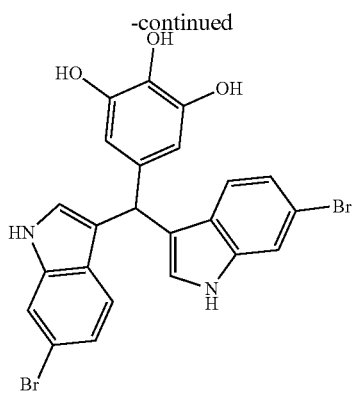

and the antimicrobial agent is selected from the group consisting of ampicillin, imipenem, cephalexin, erythromycin, aztreonam, trimethoprim, streptomycin, ciprofloxacin, vancomycin, doxycycline, chloramphenicol, and kanamycin.

In any one of the embodiments described herein, the pharmaceutical composition further includes one or more pharmaceutically acceptable excipients.

In another aspect, a method of treating, preventing, or reducing the risk of a microbial infection in a patient is disclosed, including administering to the patient a pharmaceutical composition according to any one of the embodiments described herein.

In any one of the embodiments described herein, the microbial infection is a bacterial infection.

In any one of the embodiments described herein, the method includes treating, preventing, or reducing the risk of biofilms, hemotoxicity, and/or virulence.

In any one of the embodiments described herein, the administration is performed once daily.

In any one of the embodiments described herein, the microbial infection is clinically antibiotic resistant.

In any one of the embodiments described herein, the activity of the antimicrobial agent is potentiated by the compound.

In any one of the embodiments described herein, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In any one of the embodiments described herein, the antimicrobial agent is selected from the group consisting of erythromycin, trimethoprim, ciprofloxacin, streptomycin, aztreonam, cefalexin, vancomycin, ampicillin, doxycycline, and kanamycin.

In any one of the embodiments described herein, the antimicrobial agent is vancomycin or ampicillin.

In any one of the embodiments described herein, the microbe is Gram-positive bacteria, Gram-negative bacteria, or a mixture thereof.

In any one of the embodiments described herein, the microbe is selected from the group consisting of *Bacillus cereus, Streptococcus pyogenes, Streptococcus pneumoniae, Staphylococcus aureus, Enterococcus faecium, Corynebacterium diphtheriae, Escherichia coli, Salmonella typhimurium, Pseudomonas aeruginosa, Klebsiella pneumoniae, Candida albicans*, and mixtures thereof.

In any one of the embodiments described herein, the microbe is *Staphylococcus aureus, Enterococcus faecium*, or a mixture thereof.

In any one of the embodiments described herein, the microbe is methicillin-resistant *Staphylococcus aureus* (MRSA).

In any one of the embodiments described herein, the patient is a domestic animal.

In any one of the embodiments described herein, the patient is a mammal.

In any one of the embodiments described herein, the patient is a human.

In yet another aspect, a method of inhibiting or extinguishing the growth of one or more microbial cultures in vitro is disclosed, including administering to the microbial culture a pharmaceutical composition according to any one of the embodiments described herein.

In any one of the embodiments described herein, the microbial culture includes a bacterial culture.

In any one of the embodiments described herein, the microbial culture includes biofilms.

In any one of the embodiments described herein, the microbial culture includes microbes that are clinically antibiotic resistant.

In any one of the embodiments described herein, the microbial culture includes *Staphylococcus aureus*.

In yet another aspect, a method of treating, preventing, or reducing the risk of a bacterial infection in a patient is disclosed, including administering to a patient a compound of Formula A or B,

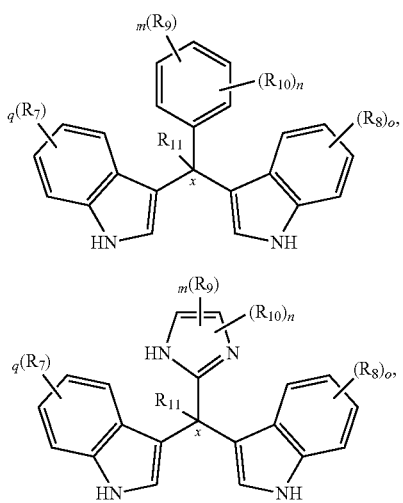

where
each occurrence of $R_9$ is independently selected from the group consisting of $NH_2$, $NO_2$, OH, CHO, halogen, and ($C_1$ to $C_6$)alkyl optionally substituted with one or more of halogen, OH, $NH_2$, $NO_2$, or CHO; and where $R_9$ is substituted on the phenyl ring of Formula A or the imidazole ring of Formula B;
m is 0 to 5;
each occurrence of $R_{10}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p(C_3$ to $C_7$)cycloalkyl, $(CH_2)_pOR_a$, $(CH_2)_pSR_a$, $(CH_2)_pNR_aR_b$, $(CH_2)_p$ ($C_1$ to $C_6$)haloalkyl, or $CH(indole)_2$, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy, or alternatively two $R_{10}$ taken together with the ring atoms they are connected to form a 3-7-membered aromatic ring; where $R_{10}$ is a group substituted on the indole ring and/or the phenyl ring of Formula A or on the indole ring and/or the imidazole ring of Formula B;
each of n, o, p and q is independently an integer from 0 to 4; $R_7$ and $R_8$ are each independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p(C_3$ to $C_7$)cycloalkyl, $(CH_2)_pOR_a$, $(CH_2)_pSR_a$, $(CH_2)_pNR_aR_b$, or $(CH_2)_p$ ($C_1$ to $C_6$)haloalkyl, in which said heterocycle contains at least one heteroatom selected from the group consisting of nitrogen, oxygen, and sulfur and may be optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy;
each occurrence of $R_{11}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p(C_3$ to $C_7$)cycloalkyl, $(CH_2)_pOR_a$, $(CH_2)_pSR_a$, or $(CH_2)_pNR_aR_b$, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy;
$R_a$ and $R_b$ are each independently H, ($C_1$ to $C_6$)alkyl, ($C_2$ to $C_6$)alkenyl, or ($C_3$ to $C_7$)cycloalkyl; and
x is absent; or alternatively x is a positive charge and $R_{11}$ is absent.

In any one of the embodiments described herein, the method includes one or more pharmaceutically acceptable excipients.

Any one of the embodiments disclosed herein may be properly combined with any other embodiment disclosed herein. The combination of any one of the embodiments disclosed herein with any other embodiments disclosed herein is expressly contemplated. Specifically, the selection of one or more embodiments for one substituent group can be properly combined with the selection of one or more particular embodiments for any other substituent group. Such combination can be made in any one or more embodiments of the application described herein or any formula described herein.

DESCRIPTION OF THE DRAWINGS

The invention is described with reference to the following figures, which are presented for the purpose of illustration only and are not intended to be limiting. In the drawings:

FIG. 14 depicts the efficacy of SP-BIM 13 in preventing hemolysin production in *Staphylococcus aureus*, according to one or more embodiments.

DETAILED DESCRIPTION

Definitions

Figure 1:
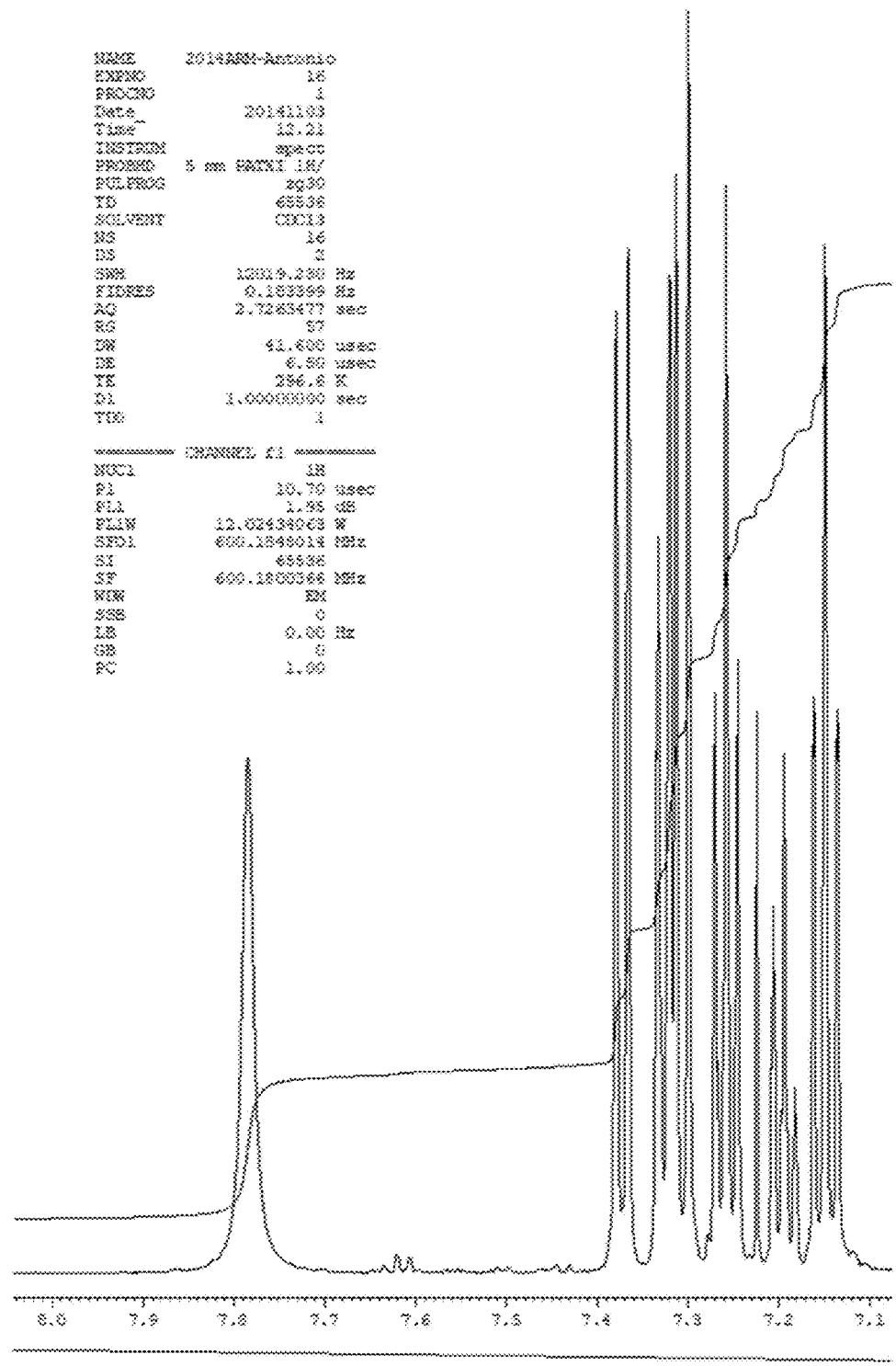
FIG. 1 depicts the $^1H$ NMR spectrum of SP-BIM 1 taken in $CDCl_3$, according to one or more embodiments.
Figure 1:
Figure 1:
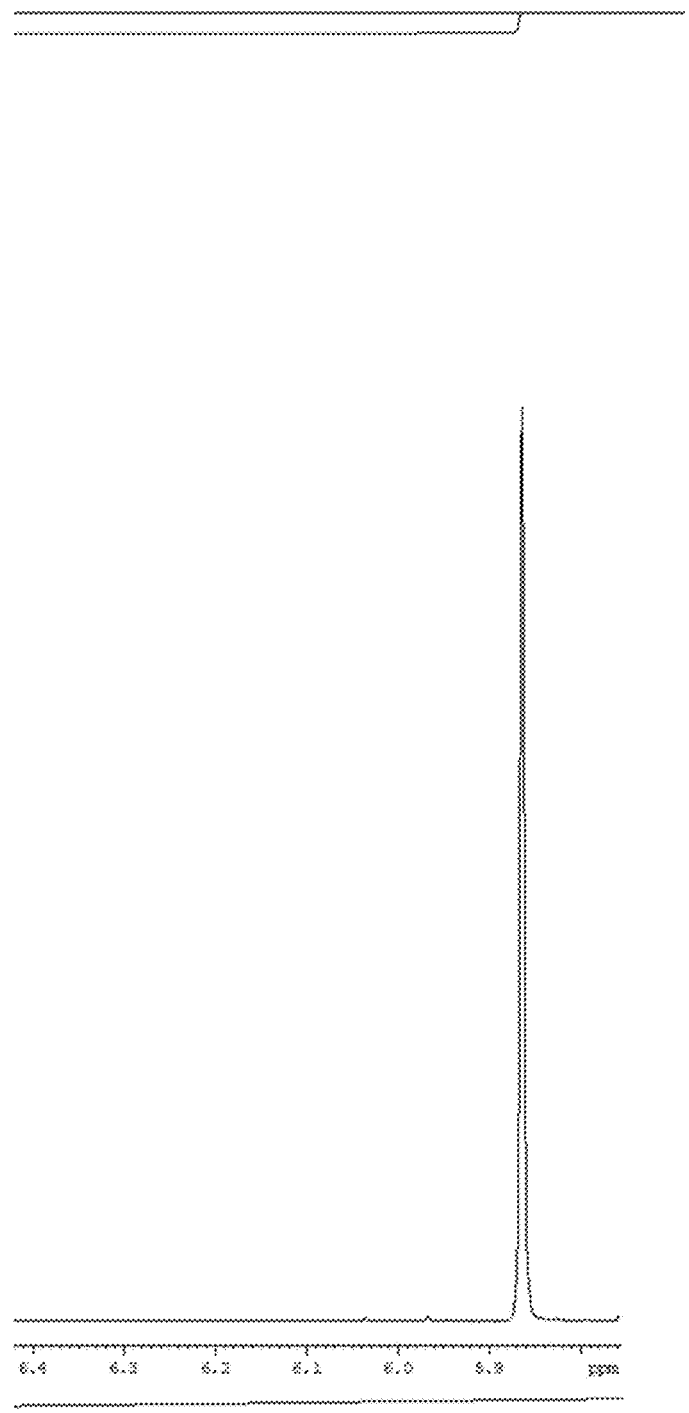
Figure 2:
FIG. 2 depicts the $^{13}C$ NMR spectrum of SP-BIM 1 taken in $CDCl_3$, according to one or more embodiments.
Figure 2:
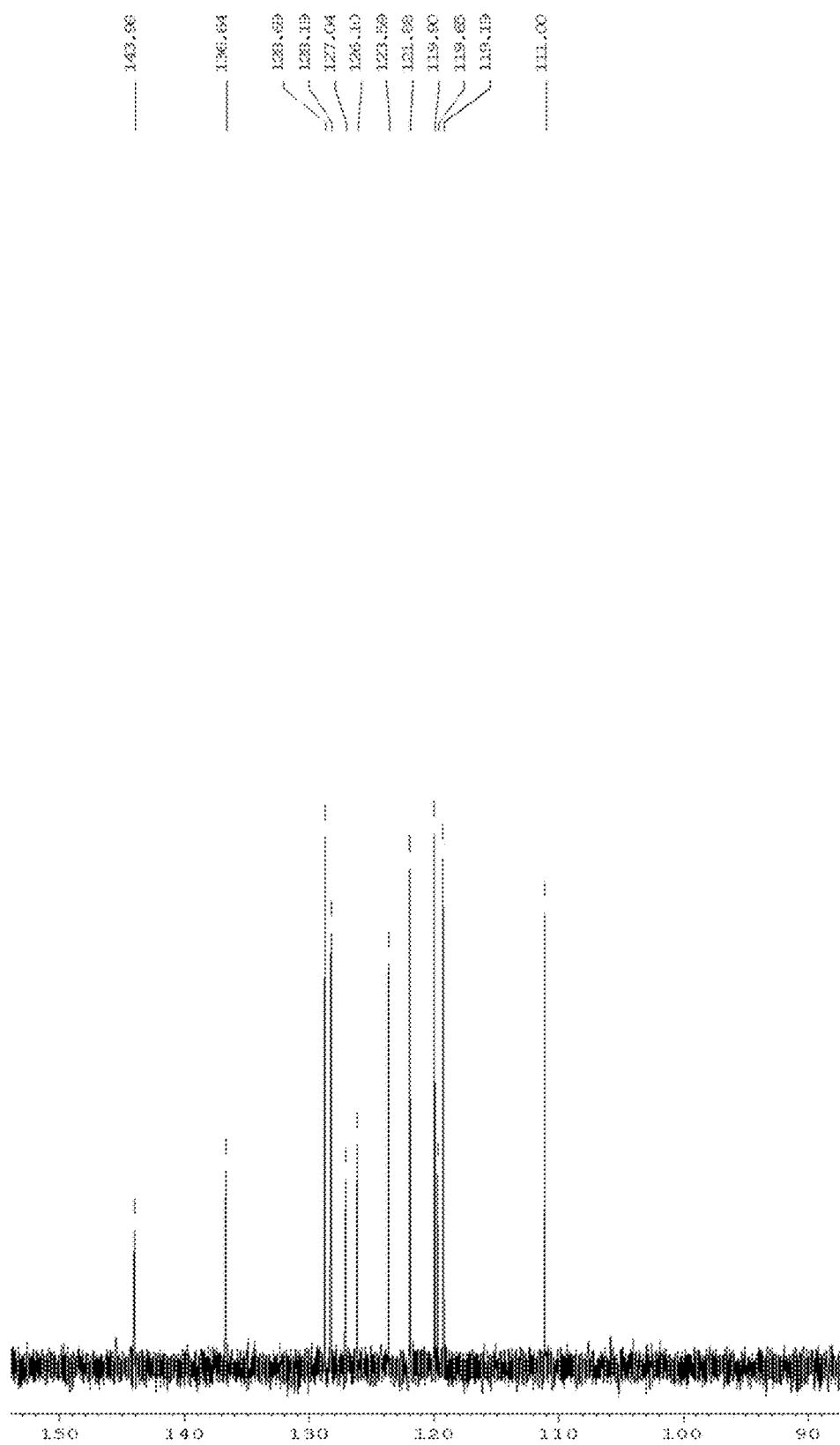
Figure 2:
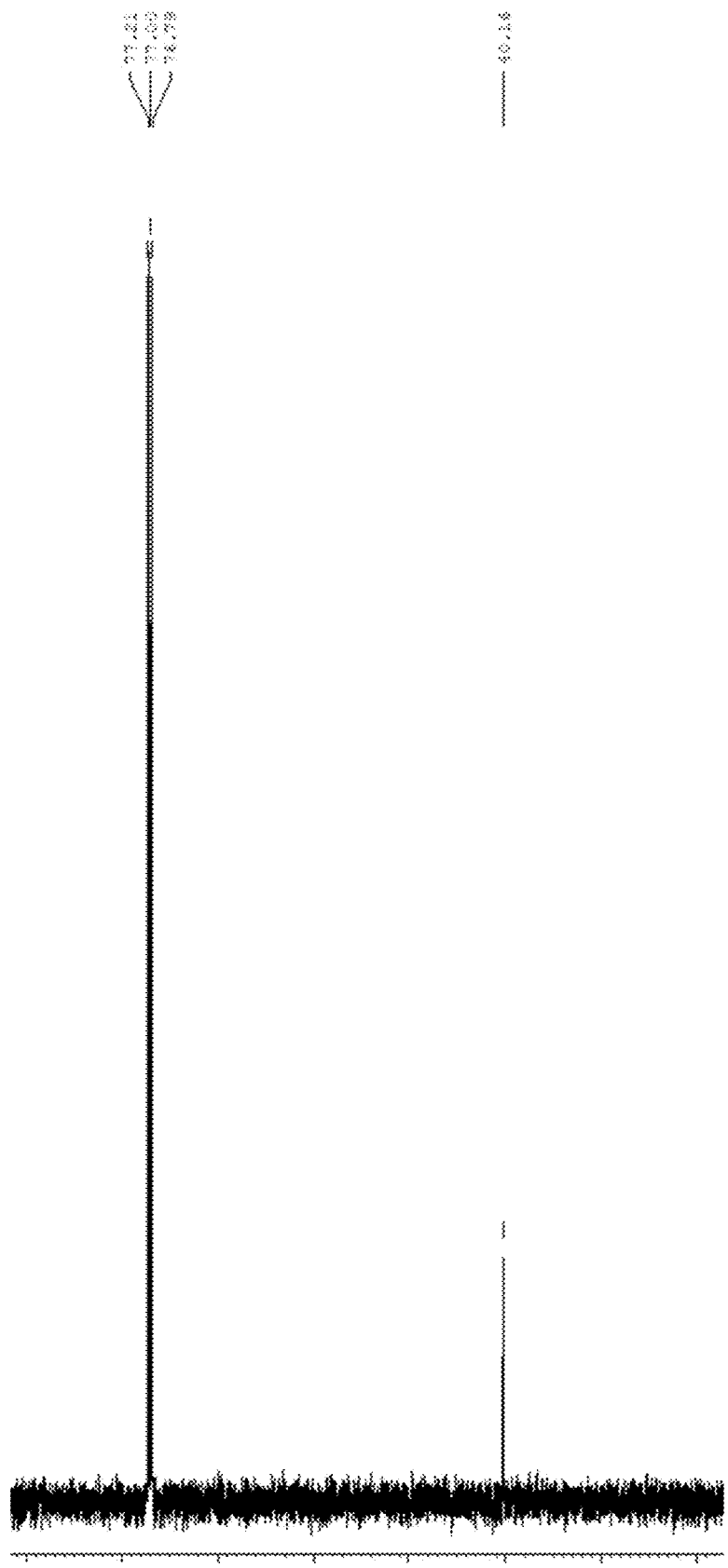
Figure 2:
Figure 3A:
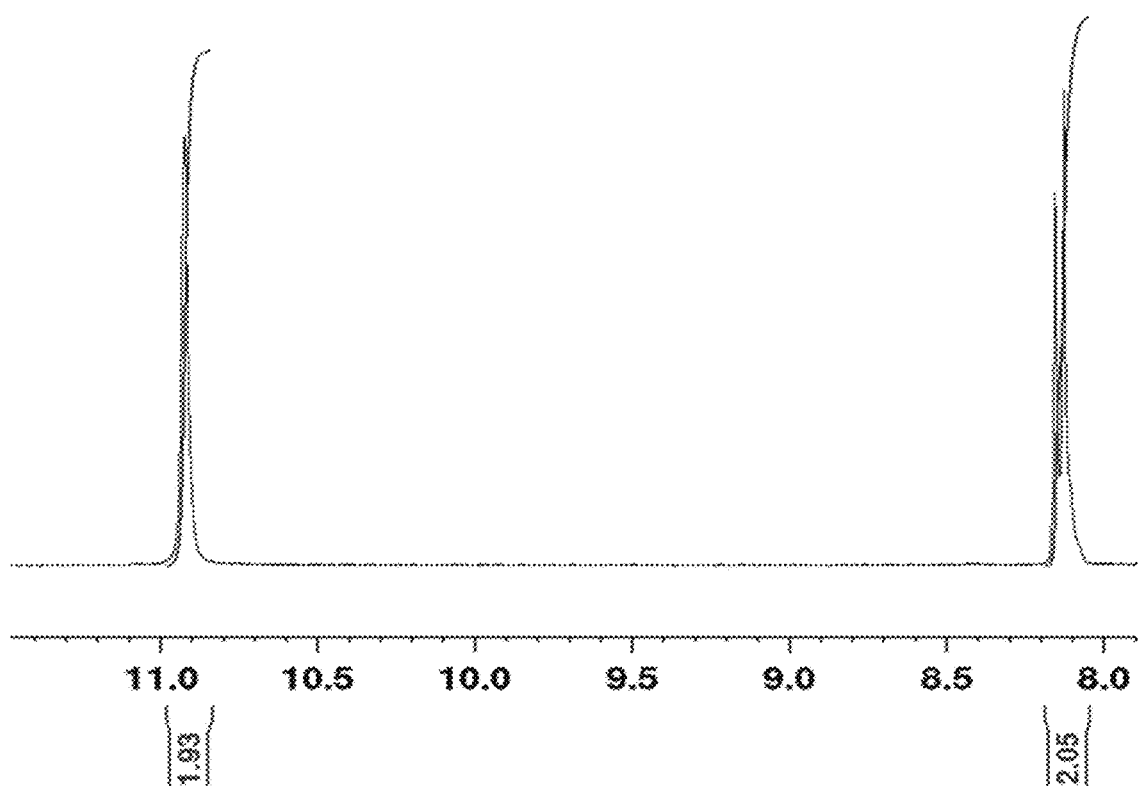
FIG. 3A depicts the $^1H$ NMR spectrum of SP-BIM 8 taken in DMSO-d6, according to one or more embodiments.
Figure 3A:
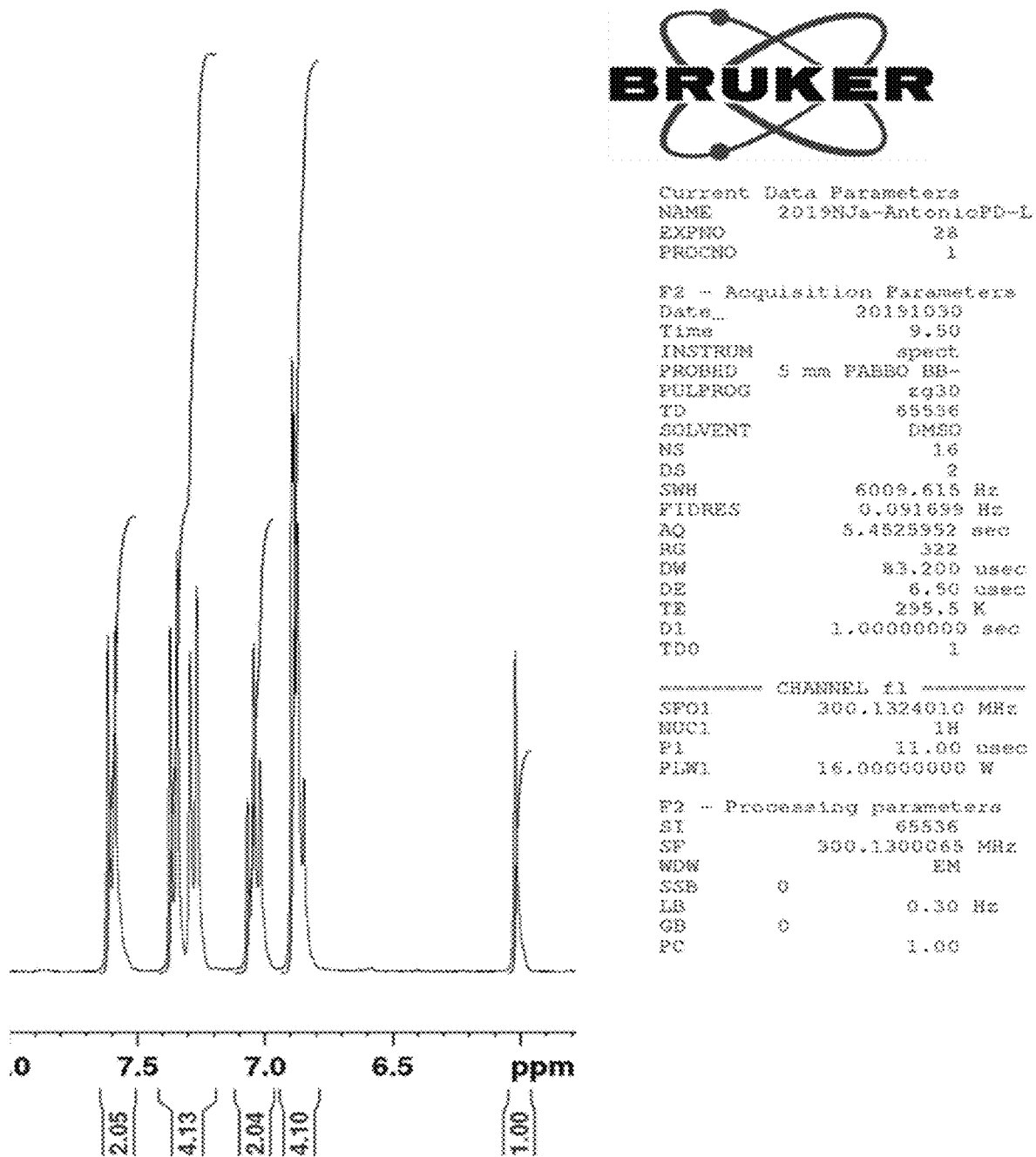
Figure 3B:
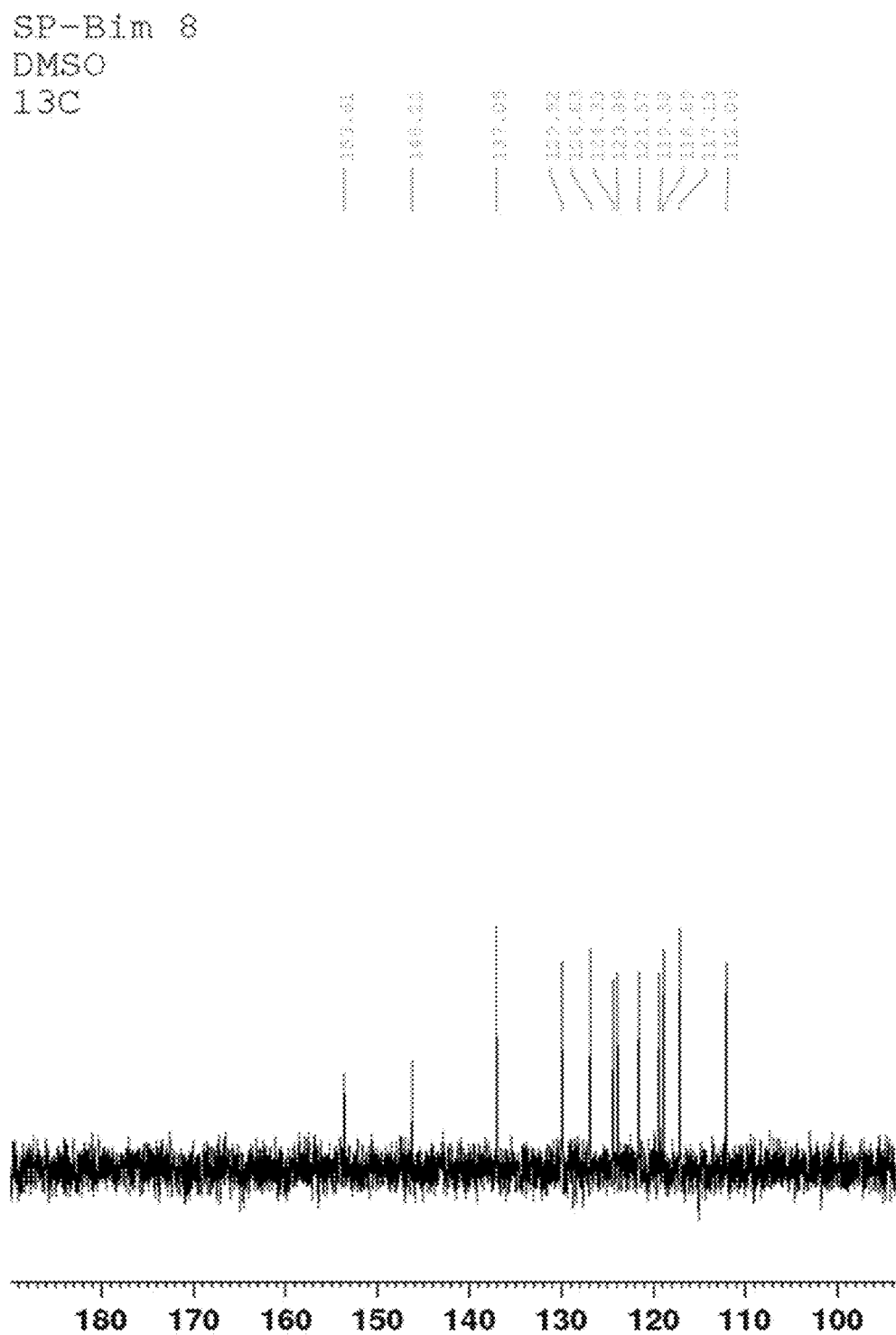
FIG. 3B depicts the $^{13}$C NMR spectrum of SP-BIM 8 taken in DMSO-d6, according to one or more embodiments.
Figure 3B:
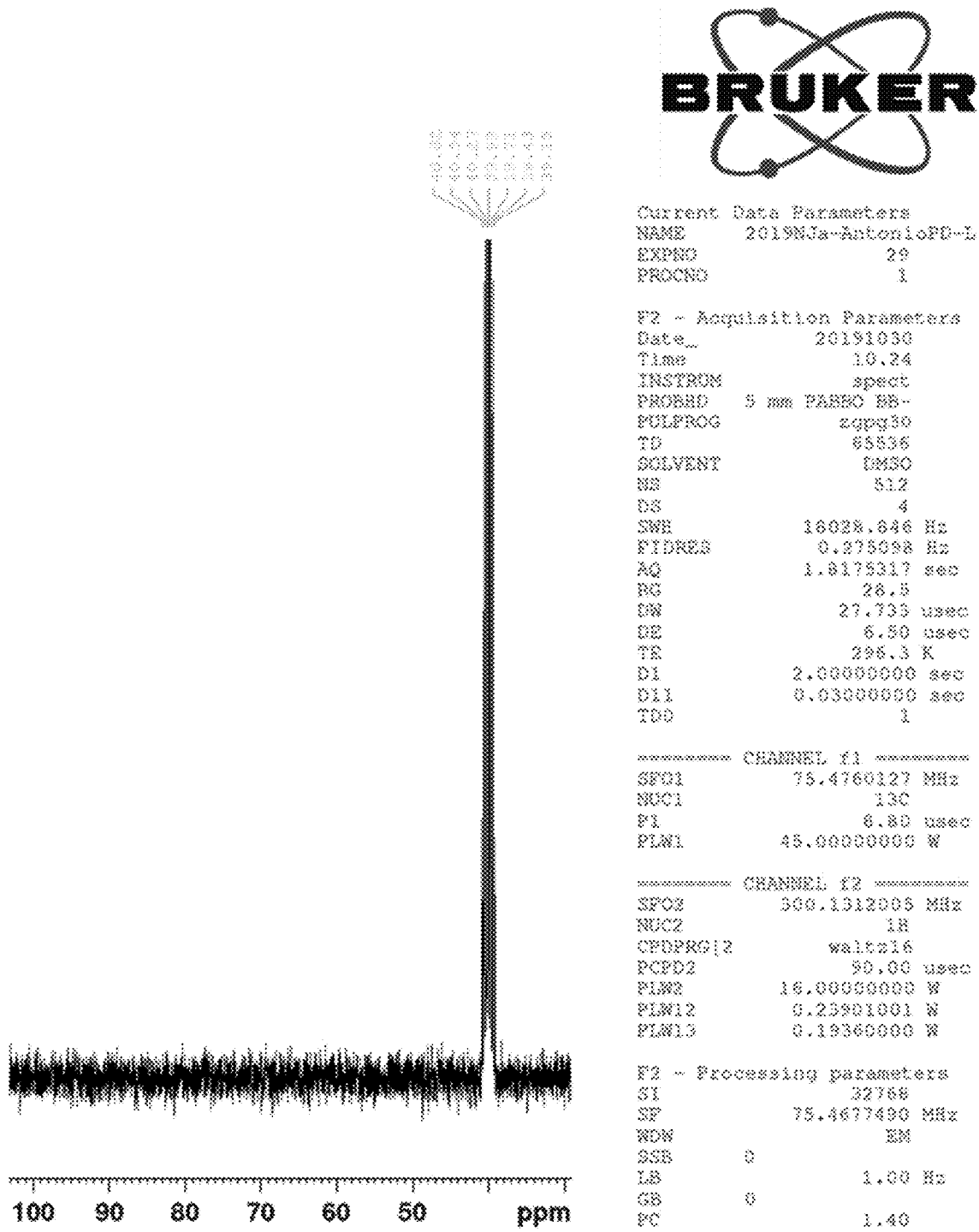
Figure 4A:
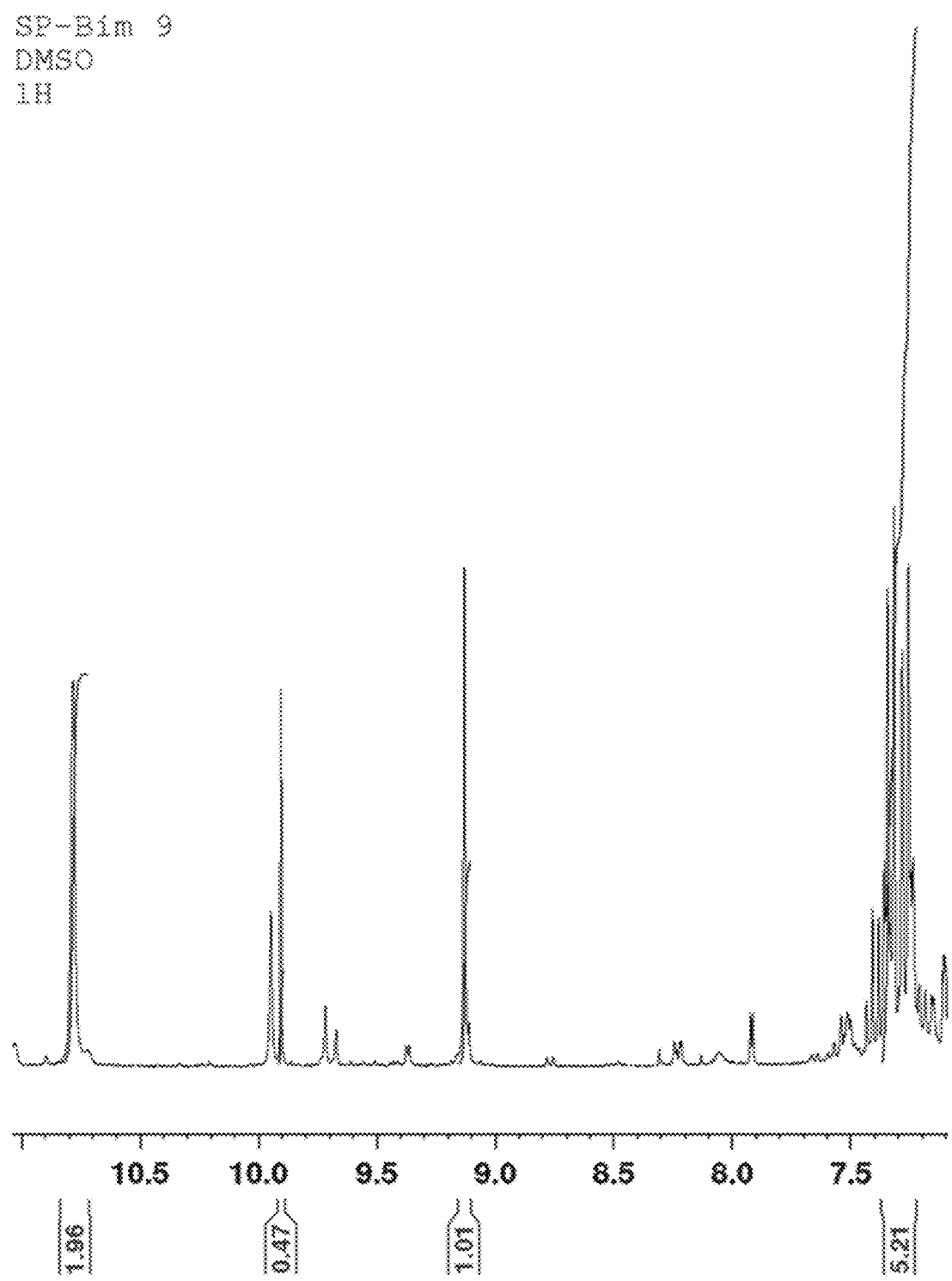
FIG. 4A depicts the $^1$H NMR spectrum of SP-BIM 9 taken in DMSO-d6, according to one or more embodiments.
Figure 4A:
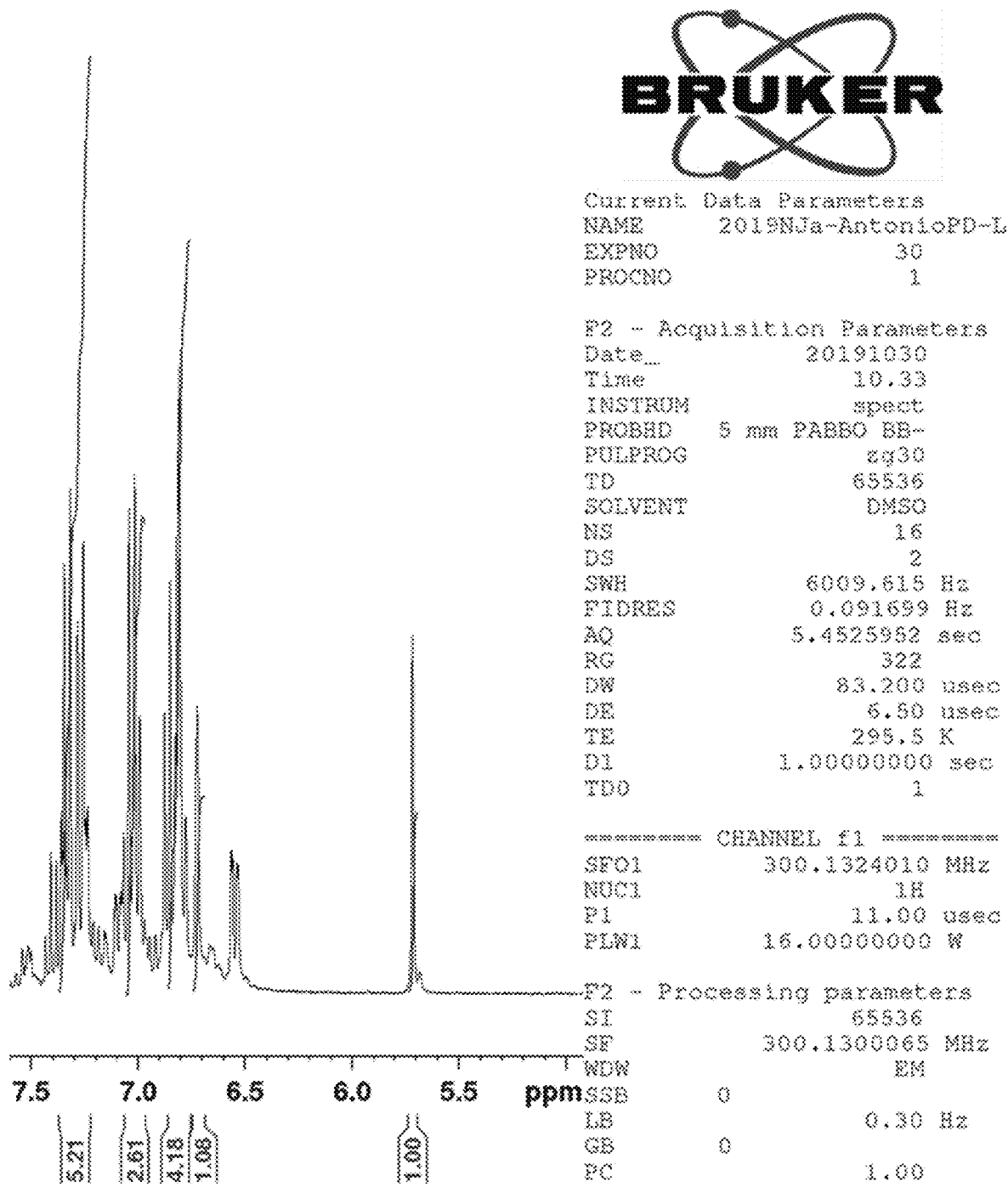
Figure 4B:
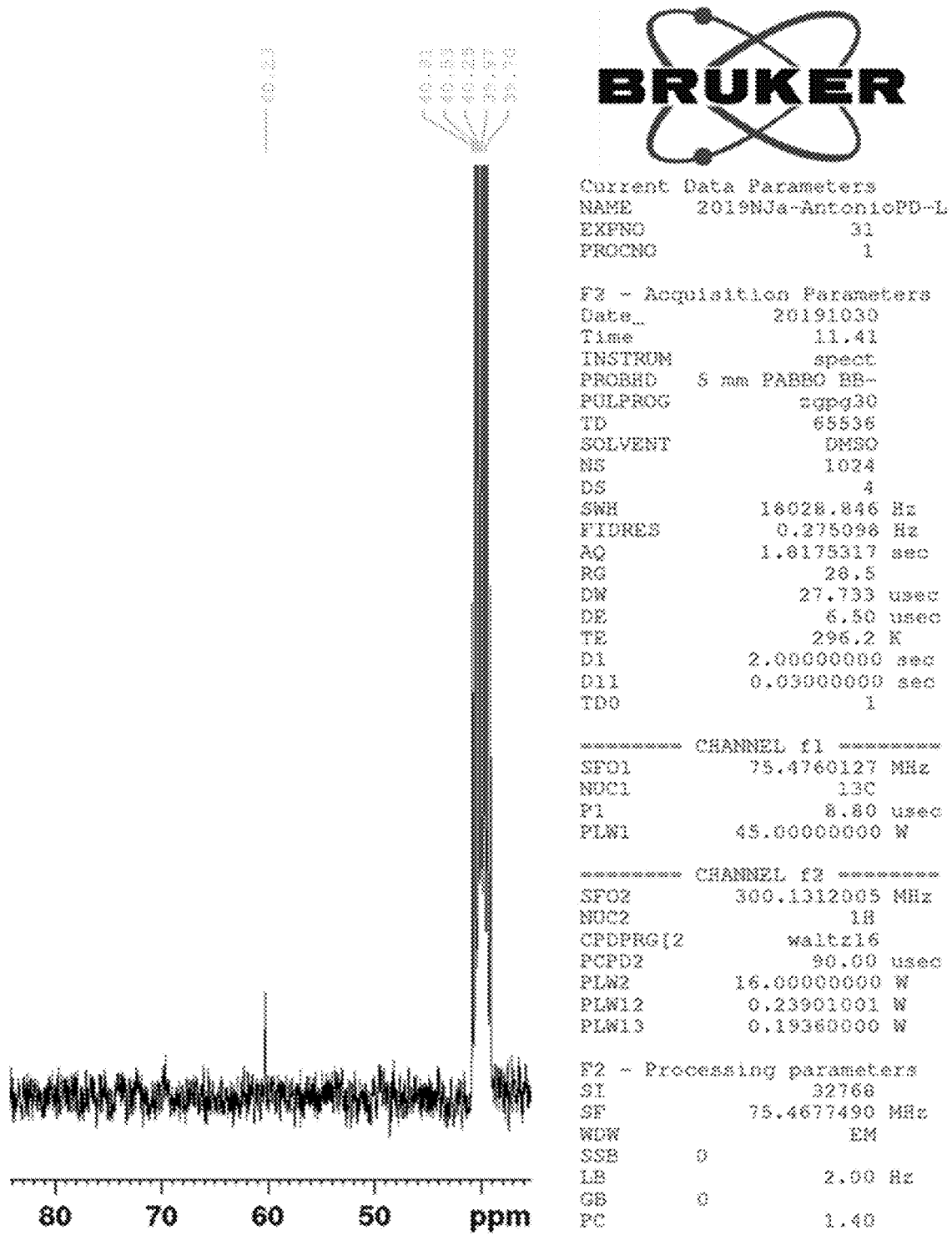
FIG. 4B depicts the $^{13}$C NMR spectrum of SP-BIM 9 taken in DMSO-d6, according to one or more embodiments.
Figure 5A:
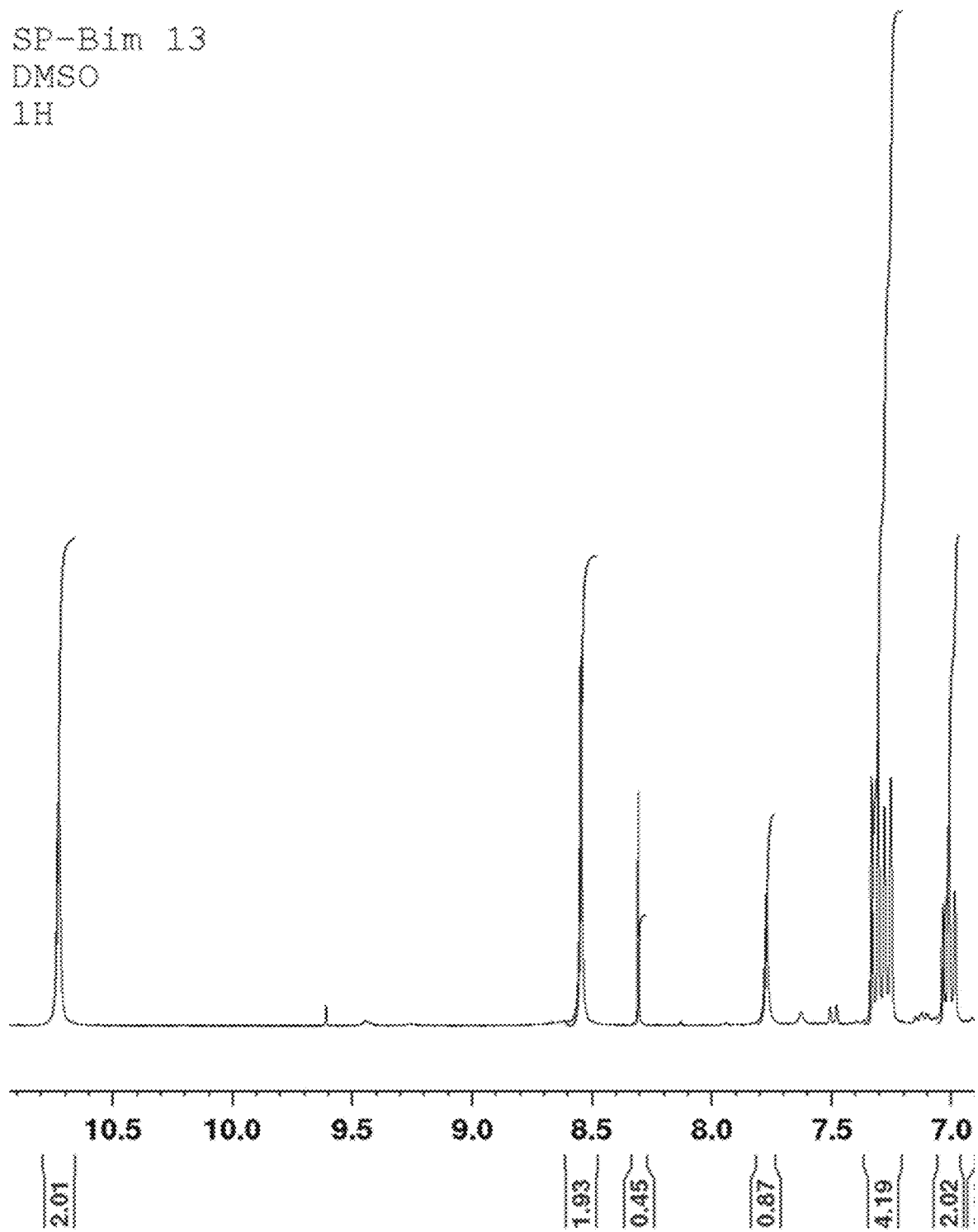
FIG. 5A depicts the $^1$H NMR spectrum of SP-BIM 13 taken in DMSO-d6, according to one or more embodiments.
Figure 5A:
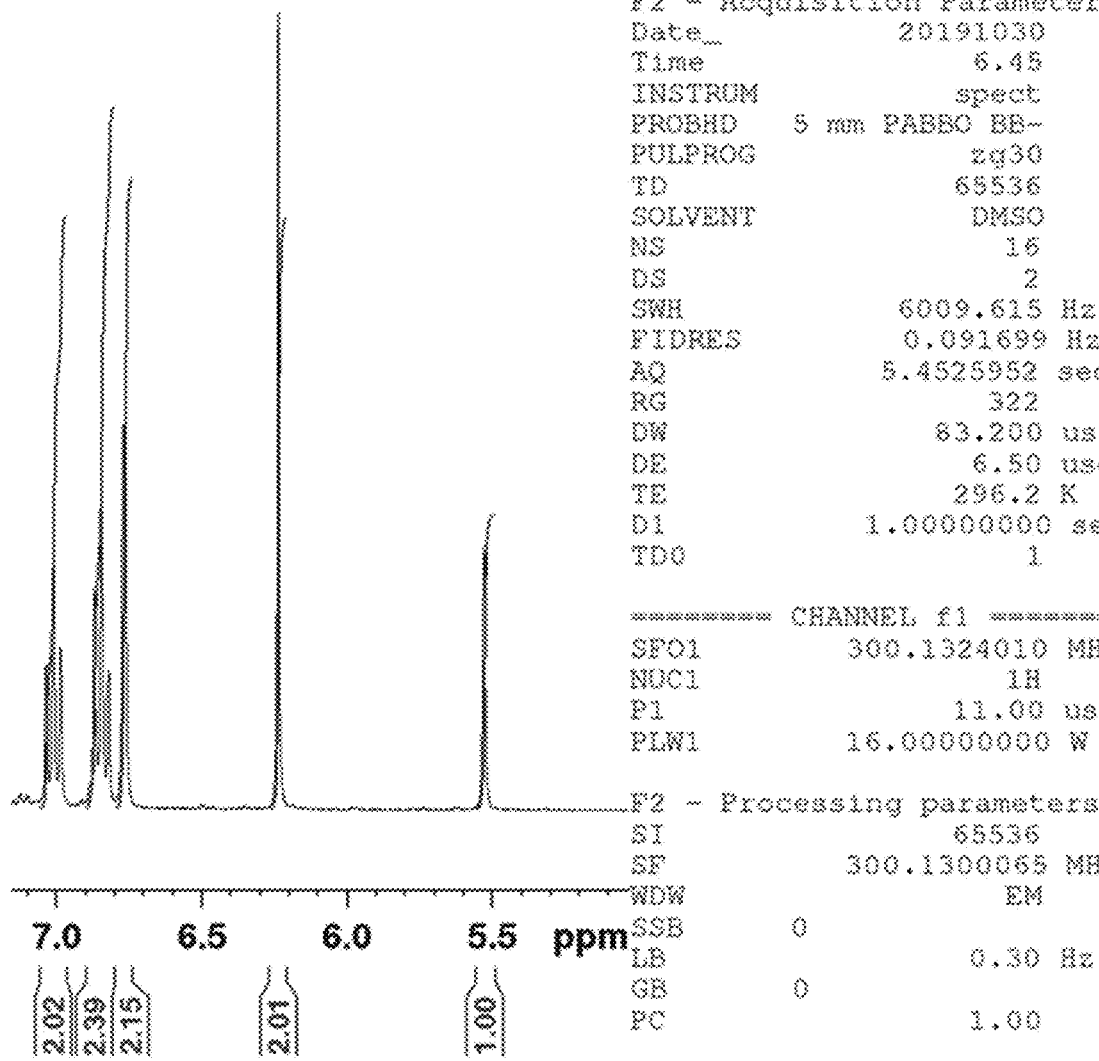
Figure 5B:
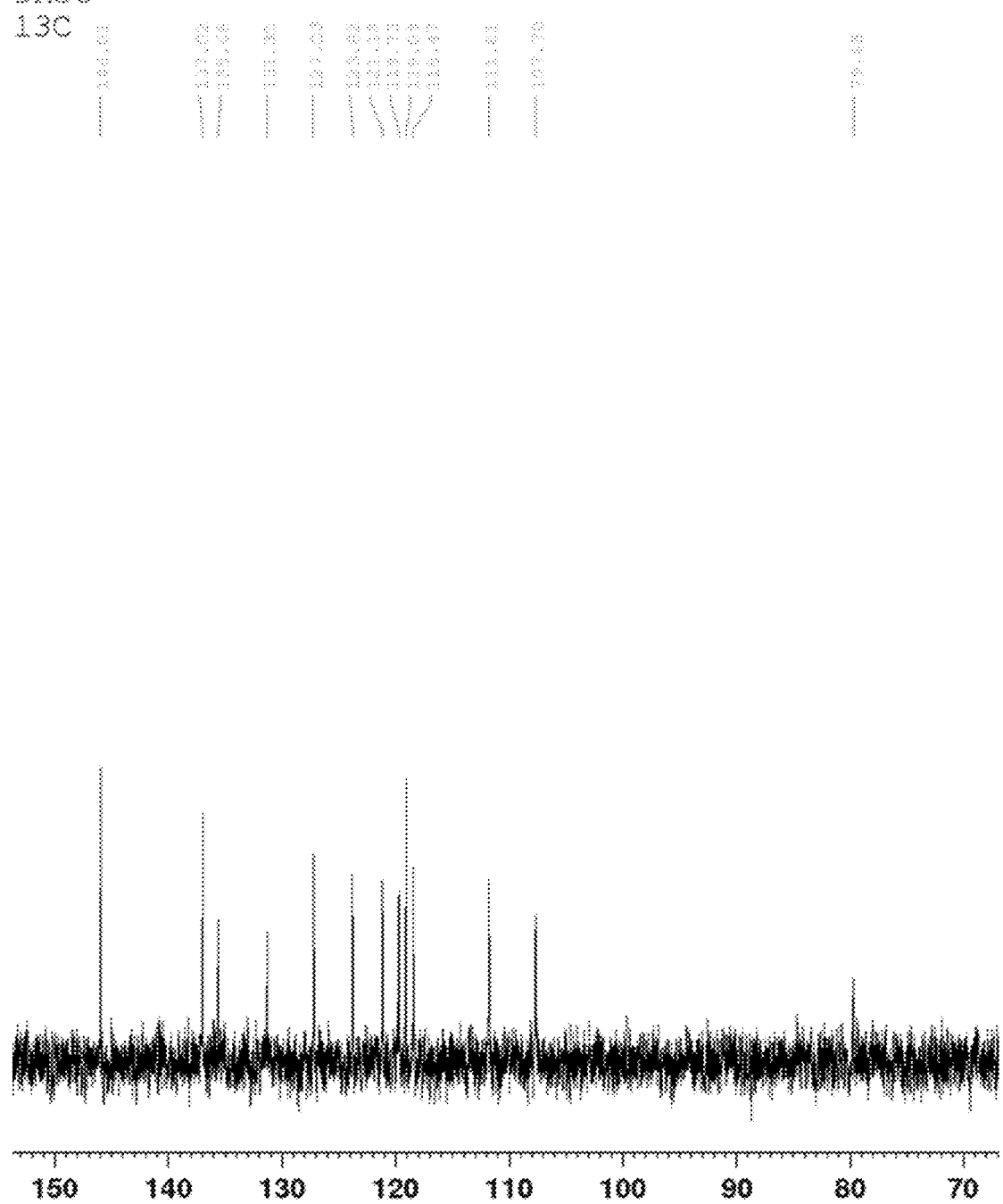
FIG. 5B depicts the $^{13}$C NMR spectrum of SP-BIM 13 taken in DMSO-d6, according to one or more embodiments.
Figure 5B:
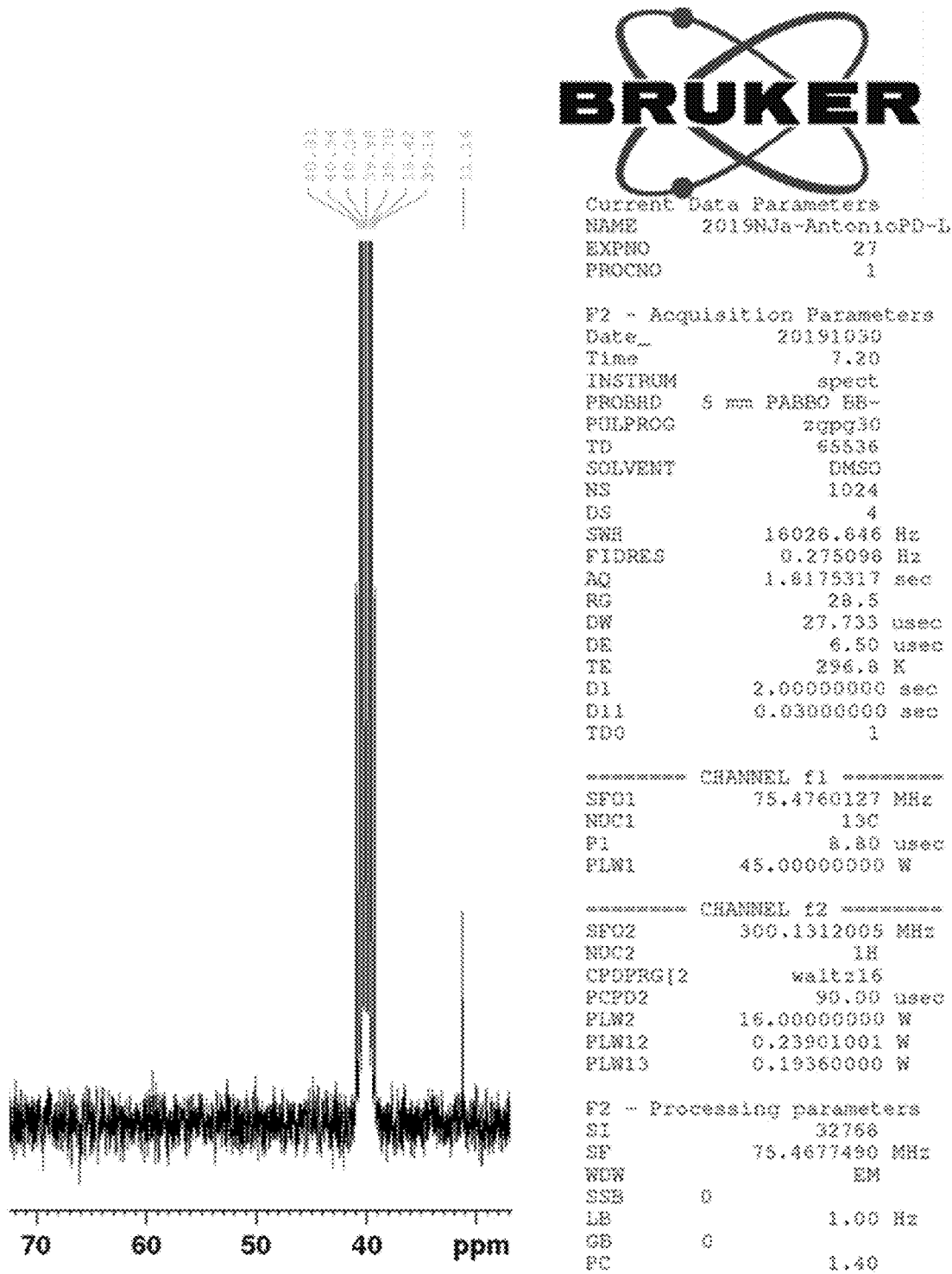
Figure 6A:
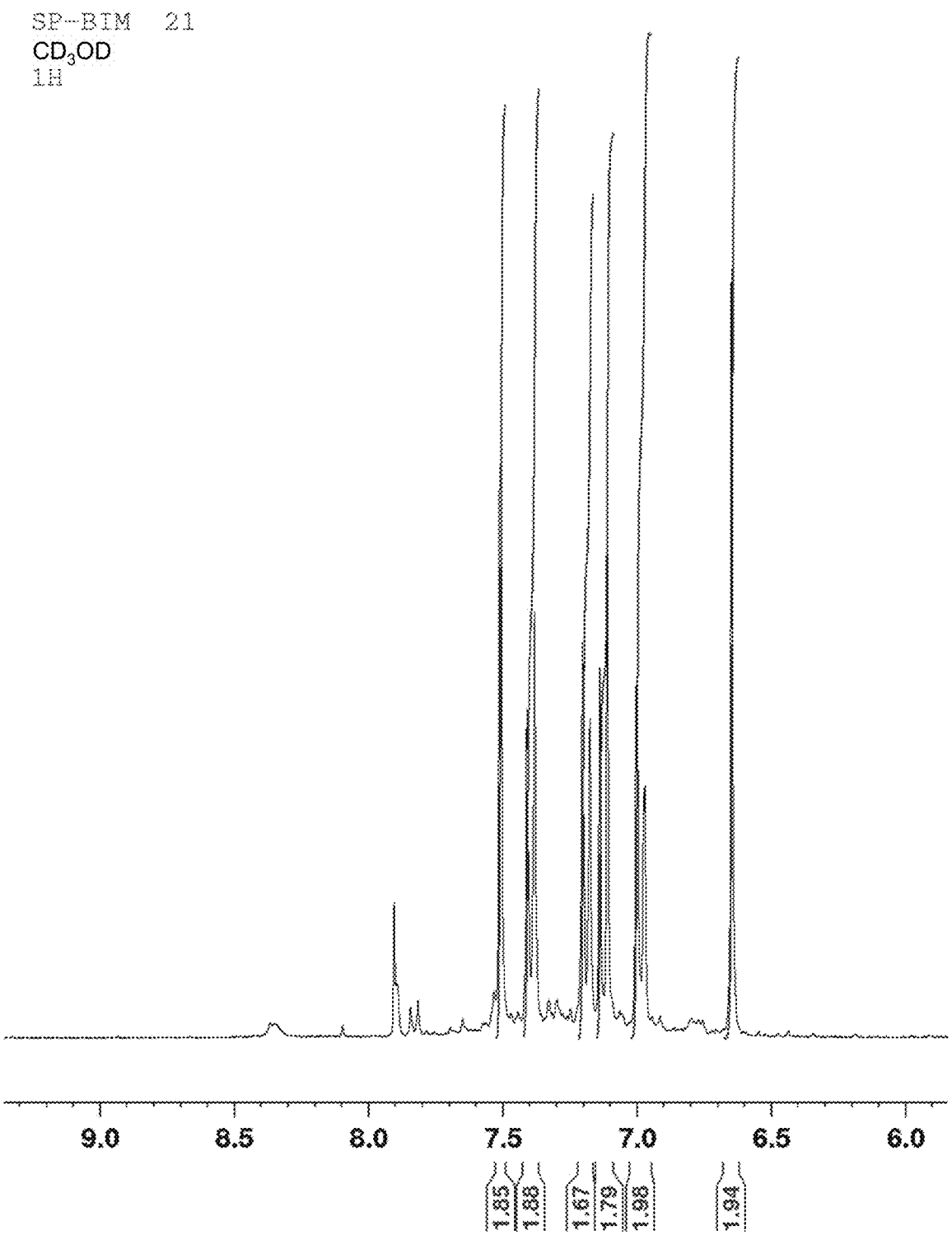
FIG. 6A depicts the $^1$H NMR spectrum of SP-BIM 21 taken in CD$_3$OD, according to one or more embodiments.
Figure 6A:
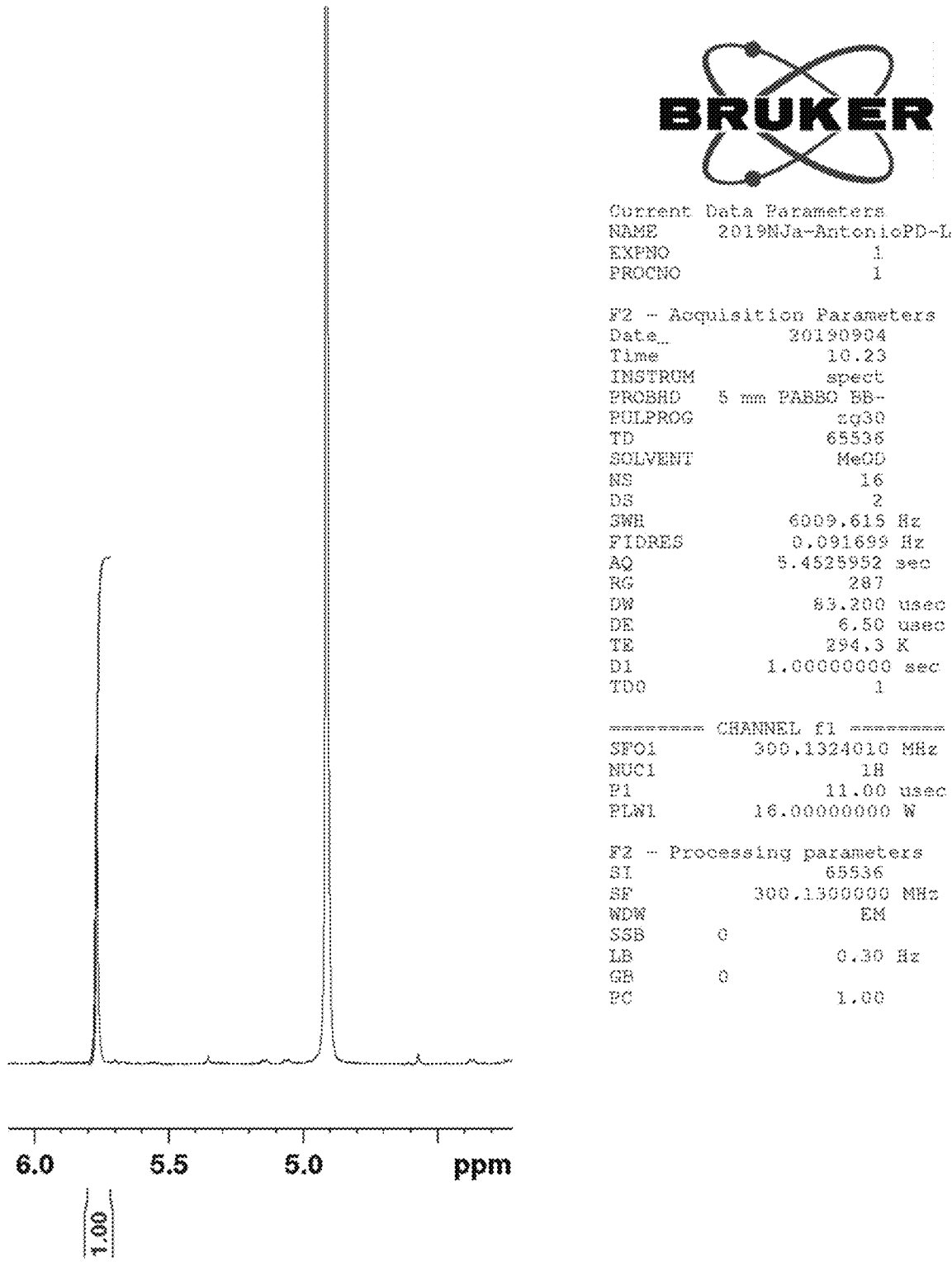
Figure 6B:
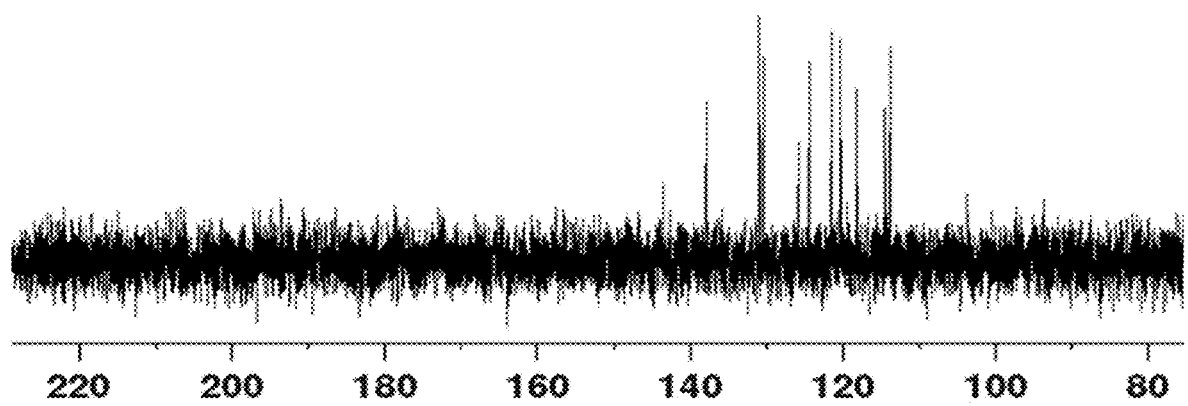
FIG. 6B depicts the $^{13}$C NMR spectrum of SP-BIM 21 taken in CD$_3$OD, according to one or more embodiments.
Figure 6B:
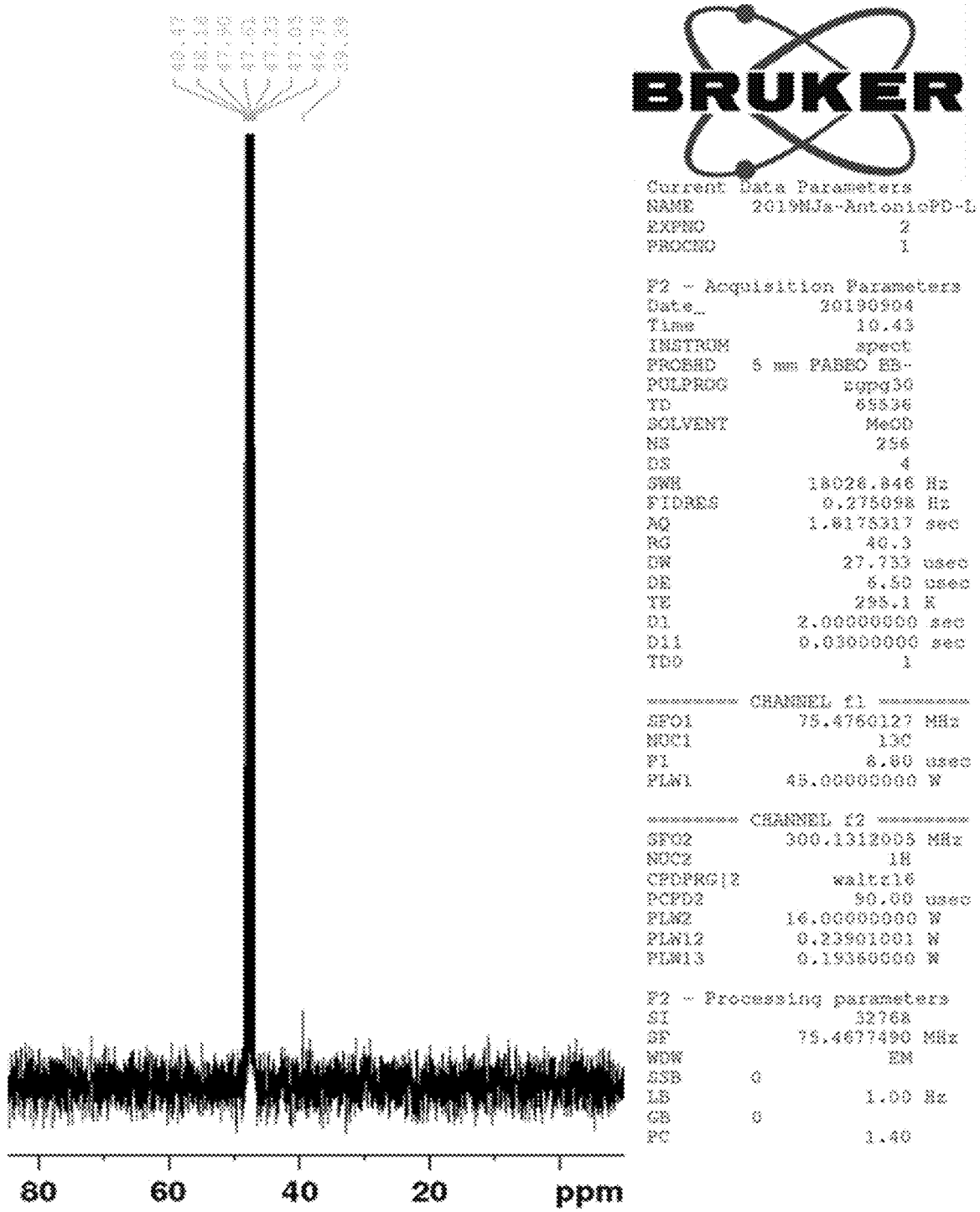
Figure 7A:
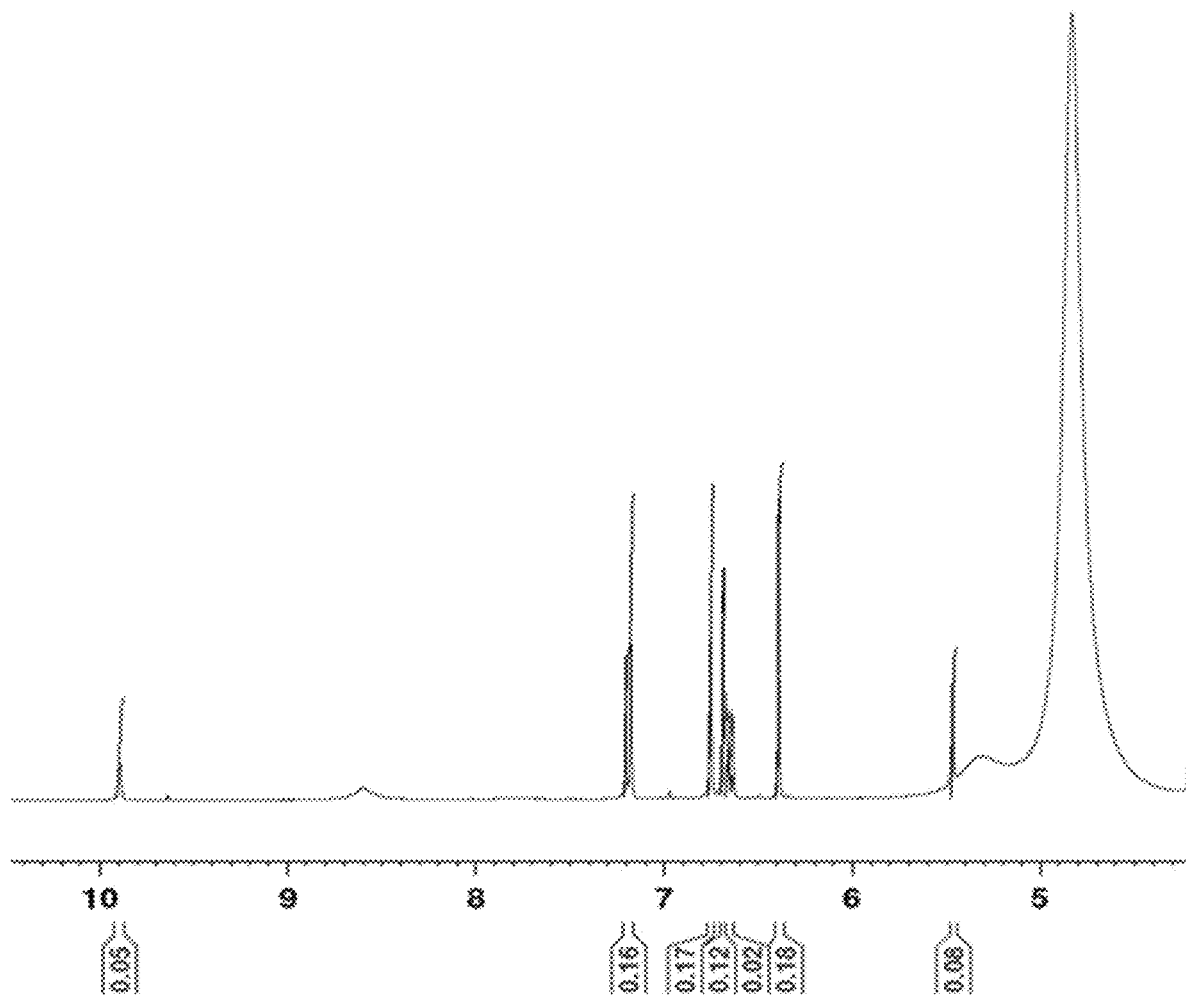
FIG. 7A depicts the $^1$H NMR spectrum of SP-BIM 27 taken in CD$_3$OD, according to one or more embodiments.
Figure 7A:
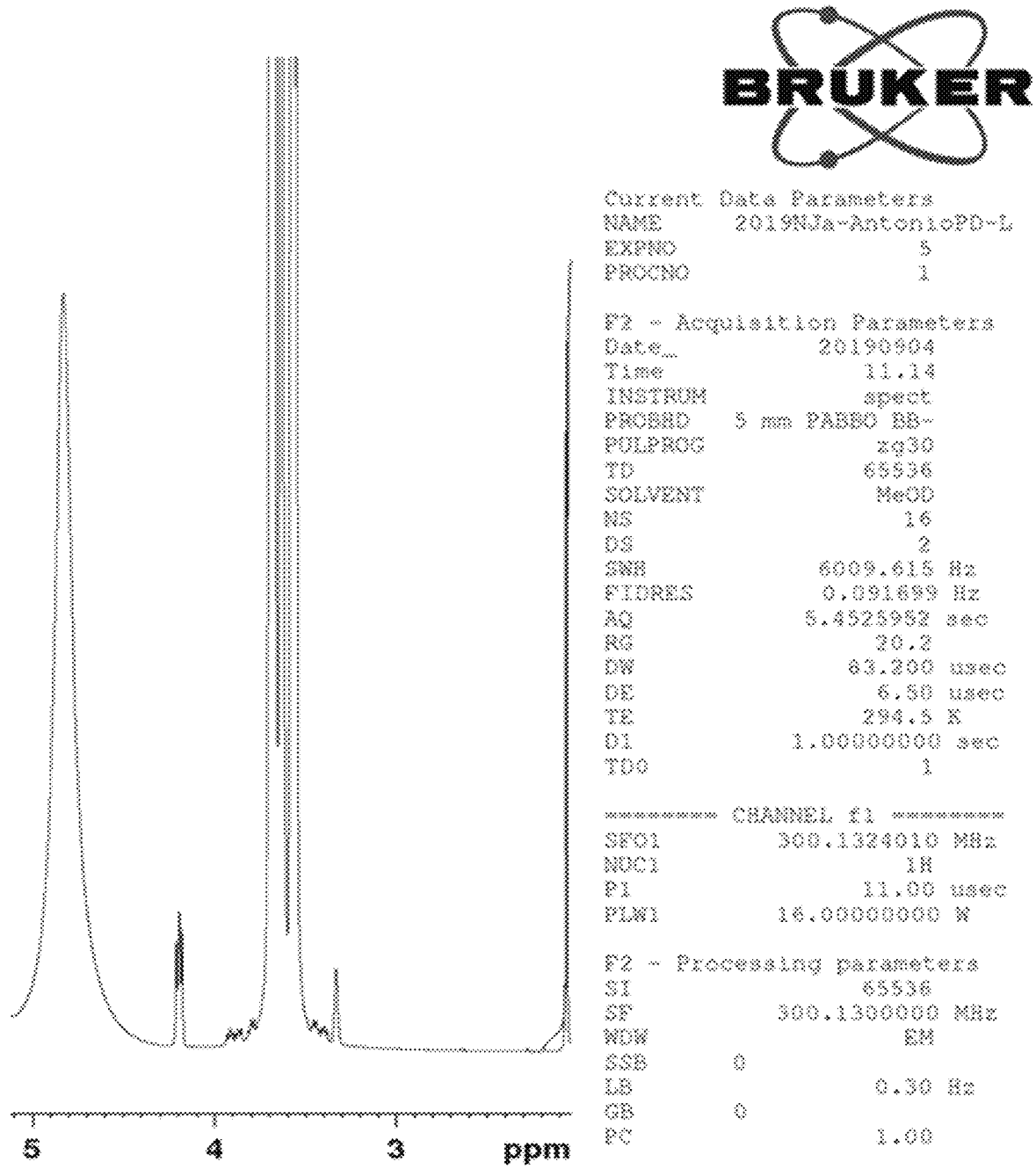
Figure 7B:
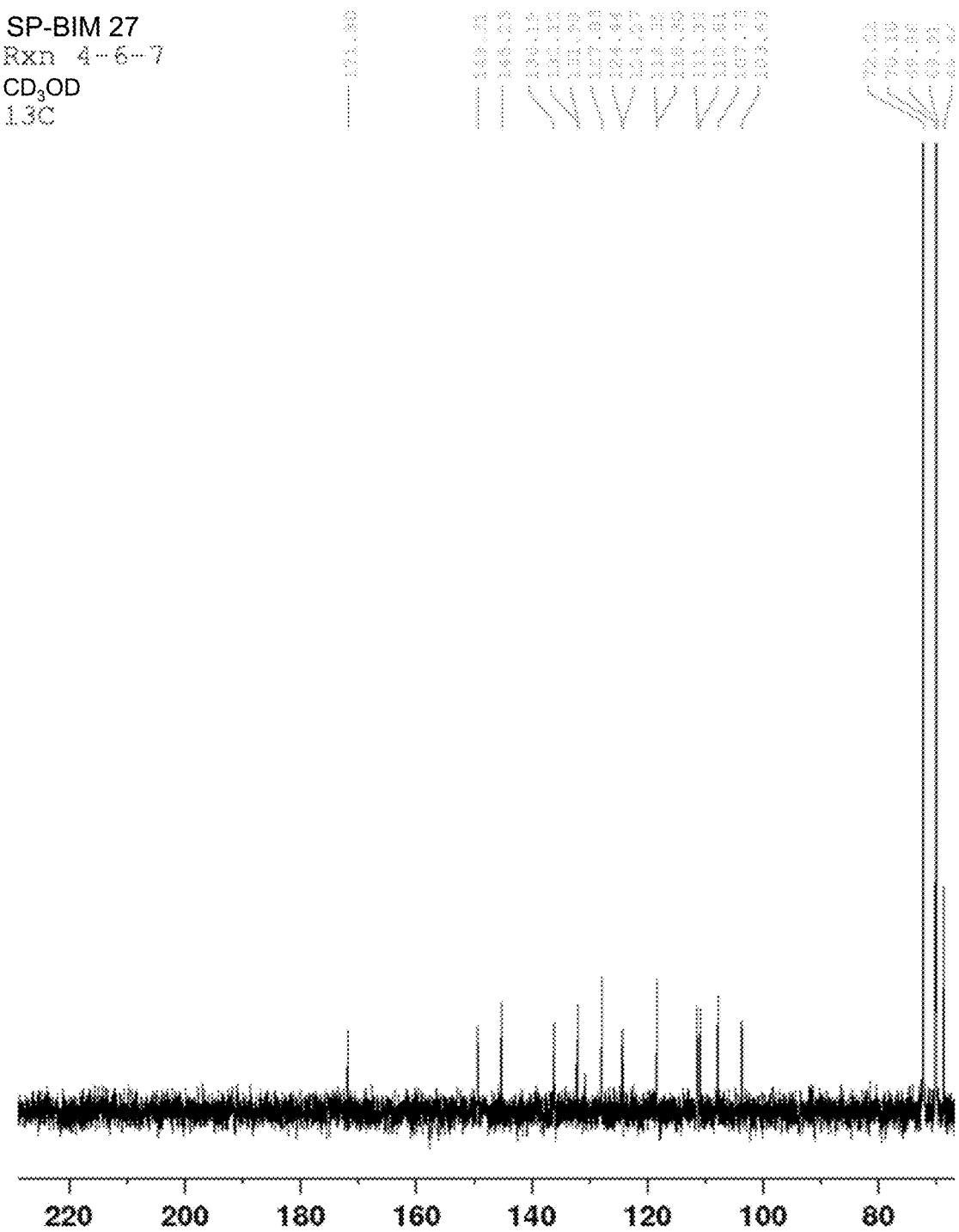
FIG. 7B depicts the $^{13}$C NMR spectrum of SP-BIM 27 taken in CD$_3$OD, according to one or more embodiments.
Figure 7B:
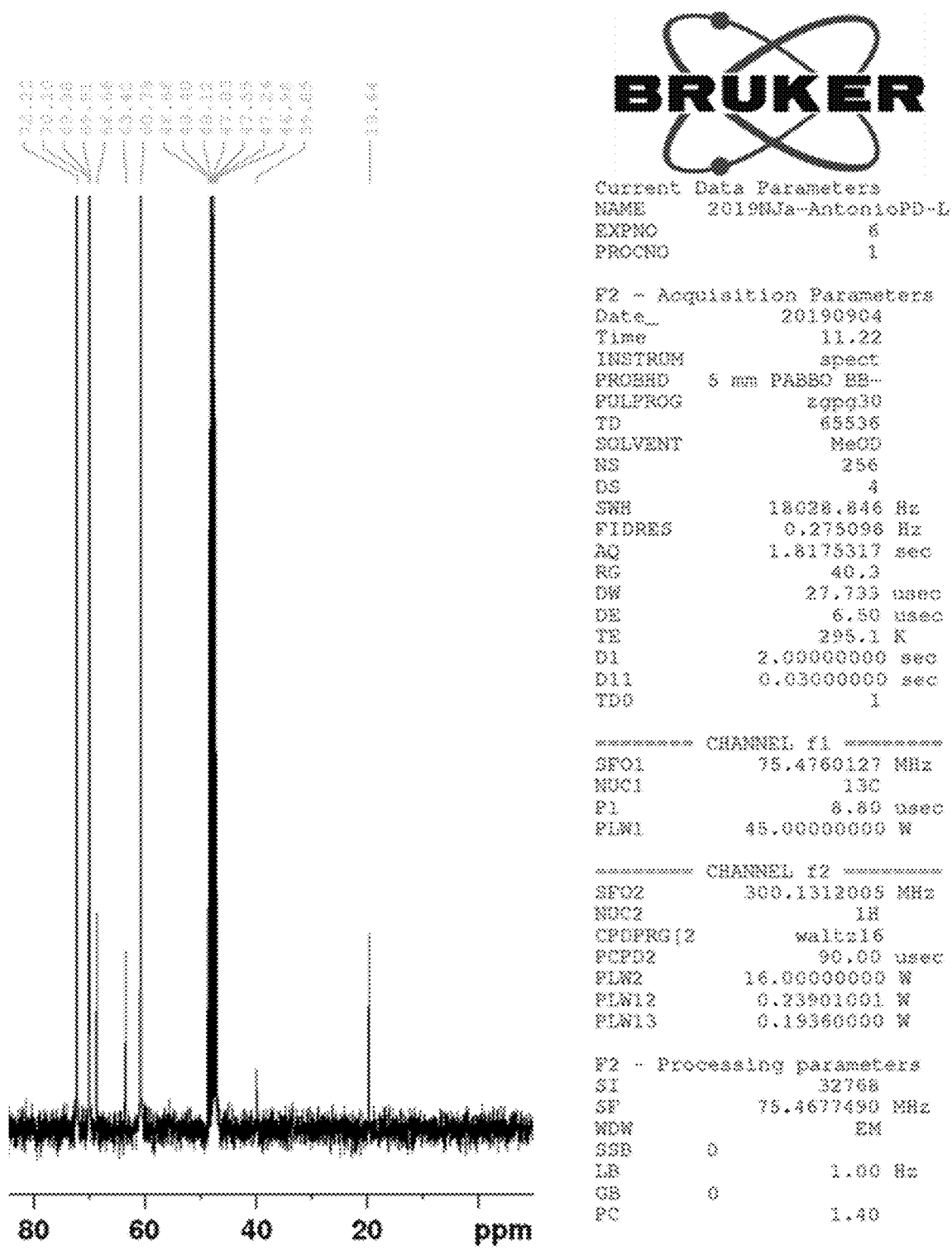
Figure 8A:
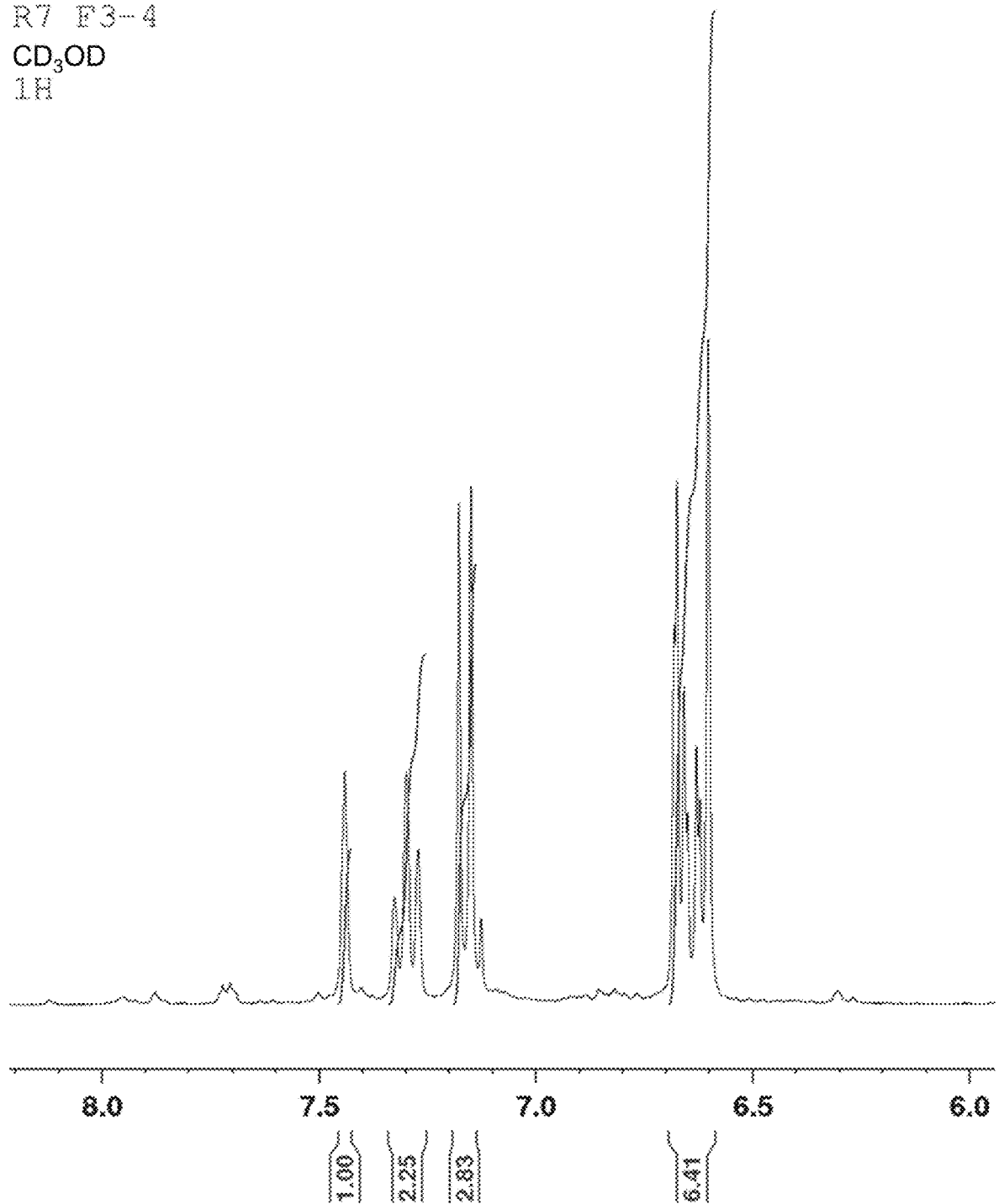
FIG. 8A depicts the $^1$H NMR spectrum of SP-BIM 28 taken in CD$_3$OD, according to one or more embodiments.
Figure 8A:
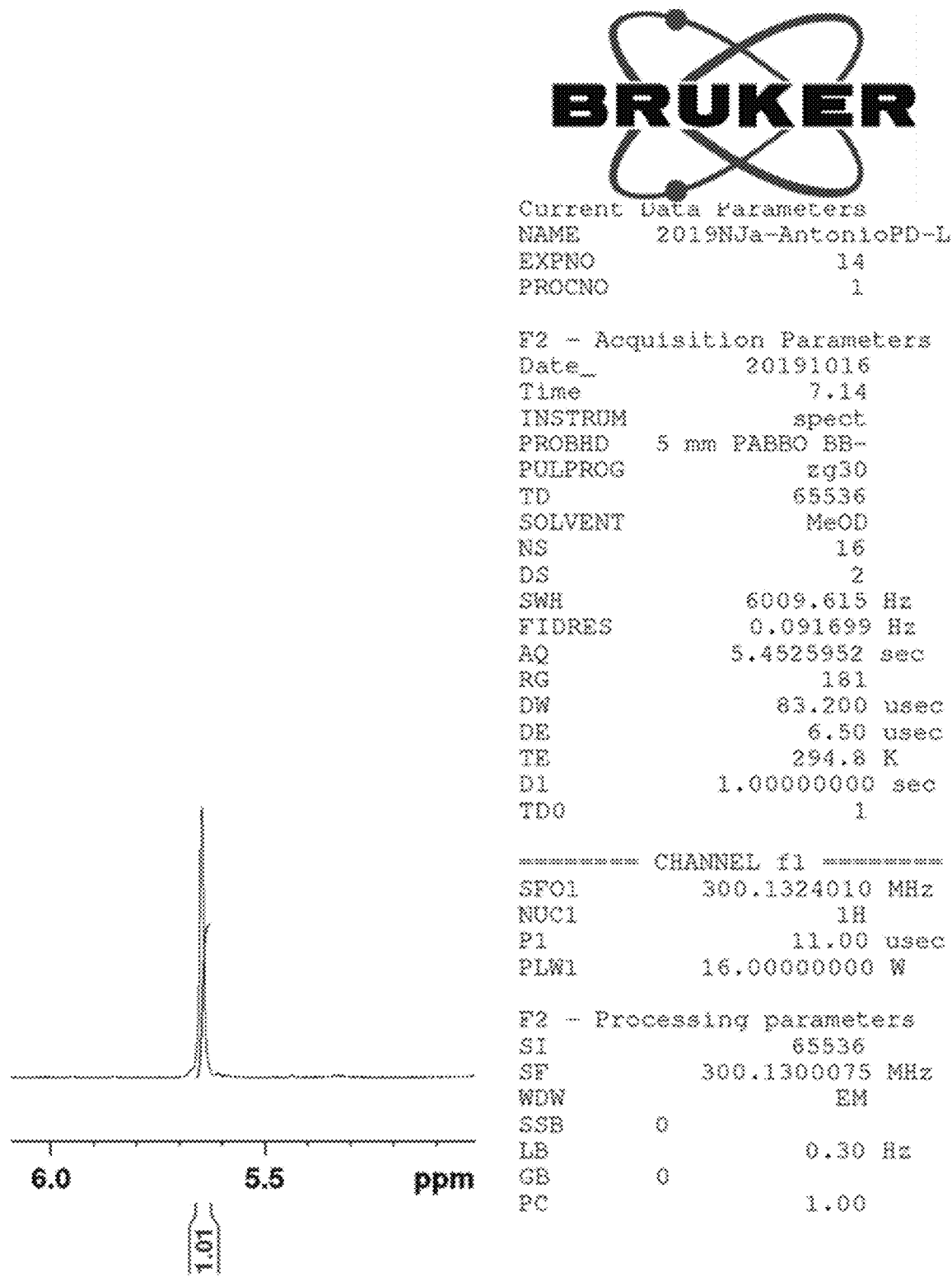
Figure 8B:
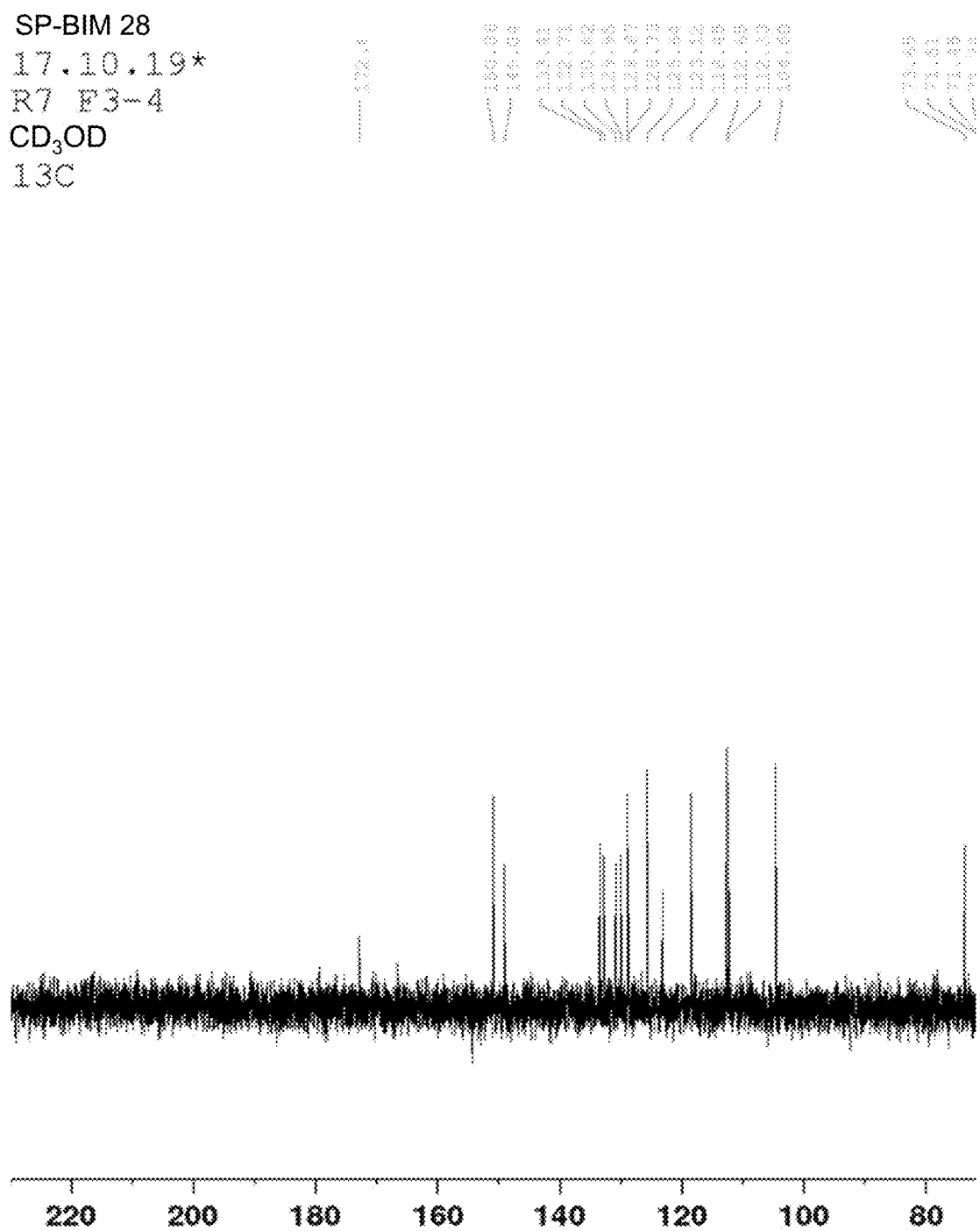
FIG. 8B depicts the $^{13}$C NMR spectrum of SP-BIM 28 taken in CD$_3$OD, according to one or more embodiments.
Figure 8B:
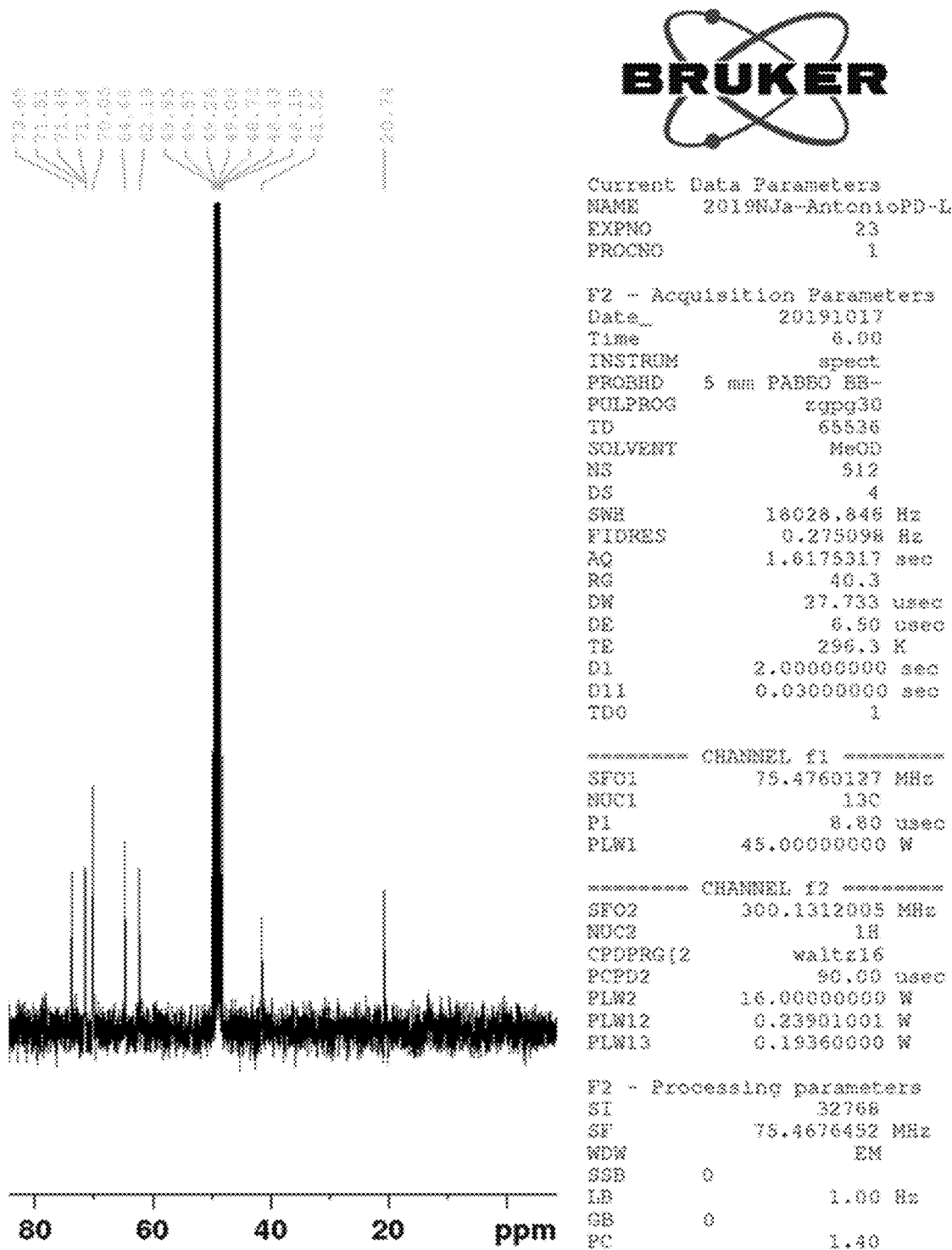
Figure 9A:
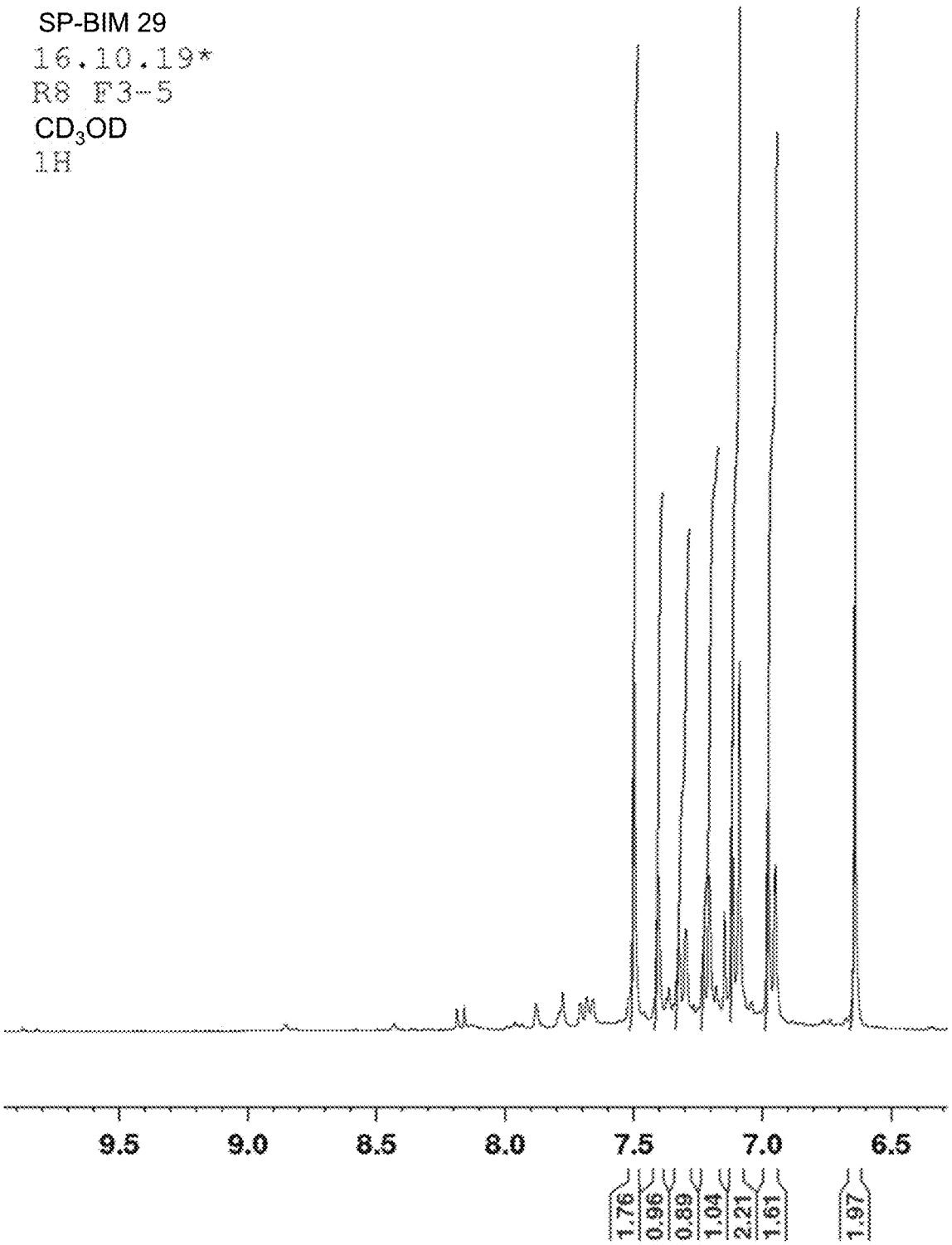
FIG. 9A depicts the $^1$H NMR spectrum of SP-BIM 29 taken in CD$_3$OD, according to one or more embodiments.
Figure 9A:
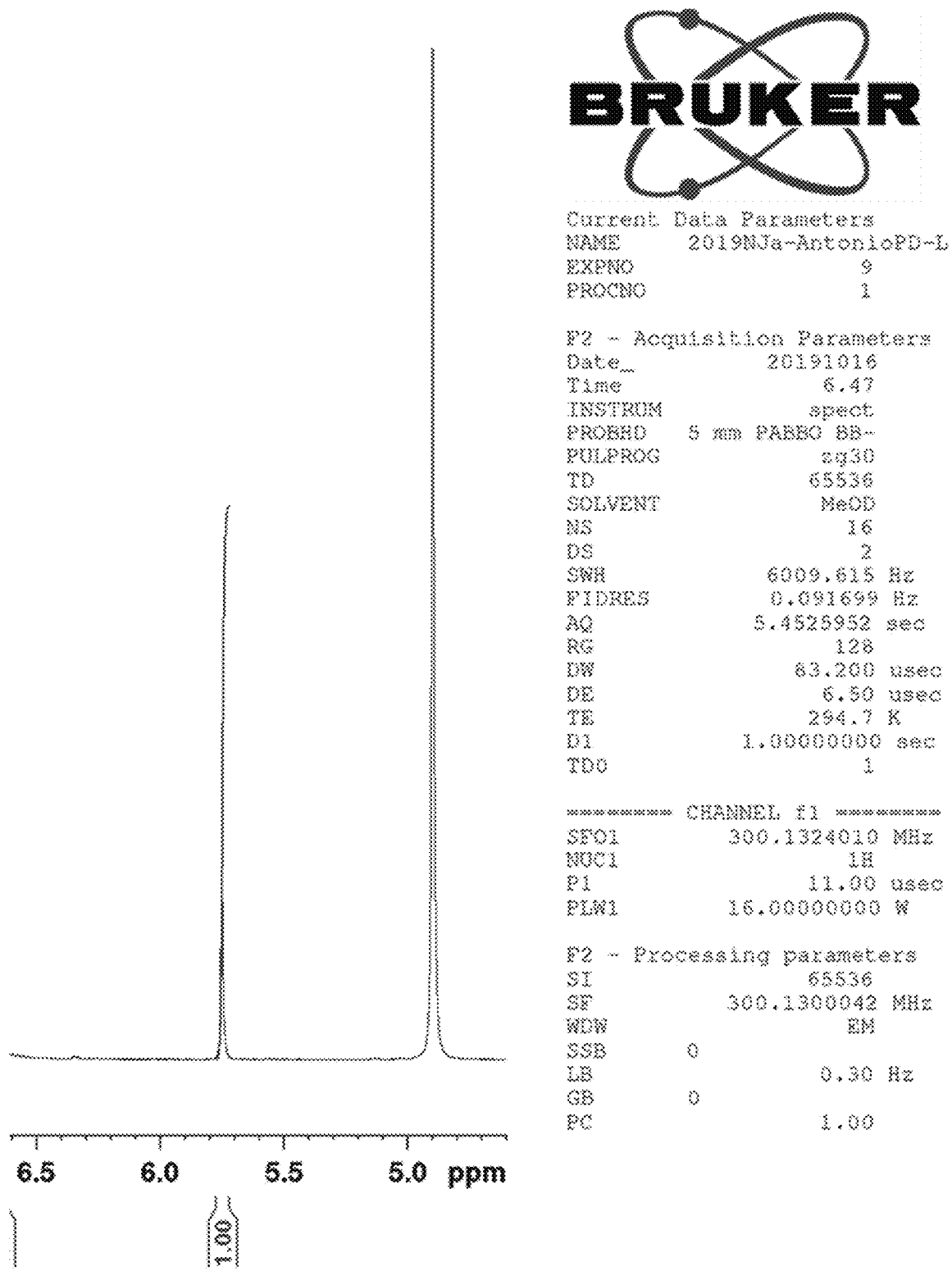
Figure 9B:
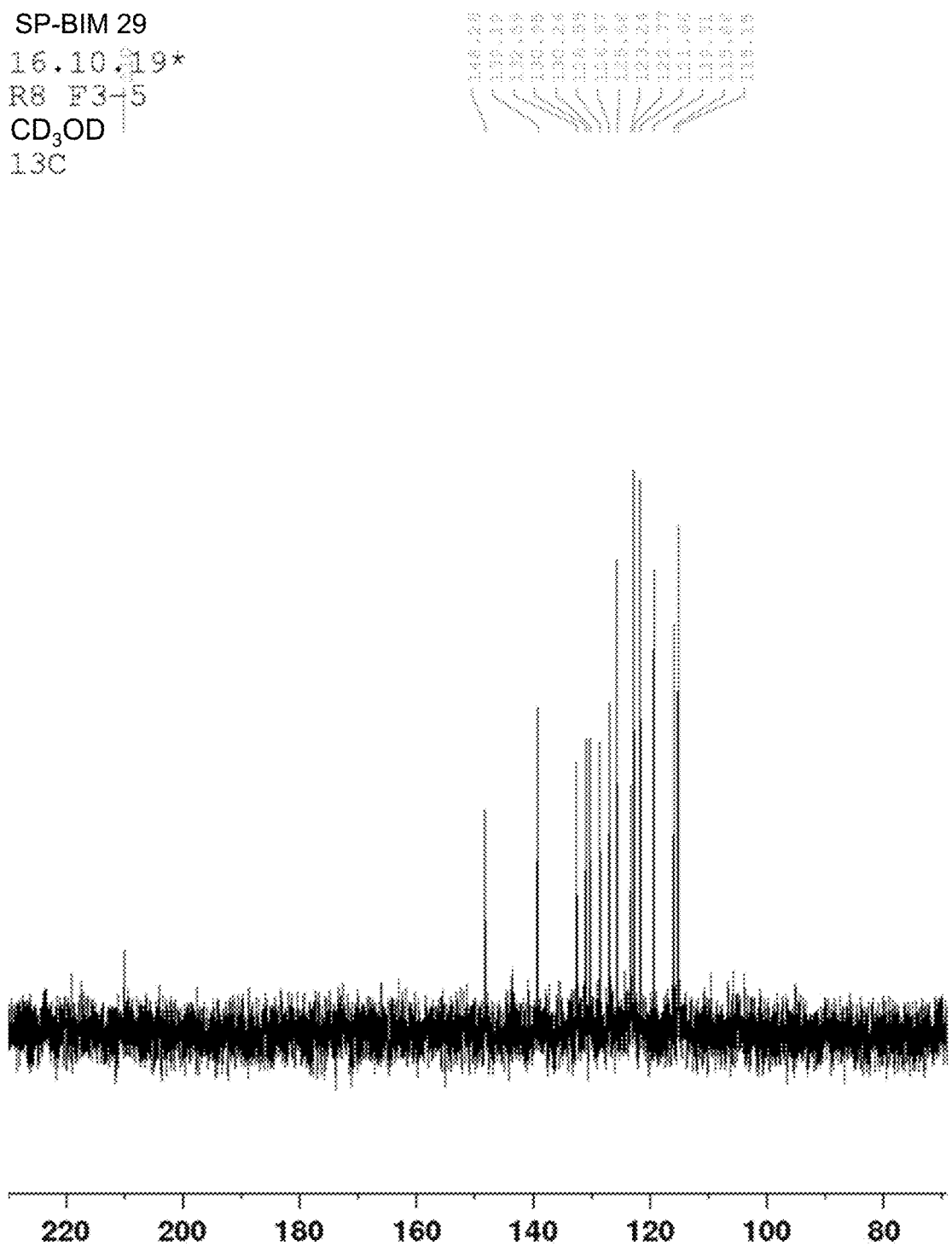
FIG. 9B depicts the $^{13}$C NMR spectrum of SP-BIM 29 taken in CD$_3$OD, according to one or more embodiments.
Figure 4B:
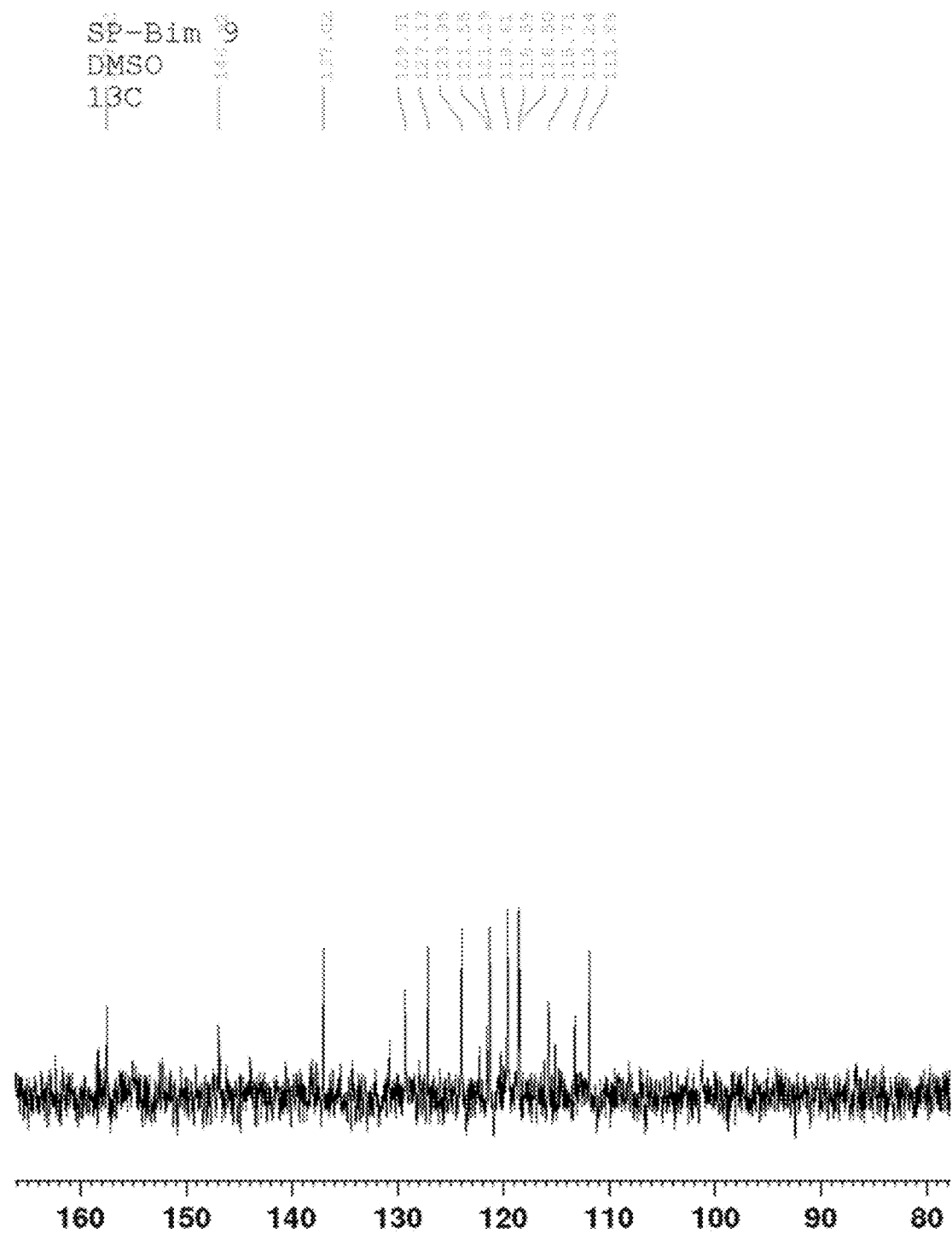
Figure 9B:
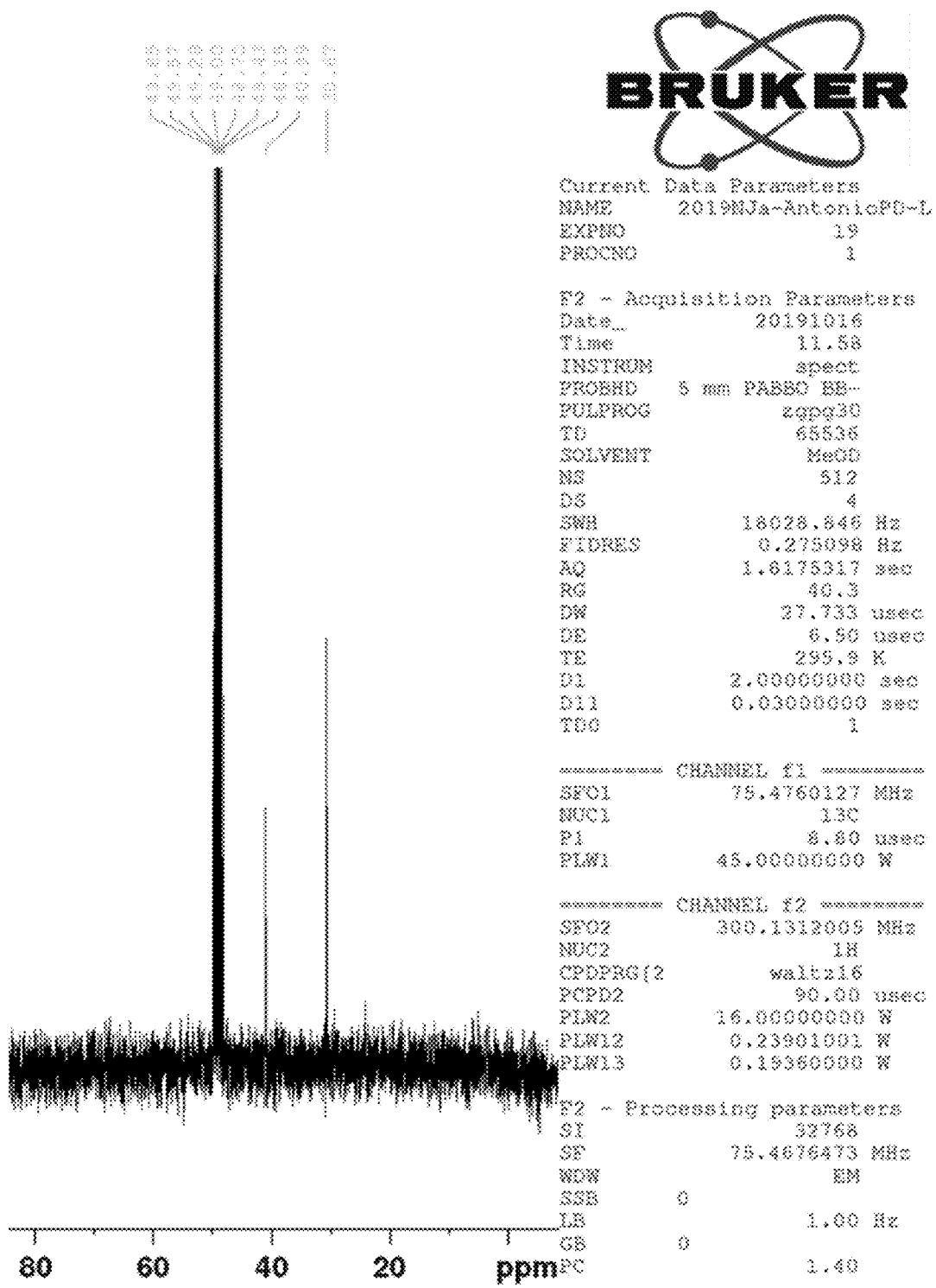

The following are definitions of terms used in the present specification. The initial definition provided for a group or term herein applies to that group or term throughout the present specification individually or as part of another group, unless otherwise indicated.

The terms "alkyl" and "alk" refer to a straight or branched chain alkane (hydrocarbon) radical containing from 1 to 12 carbon atoms, preferably from 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "($C_1$-$C_4$) alkyl" refers to a straight or branched chain alkane (hydrocarbon) radical containing from 1 to 4 carbon atoms, such as methyl, ethyl, propyl, isopropyl, n-butyl, t-butyl, and isobutyl. The term "($C_1$-$C_6$)alkyl" refers to a straight or branched chain alkane (hydrocarbon) radical containing from 1 to 6 carbon atoms, such as n-hexyl, 2-methylpentyl, 3-methylpentyl, 4-methylpentyl, 2,3-dimethylbutyl, 2,2-dimethylbutyl, in addition to those exemplified for "($C_1$-$C_4$) alkyl." "Substituted alkyl" refers to an alkyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_c$, $S(=O)_2R_c$, $P(=O)_2R_c$, $S(=O)_2OR_c$, $P(=O)_2OR_c$, $NR_bR_c$, $NR_bS(=O)_2R_c$, $NR_bP(=O)_2R_c$, $S(=O)_2NR_b R_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle, and aryl can themselves be optionally substituted.

The term "alkenyl" refers to a straight or branched chain hydrocarbon radical containing from 2 to 12 carbon atoms and at least one carbon-carbon double bond. Examples of such groups include, but are not limited to, ethenyl or allyl.

The term "$C_2$-$C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methyl(E)-but-2-enyl, 2-methy(Z)-but-2-enyl, 2,3-dimethy-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "alkynyl" refers to a straight or branched chain hydrocarbon radical containing from 2 to 12 carbon atoms and at least one carbon-carbon triple bond. An example of such groups includes, but is not limited to, ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, and hex-3-ynyl. "Substituted alkynyl" refers to an alkynyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "cycloalkyl" refers to a fully saturated cyclic hydrocarbon group containing from 1 to 4 rings and from 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_c$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently H, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "cycloalkenyl" refers to a partially unsaturated cyclic hydrocarbon group containing from 1 to 4 rings and from 3 to 8 carbons per ring. Examples of such groups include, but are not limited to, cyclobutenyl, cyclopentenyl, cyclohexenyl, etc. "Substituted cycloalkenyl" refers to a cycloalkenyl group substituted with one more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_c$, $S(=O)_2R_c$, $P(=O)_2R_c$, $S(=O)_2OR_c$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently H, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "aryl" refers to cyclic, aromatic hydrocarbon groups that have from 1 to 5 aromatic rings, especially monocyclic or bicyclic groups such as phenyl, biphenyl, or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably from 1 to 3 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_e$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, fused cyclic groups, especially fused cycloalkyl, fused cycloalkenyl, fused heterocycle, or fused aryl, where the aforementioned cycloalkyl, cycloalkenyl, heterocycle, and aryl substituents can themselves be optionally substituted.

The terms "heterocycle" and "heterocyclic" refer to fully saturated, or partially or fully unsaturated, including aromatic (i.e., "heteroaryl") cyclic groups (e.g., 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms, and/or sulfur atoms, where the nitrogen and sulfur heteroatoms may optionally be oxidized and the nitrogen heteroatoms may optionally be quaternized. The term "heteroarylium" refers to a heteroaryl group bearing a quaternary nitrogen atom and, thus, a positive charge. The heterocyclic group may be attached to the remainder of the molecule at any heteroatom or carbon atom of the ring or ring system. Exemplary monocyclic heterocyclic groups include, but are not limited to, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl, and the like. Exemplary tricyclic heterocyclic groups include, but are not limited to, carbazolyl, benzidolyl, phenanthrolinyl, acridinyl, phenanthridinyl, xanthenyl, and the like.

"Substituted heterocycle" and "substituted heterocyclic" (such as "substituted heteroaryl") refer to heterocycle or heterocyclic groups substituted with one or more substituents, preferably from 1 to 4 substituents, at any available point of attachment. Exemplary substituents include but are not limited to one or more of the following groups: H, halogen (e.g., a single halogen substituent or multiple halo substituents forming, in the latter case, groups such as $CF_3$ or an alkyl group bearing $Cl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NRdP(=O)_2NR_bR_c$, $NR_bC(=O)R_a$, or $NR_bP(=O)_2R_c$, where each occurrence of $R_a$ is independently H, alkyl, cycloalkyl, alkenyl, cycloalkenyl, alkynyl, heterocycle, or aryl; each occurrence of $R_b$, $R_c$, and $R_d$ is independently H, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include, but are not limited to, spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "alkylamino" refers to a group having the structure —NHR', where R' is H, alkyl or substituted alkyl, or cycloalkyl or substituted cycloalkyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', where R and R' are each independently alkyl or substituted alkyl, cycloalkyl or substituted cycloalkyl, cycloalkenyl or substituted cyclolalkenyl, aryl or substituted aryl, or heterocyclyl or substituted heterocyclyl, as defined herein. R and R' may be the same or different in an dialkylamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine or iodine.

Unless otherwise indicated, any heteroatom with unsatisfied valences is assumed to have hydrogen atoms sufficient to satisfy the valences.

The compounds disclosed herein may form salts which are also within the scope of this disclosure. Reference to a compound disclosed herein is understood to include reference to salts thereof, unless otherwise indicated. The term "salt(s)", as employed herein, denotes acidic and/or basic salts formed with inorganic and/or organic acids and bases. In addition, when a compound disclosed herein contains both a basic moiety, such as, but not limited to, a pyridine or imidazole, and an acidic moiety such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of a compound disclosed herein may be formed, for example, by reacting a compound of formula A, A', or B with an amount of acid or base, such as an equivalent amount, in a medium such as one in which the salt precipitates or in an aqueous medium followed by lyophilization.

The compounds disclosed herein which contain a basic moiety, such as, but not limited to, an amine or a pyridine or imidazole ring, may form salts with a variety of organic and inorganic acids. Exemplary acid addition salts include, but are not limited to, acetates (such as those formed with acetic acid or trihaloacetic acid, e.g., trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates, such as tosylates, undecanoates, and the like.

Compounds disclosed herein which contain an acidic moiety, such as, but not limited to, a carboxylic acid, may form salts with a variety of organic and inorganic bases. Exemplary basic salts include, but are not limited to, ammonium salts, alkali metal salts, such as sodium, lithium and potassium salts, alkaline earth metal salts, such as calcium and magnesium salts, salts with organic bases (e.g., organic amines), such as benzathines, dicyclohexylamines, hydrabamines (formed with N,N-bis(dehydroabietyl) ethylenediamine), N-methyl-D-glucamines, N-methyl-D-glycamides, and t-butyl amines, and salts with amino acids such as arginine, lysine, and the like. Basic nitrogen-containing groups may be quaternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), aralkyl halides (e.g., benzyl and phenethyl bromides), and others.

Prodrugs and solvates of the compounds disclosed herein are also contemplated herein. The term "prodrug" as employed herein denotes a compound that, upon administration to a subject, undergoes chemical conversion by metabolic or chemical processes to yield a compound as disclosed herein, or a salt and/or solvate thereof. Solvates of the compounds disclosed herein include, for example, hydrates.

Compounds disclosed herein, and salts or solvates thereof, may exist in their tautomeric form (for example, as an amide or imino ether). All such tautomeric forms are contemplated herein as part of the present disclosure.

All stereoisomers of the present compounds (for example, those which may exist due to asymmetric carbons on various substituents), including enantiomeric forms and diastereomeric forms, are contemplated within the scope of this disclosure. Individual stereoisomers of the compounds disclosed herein may, for example, be substantially free of other isomers (e.g., as a pure or substantially pure optical isomer having a specified activity), or may be admixed, for example, as racemates or with all other, or other selected, stereoisomers. The chiral centers of the compounds disclosed herein may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives, or separation by chiral column chromatography. The individual optical isomers can be obtained from the racemates by any suitable method, including, without limitation, conventional methods, such as, for example, salt formation with an optically active acid followed by crystallization.

Compounds disclosed herein are, subsequent to their preparation, preferably isolated and purified to obtain a composition containing an amount by weight equal to or greater than 90%, for example, equal to greater than 95%, equal to or greater than 99% pure ("substantially pure" compound of formula A, A', or B which is then used or formulated as described herein). Such "substantially pure" compounds as disclosed herein are also contemplated herein as part of the present disclosure.

All configurational isomers of the compounds disclosed herein are contemplated, either in admixture or in pure or substantially pure form. The definition of compounds disclosed herein embraces both cis (Z) and trans (E) alkene isomers, as well as cis and trans isomers of cyclic hydrocarbon or heterocyclic rings.

Throughout the specifications, groups, and substituents thereof may be chosen to provide stable moieties and compounds.

Definitions of specific functional groups and chemical terms are described in more detail below. For purposes of this disclosure, the chemical elements are identified in accordance with the Periodic Table of the Elements, CAS Version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Sorrell T, Organic Chemistry, University Science Books, Sausalito, CA: 1999, the entire contents of which are incorporated herein by reference.

Certain compounds of the present disclosure may exist in particular geometric or stereoisomeric forms. The present disclosure contemplates all such compounds, including cis- and trans-isomers, R- and S-enantiomers and diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present disclosure. Those of ordinary skill in the art will readily appreciate that analogous ratios are contemplated for more complex isomer mixtures.

The compounds disclosed herein also include isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds as disclosed herein include isotopes of hydrogen, carbon, nitrogen, oxygen, phosphorous, sulfur, fluorine, and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds disclosed herein, or an enantiomer, diastereomer, tautomer, or pharmaceutically acceptable salt or solvate thereof, which contain the aforementioned isotopes and/or other isotopes of other atoms are within the scope of this disclosure. Certain isotopically labeled compounds of the present disclosure, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this disclosure, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. For purposes of this disclosure, heteroatoms such as nitrogen may have hydrogen substituents and/or any permissible substituents of organic compounds described herein which satisfy the valences of the heteroatoms. Furthermore, this disclosure is not intended to be limited in any manner by the permissible substituents of organic compounds. Combinations of substituents and variables envisioned by this disclosure are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "microorganism" or "microbe" as used herein includes, but is not limited to, bacteria, fungi, protozoa, yeast, mold, and mildew. The term "antimicrobial agent" as used herein refers to, but is not limited to, compounds capable of inhibiting, reducing or preventing growth of a microorganism, capable of inhibiting or reducing ability of a microorganism to produce infection in a host, or capable of inhibiting or reducing ability of a microorganism to multiply or remain infective in the environment. The term "antimicrobial agent" also refers to compounds capable of decreasing infectivity or virulence of a microorganism. In some embodiments, antimicrobial agent as used herein includes, but is not limited to, antibiotic agent, antibacterial agent, and antifungal agent.

In some embodiments, the terms "antibacterial agent" or "antibiotic agent" as used herein refers to compounds capable of inhibiting, reducing, or preventing growth of bacteria, capable of inhibiting or reducing ability of bacteria to produce infection in a host, or capable of inhibiting or reducing ability of bacteria to multiply or remain infective in the environment. The term "antibacterial agent" also refers to compounds capable of decreasing infectivity or virulence of bacteria.

In some embodiments, the term "antifungal agent" as used herein refers to compounds capable of inhibiting, reducing, or preventing growth of fungi, capable of inhibiting or reducing ability of fungi to produce infection in a host, or capable of inhibiting or reducing ability of fungi to grow or remain infective in the environment. The term "antifungal agent" also refers to compounds capable of decreasing infectivity of fungi.

In some embodiments, the term "growth" as used herein refers to the growth of microorganisms and includes reproduction or population expansion of the microorganism. The term also includes maintenance of on-going metabolic processes of a microorganism, including processes that keep the microorganism alive.

In some embodiments, the term "synergistic" or "synergy" as used herein refers to the interaction of two or more agents so that their combined effect is greater than their individual effects. In some embodiments, the term "potentiator" refer to a compound that, when co-administered with an antimicrobial agent, results in the overall increase of the anti-microbial activities. In some embodiments, the resulting anti-microbial activities are more potent, or significantly more potent, than the combined anti-microbial activities of the potentiator and the antimicrobial agent when administered separately. In some embodiments, the terms potentiator and adjuvant are used interchangeably.

Compounds

In some embodiments, compounds having the indole core form the base of a wide variety of natural and synthetic molecules with a plethora of biological activities. In particular bis(indolyl)methanes (BIMs) have been shown to possess antibacterial, antifungal, anti-HIV, and antitumor activities. BIMs are a large group of alkaloids with two indol-3-yl groups bridged by a single carbon. Naturally, BIMs are found in many marine and terrestrial organisms, though scientists have devised several methods of synthesizing BIM derivatives through facile, one-pot techniques.

In some embodiments, the compounds disclosed herein are antimicrobial adjuvants or potentiators.

In one aspect, the present disclosure provides a compound having Formula A or B,

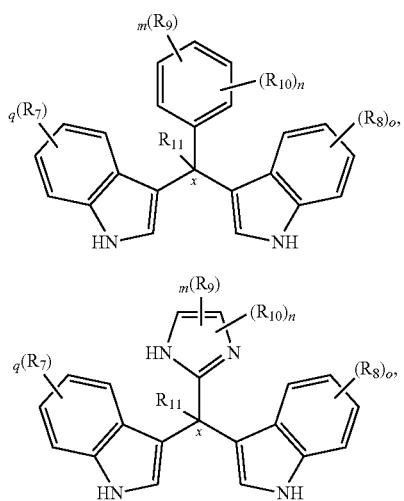

where
each occurrence of $R_9$ is independently selected from the group consisting of $NH_2$, OH, CHO, $NO_2$, halogen, and ($C_1$ to $C_6$)alkyl optionally substituted with one or more of halogen, OH, $NH_2$, $NO_2$, or CHO; and where $R_9$ is substituted on the phenyl ring of Formula A or the imidazole ring of Formula B;

m is 0 to 5;

each occurrence of $R_{10}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, $(CH_2)_p$ ($C_1$ to $C_6$)haloalkyl, or CH(indole)$_2$, in which said heterocycle includes at least one heteroatom selected from the group consisting of nitrogen, oxygen, and sulfur and may be optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy, or alternatively two $R_{10}$ taken together with the ring atoms that they are connected to form a 4-7-membered aromatic ring; where $R_{10}$ is substituted on the indole ring and/or the phenyl ring of Formula A or on the imidazole ring of Formula B;

each of n, o, p, and q is independently an integer from 0 to 4;

$R_7$ and $R_8$ are each independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, or $(CH_2)_p$ ($C_1$ to $C_6$)haloalkyl, in which said heterocycle contains at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy;

$R_a$ and $R_b$ are each independently H, ($C_1$ to $C_6$)alkyl, ($C_2$ to $C_6$)alkenyl, or ($C_3$ to $C_7$)cycloalkyl;

each occurrence of $R_{11}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, or $(CH_2)_pNR_aR_b$, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy;

$R_a$ and $R_b$ are each independently H, ($C_1$ to $C_6$)alkyl, ($C_2$ to $C_6$)alkenyl, or ($C_3$ to $C_7$) cycloalkyl; and x is optionally present, where x is a positive charge.

In another aspect, the present disclosure provides a pharmaceutical composition, including an antimicrobial agent and a compound having Formula A or B,

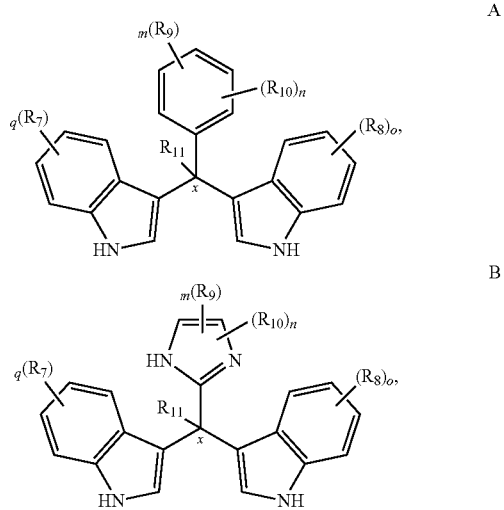

where
each occurrence of $R_9$ is independently selected from the group consisting of $NH_2$, $NO_2$, OH, CHO, halogen, and $C_1$ to $C_6$ alkyl optionally substituted with one or more of halogen, OH, $NH_2$, $NO_2$, or CHO; and where $R_9$ is substituted on the phenyl ring of Formula A or the imidazole ring of Formula B;

m is 0 to 5;

each occurrence of $R_{10}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, $(CH_2)_p$ ($C_1$ to $C_6$)haloalkyl, or $CH(indole)_2$, in which said heterocycle includes at least one heteroatom selected from the group consisting of nitrogen, oxygen, and sulfur and may be optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy, or alternatively two $R_{10}$ taken together with the ring atoms that they are connected to form a 4-7-membered aromatic ring; where $R_{10}$ is a group substituted on the indole ring and/or the phenyl ring of Formula A or on the indole ring and/or the imidazole ring of Formula B;

each of n, o, p, and q is independently an integer from 0 to 4; $R_7$ and $R_8$ are each independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, or $(CH_2)_p$ ($C_1$ to $C_6$)haloalkyl, in which said heterocycle contains at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy;

each occurrence of $R_{11}$ is independently H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, 3-7-membered heterocycle, ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, or $(CH_2)_pNR_aR_b$, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl and ($C_1$ to $C_4$)alkoxy;

$R_a$ and $R_b$ are each independently H, ($C_1$ to $C_6$)alkyl, ($C_2$ to $C_6$)alkenyl, or ($C_3$ to $C_7$) cycloalkyl; and x is optionally present, where x is a positive charge.

In certain embodiments, $R_7$ and $R_8$ are each independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, or ($C_3$ to $C_7$)cycloalkyl. In certain embodiments, $R_7$ and $R_8$ are each independently ($C_1$ to $C_6$)alkylthio, $NR_aR_b$, ($C_1$ to $C_6$)haloalkyl, $(CH_2)_p$($C_3$ to $C_7$)cycloalkyl, $(CH_2)_pOR_a$, $(CH_2)_pSR_a$, $(CH_2)_pNR_aR_b$, or $(CH_2)_p$($C_1$ to $C_6$)haloalkyl. In other embodiments, $R_7$ and $R_8$ are each independently 3 to 7-membered heterocycle optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy.

In certain embodiments, $R_7$ and $R_8$ are each independently $OCH_3$ or ($C_2$ to $C_6$)alkoxy. In certain embodiments, $R_7$ and $R_8$ are $OCH_3$. In certain embodiments, $R_7$ and $R_8$ are each independently H or ($C_1$ to $C_6$)alkyl. In certain embodiments, $R_7$ and $R_8$ are H.

In certain embodiments, $R_7$ and $R_8$ are independently Br or OH.

In certain embodiments, $R_7$ and $R_8$ are Br.

In certain embodiments, $R_7$ and $R_8$ are OH.

In certain embodiments, the compound has the structure of formula A':

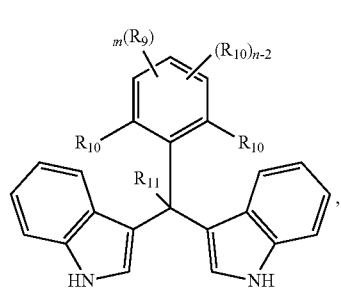

where the various substituents are as defined herein.

In certain embodiments, the compound has the structure of formula A":

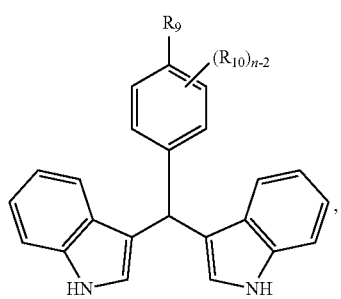

where the various substituents are as defined herein. In certain embodiments, the compound has the structure of formula A''':

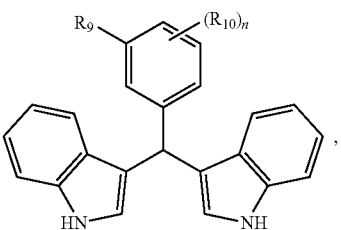

where the various substituents are as defined herein.

In certain embodiments, the compound has the structure of formula A1:

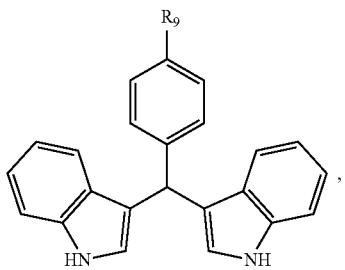

A1 where the various substituents are as defined herein.

In certain embodiments, the compound has the structure of formula A2:

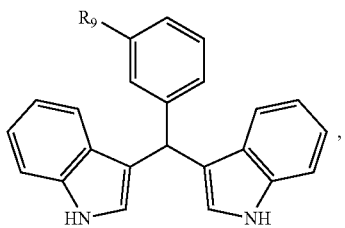

A2 where the various substituents are as defined herein.

In certain embodiments, at least one $R_9$ is selected from the group consisting of $NH_2$, OH, CHO, and halogen. In certain embodiments, at least one $R_9$ is halogen or ($C_1$ to $C_6$)alkyl substituted with one or more of halogen. In certain embodiments, at least one $R_9$ is halogen. In certain embodiments, at least one $R_9$ is Cl or Br. In certain embodiments, at least one $R_9$ is F.

In certain embodiments, at least one $R_9$ is $NH_2$ or ($C_1$ to $C_6$)alkyl substituted with one or more of $NH_2$. In certain embodiments, at least one $R_9$ is $NH_2$. In certain embodiments, at least one $R_9$ is $NO_2$. In certain embodiments, at least one $R_9$ is CHO or ($C_1$ to $C_6$)alkyl substituted with one or more of CHO. In certain embodiments, at least one $R_9$ is OH or ($C_1$ to $C_6$)alkyl substituted with one or more of OH. In certain embodiments, at least one $R_9$ is OH.

In certain embodiments, each $R_9$ is independently selected from the group consisting of $CH_3$, OH, $NH_2$, $NO_2$, CHO, and $C(CH_3)_3$.

In certain embodiments, each $R_{10}$ is independently selected from the group consisting of halogen, $CH_3$, $N(CH_3)_2$, $NO_2$, CHO, OH, $OCH_3$, $NH_2$, $C(CH_3)_3$, and

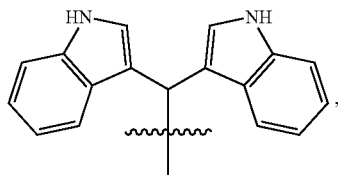 [SMILES: *C(c1c[nH]c2ccccc12)c1c[nH]c2ccccc12]

or where two $R_{10}$ taken together with the ring atoms they are connected to form a 6-membered aromatic ring.

In certain embodiments, each occurrence of $R_{10}$ is independently H, halogen, OH, CN, $OCF_3$, ($C_1$ to $C_6$)alkyl, ($C_2$ to $C_6$)alkenyl, ($C_2$ to $C_6$)alkynyl, ($C_1$ to $C_6$)alkoxy, or ($C_3$ to $C_7$)cycloalkyl. In certain embodiments, each occurrence of $R_{10}$ is independently 3-7-membered heterocycle, ($C_1$ to $C_6$)alkylthio, $NR_aR_b$, ($C_1$ to $C_6$)haloalkyl, $(CH_2)_p(C_3$ to $C_7$)cycloalkyl, $(CH_2)_pOR_a$, $(CH_2)_pSR_a$, $(CH_2)_pNR_aR_b$, or $(CH_2)_p(C_1$ to $C_6$)haloalkyl. In certain embodiments, each occurrence of $R_{10}$ is H. In certain embodiments, each occurrence of $R_{10}$ is independently H. In certain embodiments, each occurrence of $R_{10}$ is independently F. In certain embodiments, each occurrence of $R_{10}$ is independently Cl. In certain embodiments, each occurrence of $R_{10}$ is independently Br. In certain embodiments, each occurrence of $R_{10}$ is independently OH. In certain embodiments, each occurrence of $R_{10}$ is independently $NH_2$.

In some embodiments, $R_{11}$ is H, halogen, OH, CN, $NO_2$, $OCF_3$, ($C_1$ to $C_6$)alkyl, ($C_2$ to $C_6$)alkenyl, ($C_2$ to $C_6$)alkynyl, ($C_1$ to $C_6$)alkoxy, ($C_3$ to $C_7$)cycloalkyl, $(CH_2)_p$(3-7-membered heterocycle), ($C_1$ to $C_6$)alkylthio, $NR_aR_b$, ($C_1$ to $C_6$)haloalkyl, $(CH_2)_p(C_3$ to $C_7$)cycloalkyl, $(CH_2)_pOR_a$, $(CH_2)_pSR_a$, $(CH_2)_pNR_aR_b$, or $(CH_2)_p(C_1$ to $C_6$)haloalkyl, in which said heterocycle includes at least one heteroatom selected from the group consisting of nitrogen, oxygen and sulfur and may be optionally substituted by from one to three groups which may be the same or different selected from the group consisting of halogen, OH, CN, ($C_1$ to $C_4$)alkyl, ($C_1$ to $C_4$)haloalkyl, and ($C_1$ to $C_4$)alkoxy.

In some embodiments, $R_{11}$ is ($C_1$ to $C_6$)alkyl, ($C_1$ to $C_6$)alkoxy, or OH. In some embodiments, $R_{11}$ is methyl, ethyl, propyl, or butyl. In certain embodiments, $R_{11}$ is methyl. In certain embodiments, $R_{11}$ is ethyl. In certain embodiments, $R_{11}$ is methyl. In certain embodiments, $R_{11}$ is n-propyl or iso-propyl. In some embodiments, $R_{11}$ is OH, $OCH_3$, $OCH_2CH_3$, or $O(CH_2)_2CH_3$. In certain embodiments, $R_{11}$ is OH. In certain embodiments, Rn is $OCH_3$.

In certain embodiments, $R_a$ and $R_b$ are each independently H, $C_1$ to $C_6$ alkyl, $C_2$ to $C_6$ alkenyl, or $C_3$ to $C_7$ cycloalkyl. In certain embodiments, at least one of $R_a$ and $R_b$ is H. In certain embodiments, at least one of $R_a$ and $R_b$ is Me, Et, or propyl. In certain embodiments, at least one of $R_a$ and $R_b$ is cyclopropyl or cyclobutyl. In certain embodiments, both $R_a$ and $R_b$ are H.

In certain embodiments, o is 0, 1, 2, 3, or 4. In certain embodiments, o is 0. In certain embodiments, o is 1. In certain embodiments, o is 2. In certain embodiments, o is 3. In certain embodiments, o is 4. In certain embodiments, o and q are each independently 0, 1 or 2. In certain embodiments, o and q are 0. In certain embodiments, m is 0. In certain embodiments, m is 1, 2, or 3. In certain embodiments, m is 1. In certain embodiments, m is 2. In certain embodiments, n is 1 or 2. In certain embodiments, n is 3 or 4. In certain embodiments, n is 0. In certain embodiments, q is 0, 1, 2, 3, or 4. In certain embodiments, q is 0. In certain embodiments, q is 1. In certain embodiments, q is 2. In certain embodiments, q is 3. In certain embodiments, q is 4. In certain embodiments, p is 0, 1, 2, 3, or 4. In certain embodiments, p is 0. In certain embodiments, p is 1. In certain embodiments, p is 2. In certain embodiments, p is 3. In certain embodiments, p is 4.

In certain embodiments, x is not present and the compound as disclosed is neutral. In certain embodiments, x is present as a positive charge and the compound as disclosed further includes a counterion. In certain embodiments, the counterion is an organic or inorganic anion. In certain embodiments, the counterion is $F^-$, $Cl^-$, $Br^-$, $I^-$, $HCO_3^-$, and $CF_3COO^-$, and $CF_3O_3S^-$.

In certain embodiments, the present disclosure provides a compound selected from the group consisting of

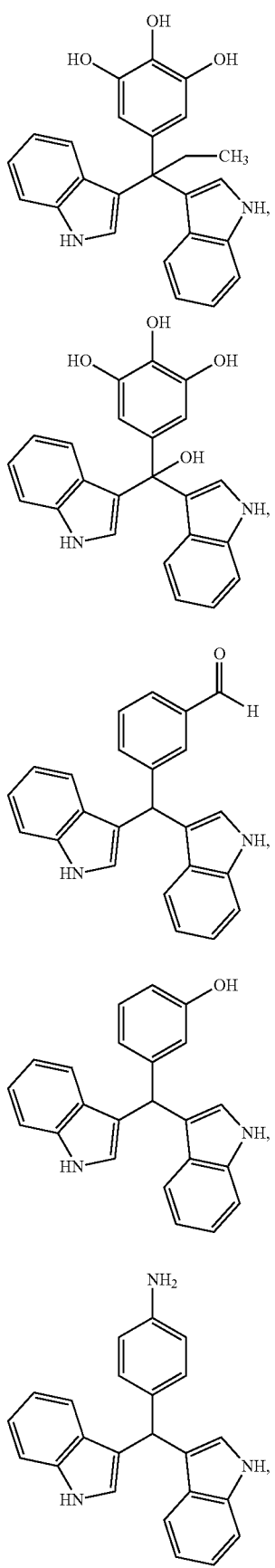
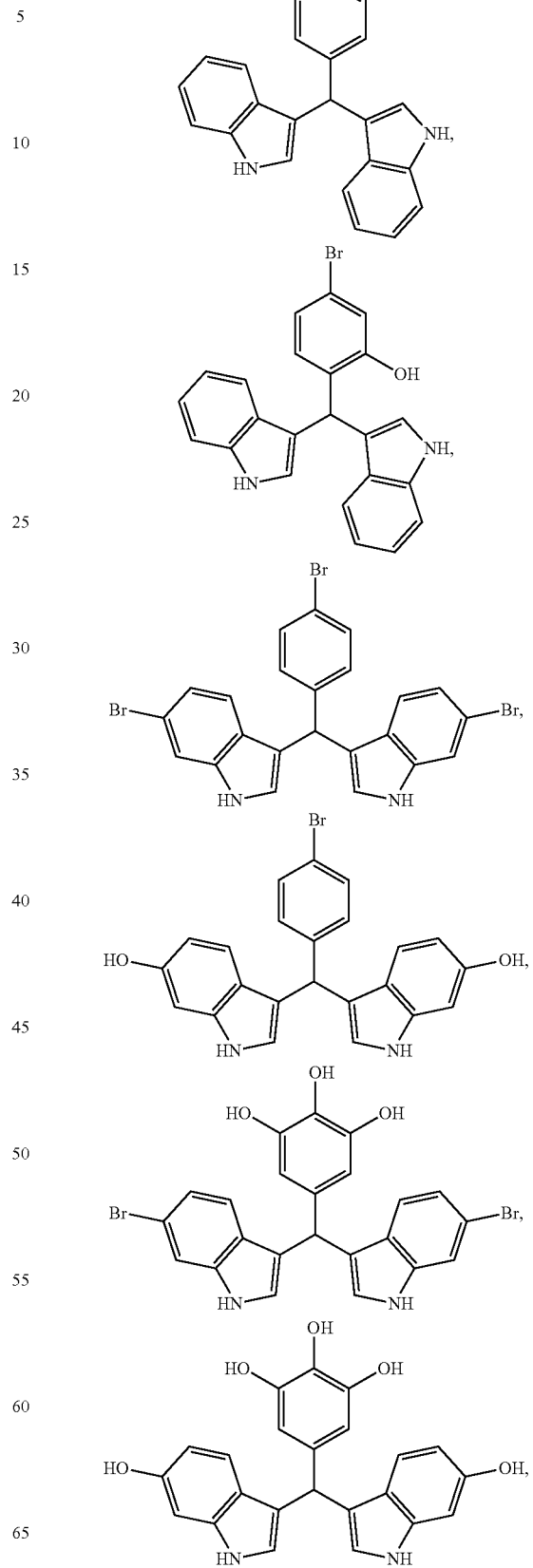

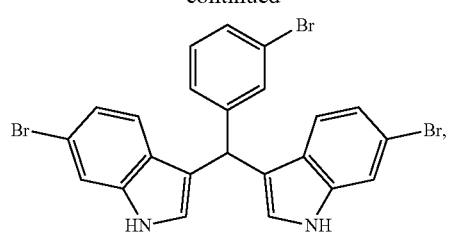
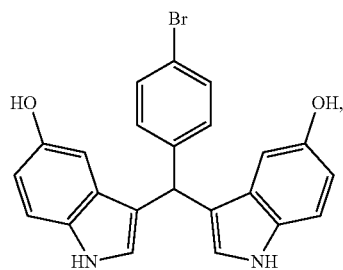
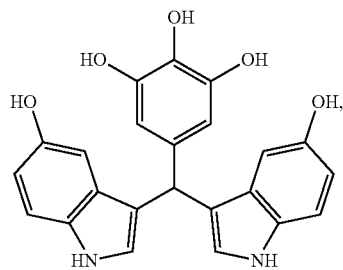
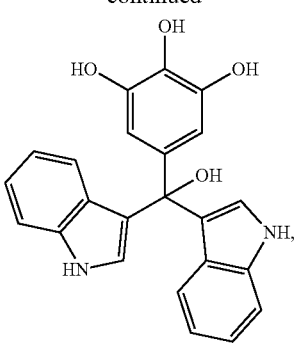
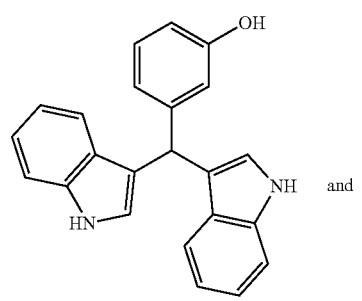
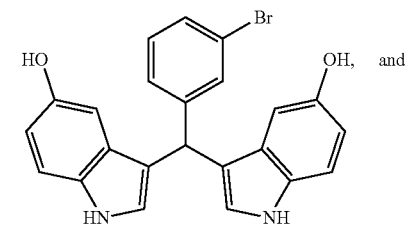
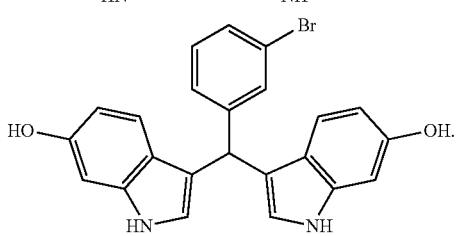
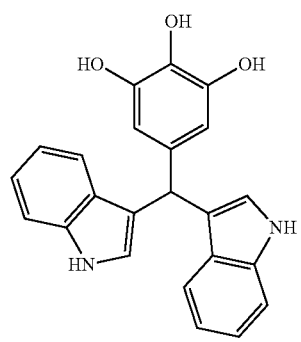
In certain embodiments, the present disclosure provides a compound selected from the group consisting of
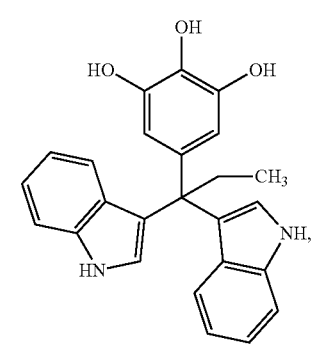
In certain embodiments, the present disclosure provides a compound of Formula:
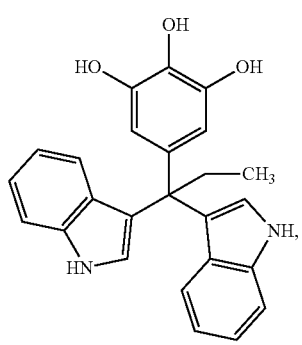

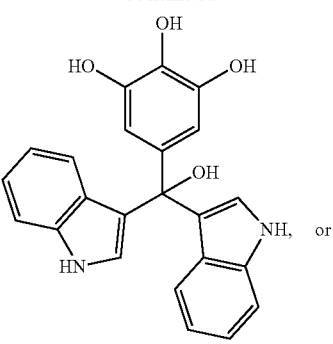

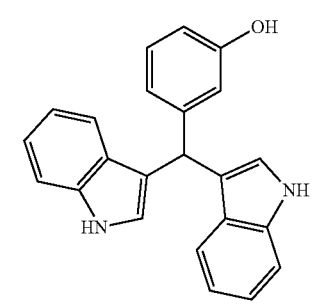

In certain embodiments, the present disclosure provides a compound of Formula:

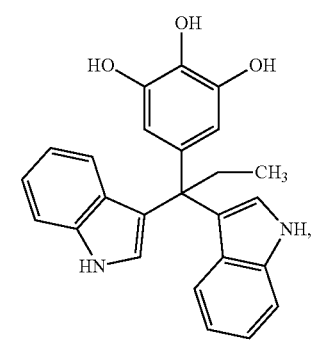

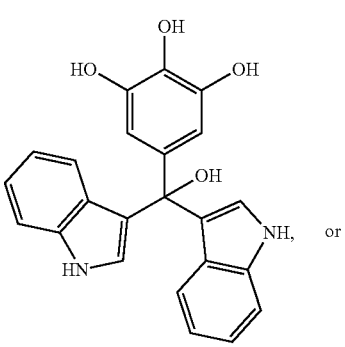

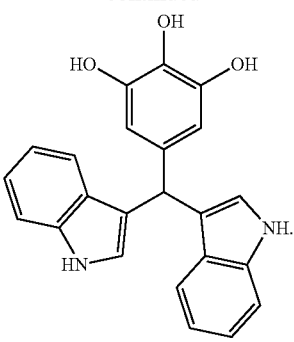

In another aspect, the present disclosure provides a pharmaceutical composition including compounds as described herein and pharmaceutically acceptable excipients. In some embodiments, the pharmaceutical composition further includes an antimicrobial agent. In certain embodiments, the antimicrobial agent is an antibacterial agent.

In some embodiments, the antimicrobial agent is an antifungal agent. In some embodiments, the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In certain embodiments, the present disclosure provides a pharmaceutical composition as described herein, where the antimicrobial agent is selected from the group of ampicillin, imipenem, cephalexin, erythromycin, aztreonam, trimethoprim, streptomycin, ciprofloxacin, vancomycin, doxycycline, and kanamycin.

In certain embodiments, the present disclosure provides a pharmaceutical composition as described herein, including

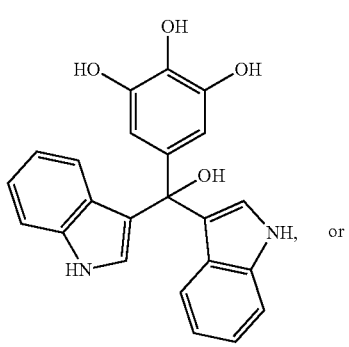

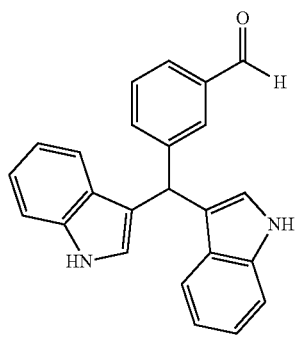

and an antimicrobial agent selected from the group consisting of ampicillin, imipenem, cephalexin, erythromycin, streptomycin, vancomycin, doxycycline, and kanamycin.

In certain embodiments, the present disclosure provides a pharmaceutical composition as described herein, including

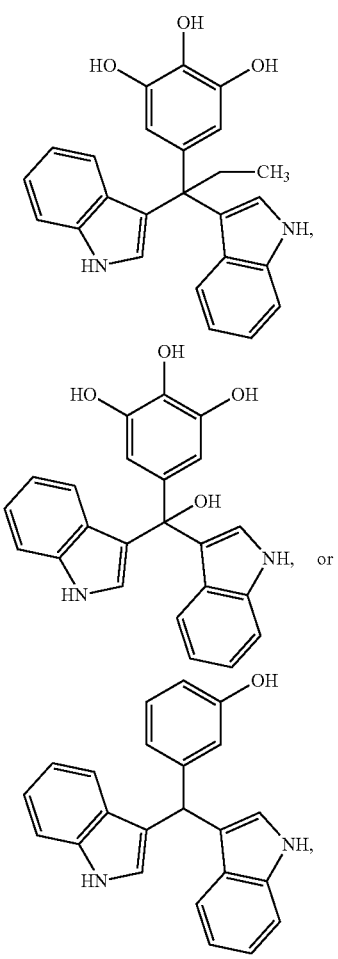

and an antimicrobial agent selected from the group consisting of ampicillin, imipenem, cephalexin, aztreonam, trimethoprim, streptomycin, ciprofloxacin, vancomycin, doxycycline, and kanamycin.

In certain embodiments, the present disclosure provides a pharmaceutical composition as described herein, including

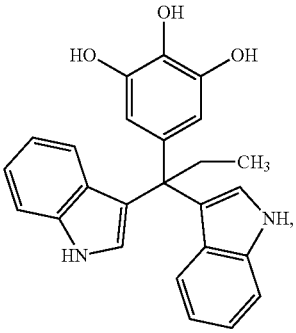

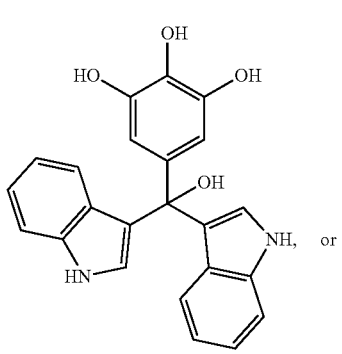

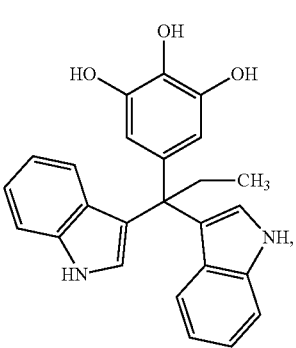

and an antimicrobial agent selected from the group of ampicillin, imipenem, cephalexin, erythromycin, aztreonam, trimethoprim, streptomycin, ciprofloxacin, vancomycin, doxycycline, and kanamycin.

In certain embodiments, the present disclosure provides a pharmaceutical composition as described herein, including -continued

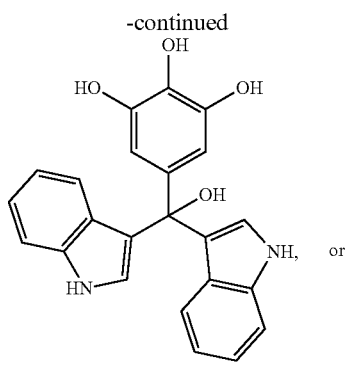

or

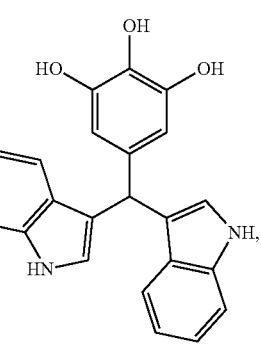

and an antimicrobial agent selected from the group of ampicillin, imipenem, cephalexin, erythromycin, aztreonam, trimethoprim, streptomycin, ciprofloxacin, vancomycin, doxycycline, and kanamycin.

In certain embodiments, the present disclosure provides a pharmaceutical composition as described herein, including

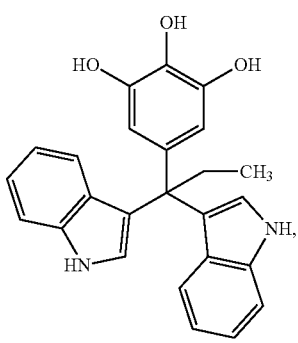

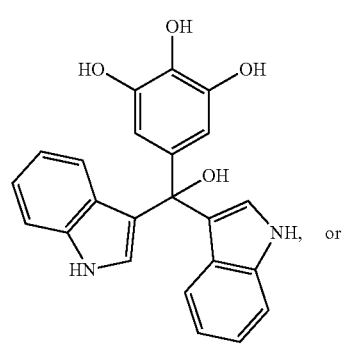

or

-continued

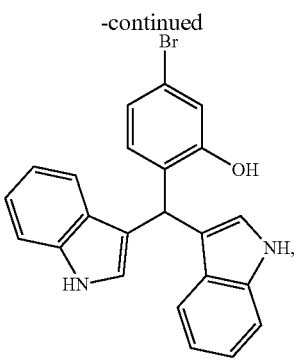

and an antimicrobial agent selected from the group of ampicillin, imipenem, cephalexin, aztreonam, trimethoprim, streptomycin, ciprofloxacin, vancomycin, doxycycline, and kanamycin.

Utility and Methods of Use

In another aspect, the present disclosure provides a method of treating, preventing, or reducing the risk of a microbial infection in a patient, the method including administering a compound of Formula A or B described herein, or a pharmaceutical composition thereof. In another aspect, the present disclosure provides a method of treating, preventing, or reducing the risk of a microbial infection in a patient, the method including administering an antimicrobial agent and a compound of Formula A or B described herein.

In another aspect, the present disclosure provides a method of treating, preventing, or reducing the risk of a microbial infection in a patient, the method including administering the pharmaceutical composition described herein.

In certain embodiments, the method includes treating, preventing, or reducing the risk of biofilms, hemotoxicity, and/or virulence of a microbial infection.

In certain embodiments, the microbial infection includes one or more bacteria, yeast, fungi, or combinations thereof. In certain embodiments, the microbial infection includes one or more bacteria. In certain embodiments, the microbial infection includes one or more yeast. In certain embodiments, the microbial infection includes one or more fungi.

In certain embodiments, the administration is performed once daily.

In certain embodiments, the microbes are clinically antibiotic resistant.

In certain embodiments, the microbes form biofilms.

In another aspect, the present disclosure provides a method of inhibiting or extinguishing the growth of one or more microbial cultures in vitro, the method including administering an antimicrobial agent and a compound as described herein.

In a further another aspect, the present disclosure provides a method of inhibiting or extinguishing the growth, virulence, or hemotoxicity of one or more microbial cultures in vitro, the method including administering an antimicrobial agent and a compound or the pharmaceutical composition as described herein.

In a further another aspect, the present disclosure provides a method of reducing the expression of bacterial genes promoting resistance of the bacterial cells to antibiotics, the method including administering a compound or the pharmaceutical composition as described herein.

In some embodiments, the present disclosure provides a method of reducing the expression of bacterial genes promoting virulence of the bacterial cells and their resistance to antibiotics as described herein, the method including administering a compound or the pharmaceutical composition as described herein, where an antimicrobial agent is also administered to the bacterial cells.

In some embodiments, the bacterial genes promoting virulence of the bacterial cells and their resistance to antibiotics include mecA, blaZ, and fnbA.

In a further another aspect, the present disclosure provides a method of reducing of global regulator genes in bacterial cells, the method including administering a compound or the pharmaceutical composition as described herein.

In some embodiments, an antimicrobial agent is also administered to the bacterial cells.

In some embodiments, the global regulator genes include sarA, agrA, and RNA III.

In certain embodiments, the present disclosure provides a method as described herein, where the antimicrobial agent is a macrolide, a folic acid synthesis inhibitor, a fluoroquinolone, an aminoglycoside, a monobactam, a cephalosporin, a glycopeptide, a β-lactam, a carbapenem, or a tetracycline.

In certain embodiments, the present disclosure provides a method as described herein, where the antimicrobial agent is selected from the group consisting of erythromycin, trimethoprim, ciprofloxacin, streptomycin, aztreonam, cefalexin, vancomycin, ampicillin, doxycycline, and kanamycin.

In certain embodiments, the present disclosure provides a method as described herein, where the antimicrobial agent is selected from the group of vancomycin and ampicillin.

In certain embodiments, the microbe is Gram-positive bacteria.

In certain embodiments, the microbe is Gram-negative bacteria.

In certain embodiments, the microbe is a mixture of both Gram-positive and Gram-negative bacteria.

In certain embodiments, the microbe is selected from the group consisting of *Bacillus cereus, Streptococcus pyogenes, Streptococcus pneumoniae, Staphylococcus aureus, Enterococcus faecium, Corynebacterium diphtheriae, Escherichia coli, Salmonella typhimurium, Pseudomonas aeruginosa, Klebsiella pneumoniae, Candida albicans*, and mixtures thereof.

In certain embodiments, the microbe is selected from the group consisting of *Staphylococcus aureus, Streptococcus pneumoniae, Klebsiella pneumoniae Escherichia coli*, and a combination thereof.

In certain embodiments, the microbe is *Staphylococcus aureus, Enterococcus faecium*, or a mixture thereof.

In certain embodiments, the microbe is *Staphylococcus aureus*.

In certain embodiments, the microbe is MRSA.

Pharmaceutical Compositions

This disclosure also provides a pharmaceutical composition including at least one of the compounds as described herein or a pharmaceutically acceptable salt thereof, optionally an antibiotic agent, and a pharmaceutically acceptable carrier.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as butylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present pharmaceutical agents may be provided in the form of pharmaceutically acceptable salts. The term "pharmaceutically-acceptable salt", in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed. Representative salts include, but are not limited to, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al., (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

In other cases, the compounds of the present disclosure may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present disclosure. These salts can likewise be prepared in situ during the final isolation and purification of the compounds, or by separately reacting the purified compound in its free acid form with a suitable base, such as the hydroxide, carbonate, or bicarbonate of a pharmaceutically-acceptable metal cation, with ammonia, or with a pharmaceutically-acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like. (See, for example, Berge et al., supra)

Wetting agents, emulsifiers, and lubricants, such as sodium lauryl sulfate, magnesium stearate, and polyethylene oxide-polybutylene oxide copolymer, as well as coloring agents, release agents, coating agents, sweetening, flavoring, and perfuming agents, preservatives, and antioxidants, can also be present in the compositions.

Formulations of the present disclosure include those suitable for oral, nasal, topical (including buccal and sublingual), rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouth washes, and the like, each containing a predetermined amount of a compound of the present disclosure as an active ingredient. A compound disclosed herein may also be administered as a bolus, electuary, or paste.

In solid dosage forms of the disclosure for oral administration (capsules, tablets, pills, dragees, powders, granules, and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets, and pills, the pharmaceutical compositions may also include buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active, or dispersing agent. Molded tablets, may be, made by molding in a suitable machine a mixture of the powdered compound moistened with an inert liquid diluent.

The tablets, and other solid dosage forms of the pharmaceutical compositions of the present disclosure, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxybutylmethyl cellulose in varying butortions to provide the desired release profile, other polymer matrices, liposomes, and/or microspheres. They may be sterilized by, for example, filtration through a bacteria-retaining filter, or by incorporating sterilizing agents in the form of sterile solid compositions, which can be dissolved in sterile water, or some other sterile injectable medium, immediately before use. These compositions may also optionally contain opacifying agents and may be of a composition that they release the active ingredient(s) only, or preferentially, in a certain portion of the gastrointestinal tract, optionally, in a delayed manner. Examples are embedding compositions, which can be used include polymeric substances and waxes. The active ingredient can also be in micro-encapsulated form, if apbutriate, with one or more of the above-described excipients.

Liquid dosage forms for oral administration of the compounds disclosed herein include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Additionally, cyclodextrins, e.g., hydroxybutyl-β-cyclodextrin, may be used to solubilize compounds.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions disclosed herein for rectal or vaginal administration may be presented as a suppository, which may be prepared by mixing one or more compounds disclosed herein with one or more suitable nonirritating excipients or carriers including, for example, cocoa butter, polyethylene glycol, a suppository wax, or a salicylate, and which is solid at room temperature, but liquid at body temperature and, therefore, will melt in the rectum or vaginal cavity and release the active pharmaceutical agents disclosed herein.

Formulations disclosed herein which are suitable for vaginal administration also include pessaries, tampons, creams, gels, pastes, foams, or spray formulations containing such carriers as are known in the art to be apbutriate.

Dosage forms for the topical or transdermal administration of a compound disclosed herein include powders, sprays, ointments, pastes, creams, lotions, gels, solutions, patches, and inhalants. The active compound may be mixed under sterile conditions with a pharmaceutically acceptable carrier, and with any preservatives, buffers, or butellants which may be required.

The ointments, pastes, creams, and gels may contain, in addition to an active compound as disclosed herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound as disclosed herein, excipients such as lactose, talc, silicic acid, aluminum hydroxide, calcium silicates, and polyamide powder, or mixtures of these substances. Sprays can additionally contain customary butellants, such as chlorofluorohydrocarbons and volatile unsubstituted hydrocarbons, such as butane.

Transdermal patches have the added advantage of providing controlled delivery of a compound as disclosed herein to the body. Such dosage forms can be made by dissolving, or dispersing the pharmaceutical agents in the buter medium. Absorption enhancers can also be used to increase the flux of the pharmaceutical agents disclosed herein across the skin. The rate of such flux can be controlled, by either providing a rate controlling membrane or dispersing the compound in a polymer matrix or gel.

Ophthalmic formulations, eye ointments, powders, solutions, and the like, are also contemplated as being within the scope of this disclosure.

Pharmaceutical compositions as disclosed herein suitable for parenteral administration include one or more compounds as disclosed herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. One strategy for depot injections includes the use of polyethylene oxide-polybutylene oxide copolymers where the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds disclosed herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions disclosed herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound as disclosed herein may be administered concurrently with another anti-HCV agent), or they may achieve different effects (e.g., control of any adverse effects).

The compounds disclosed herein may be administered intravenously, intramuscularly, intraperitoneally, subcutaneously, topically, orally, or by other acceptable means. The compounds may be used to treat arthritic conditions in mammals (i.e., humans, livestock, and domestic animals), birds, lizards, and any other organism, which can tolerate the compounds.

The disclosure also provides a pharmaceutical pack or kit including one or more containers filled with one or more of the ingredients of the pharmaceutical compositions disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Methods of Synthesizing Compounds Described Herein

Due to the structure of the BIM skeleton, synthesis is accomplished using two molecules of indole and one carbonyl molecule with the use of an acid catalyst. The reaction of indole with aldehydes or ketones produces azafulvenium salts that react further with a second indole molecule to form the bis(indol-3-yl)methane. Further examples of the synthesis are described in more detail below.

EQUIVALENTS

The representative examples which follow are intended to help illustrate the disclosure, and are not intended to, nor should they be construed to, limit its scope. Indeed, various modifications of the disclosure and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification, and guidance which can be adapted to the practice of this invention in its various embodiments and equivalents thereof.

EXAMPLES

Example 1A: Substituted phenyl bis(indolyl)methanes (BIMs)

The representative substituted BIMs are listed in Table 1.

TABLE 1

Substituted phenyl bis(indolyl)methanes (BIMs) described in this application

| Indole | Aldehyde | Product | Details |
|---|---|---|---|
| 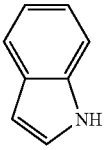 | 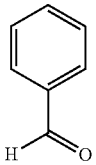 | 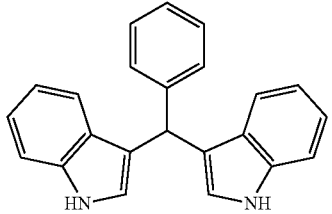
SP-BIM 1 | Name: bis(indol-3-yl)phenyl-methane
Chemical Formula: $C_{23}H_{18}N_2$
Molecular Weight: 322.41
Yield: 89%
Red amorphous solid
TLC $R_f$ (9:1 (v/v) $CHCl_3$: MeOH = 0.95 |
| 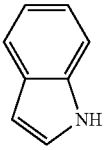 | 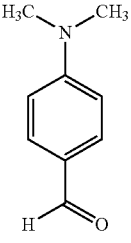 | 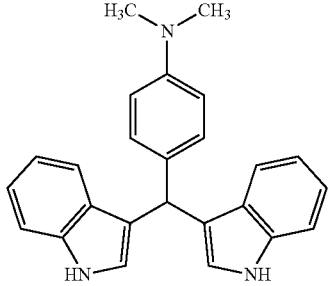
SP-BIM 2 | Name: [bis(indoly-3-yl)-4-dimethylaminophenyl]methane
Chemical Formula: $C_{25}H_{23}N_3$
Molecular Weight: 365.48
Yield: 95%
Purple amorphous solid |
| 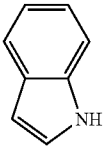 | 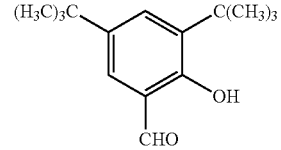 | 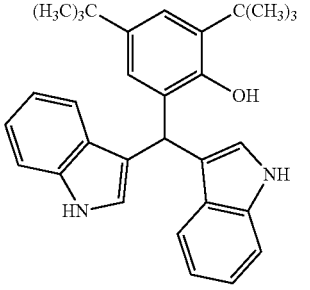
SP-BIM 3 | Name: [bis(indol-3-yl)-3,5-di-tert-butyl-2-hydroxyphenyl]-methane
Chemical Formula: $C_{31}H_{34}N_2O$
Molecular Weight: 450.63
Yield: 71% |
| 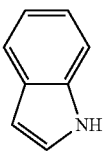 | 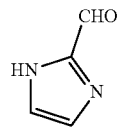 | 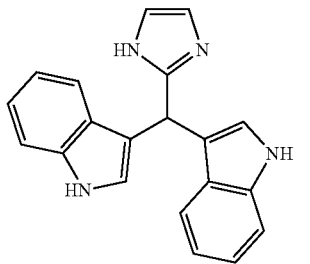
SP-BIM 4 | Name: [bis(indol-3-yl)imidazol-2-yl]methane
Chemical Formula: $C_{20}H_{16}N_4$
Molecular Weight: 312.38
Yield: 20%
White amorphous solid |

TABLE 1-continued

Substituted phenyl bis(indolyl)methanes (BIMs) described in this application

| Indole | Aldehyde | Product | Details |
|---|---|---|---|
| 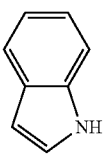 | 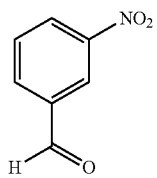 | 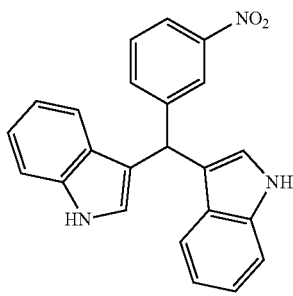<br>SP-BIM 5 | Name: [bis(indol-3-yl)-3-nitro-phenyl]methane<br>Chemical Formula: $C_{23}H_{17}N_3O_2$<br>Molecular Weight: 367.41<br>Yield: 98% |
| 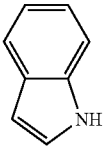 | 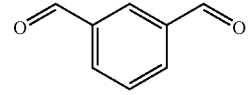 | 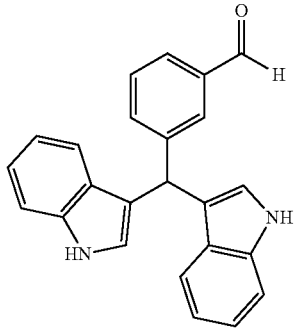<br>SP-BIM 6 | Name: [bis(indol-3-yl)-3-formylphenyl]methane<br>Chemical Formula: $C_{24}H_{18}N_2O$<br>Molecular Weight: 350.42<br>Yield: 40%<br>TLC $R_f$ ((6:4 (v/v) PE: EtOAc) = 0.05 |
| 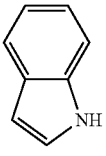 | 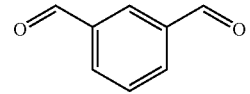 | 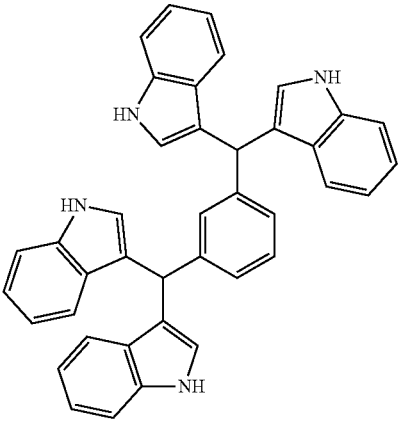<br>SP-BIM 7 | Name: 1,3-bis[bis(indoly-3-yl)-methyl]benzene<br>Chemical Formula: $C_{40}H_{30}N_4$<br>Molecular Weight: 566.71<br>Yield: 60%<br>TLC $R_f$ (6:4 (v/v) PE: EtOAc) = 0.13 |
| 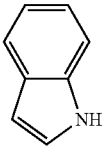 | 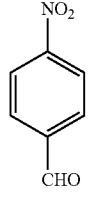 | 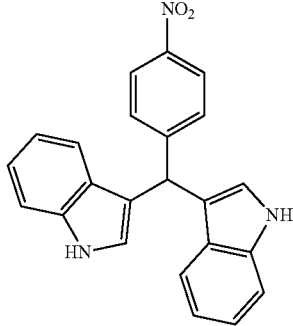<br>SP-BIM 8 | Name: bis(indol-3-yl)-4-nitro-phenyl]methane<br>Chemical Formula: $C_{23}H_{17}N_3O_2$<br>Molecular Weight: 367.41<br>Yield: 98%<br>TLC $R_f$ (3:2 (v/v) PE: EtOAc) = 0.175 |

TABLE 1-continued

Substituted phenyl bis(indolyl)methanes (BIMs) described in this application

| Indole | Aldehyde | Product | Details |
|---|---|---|---|
| 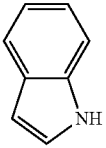 | 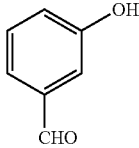 | 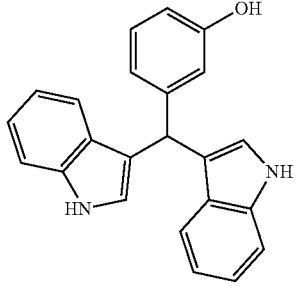<br>SP-BIM 9 | Name: bis(indol-3-yl)-3-hydroxyphenyl<br>Chemical Formula: $C_{23}H_{18}N_2O$<br>Molecular Weight: 338.41<br>Yield: 93%<br>TLC $R_f$ (3:2 (v/v) PE: EtOAc) = 0.1 |
| 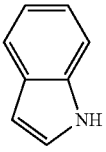 | 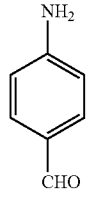 | 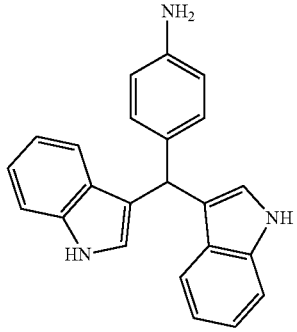<br>SP-BIM 10 | Name: bis(indol-3-yl)-4-amino-phenylmethane<br>Chemical Formula: $C_{23}H_{19}N_3$<br>Molecular Weight: 337.43<br>Yield: 78% |
| 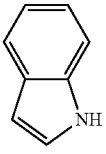 | 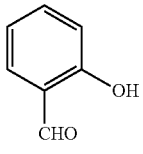 | 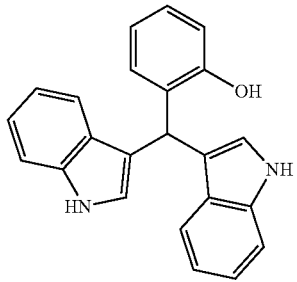<br>SP-BIM 11 | Name: bis(indol-3-yl)-2-hydroxyphenylmethane<br>Chemical Formula: $C_{23}H_{18}N_2O$<br>Molecular Weight: 338.41<br>Yield: 56% |
| 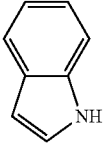 | 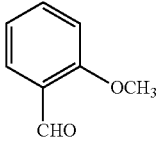 | 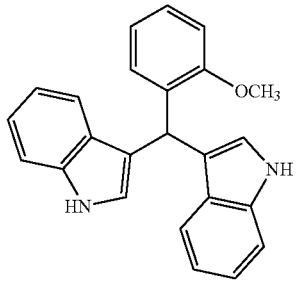<br>SP-BIM 12 | Name: bis(indol-3-yl)-2-methoxyphenylmethane<br>Chemical Formula: $C_{24}H_{20}N_2O$<br>Molecular Weight: 352.44<br>Yield: 49% |

TABLE 1-continued

Substituted phenyl bis(indolyl)methanes (BIMs) described in this application

| Indole | Aldehyde | Product | Details |
|---|---|---|---|
| indole | 3,4,5-trihydroxybenzaldehyde | SP-BIM 13 | Name: bis(indol-3-yl)-2,3,5-trihydroxyphenylmethane<br>Chemical Formula: $C_{23}H_{18}N_2O_3$<br>Molecular Weight: 370.41<br>Yield: 81%<br>TLC $R_f$ (9:1 (v/v) $CHCl_3$: MeOH) = 0.21 |
| indole | phenanthrene-9-carboxaldehyde | SP-BIM 14 | Name: bis[indol-3-yl]-phenanthren-9-ylmethane<br>Chemical Formula: $C_{31}H_{22}N_2$<br>Molecular Weight: 422.53<br>Yield: 29% |
| indole | 5-bromo-2-hydroxybenzaldehyde | SP-BIM 15 | Name: bis(indol-3-yl)-[4-bromo-3-hydroxyphenyl]methane<br>Chemical Formula: $C_{23}H_{17}BrN_2O$<br>Molecular Weight: 417.31<br>Yield: 65% |
| indole | p-tolualdehyde | SP-BIM 16 | Name: bis(indol-3-yl)-3-methyl-phenylmethane<br>Chemical Formula: $C_{24}H_{20}N_2$<br>Molecular Weight: 336.44<br>Yield: 70% |

TABLE 1-continued

Substituted phenyl bis(indolyl)methanes (BIMs) described in this application

| Indole | Aldehyde | Product | Details |
|---|---|---|---|
| indole | 5-bromo-2-formylphenol | SP-BIM 17 | Name: 4-bromo-2-hydroxy-phenylbis(indol-3-yl)methylium<br>Chemical Formula: $C_{23}H_{16}BrN_2O^+$<br>Molecular Weight: 416.30<br>Yield: 30% |
| indole | 4-methoxybenzaldehyde | SP-BIM 18 | Name: bis(indol-3-yl)-4-methoxyphenylmethane<br>Chemical Formula: $C_{24}H_{20}N_2O$<br>Molecular Weight: 352.44<br>Yield: 65% |
| 5-methoxyindole | 3-hydroxybenzaldehyde | SP-BIM 19 | Name: bis(6-methoxyindoly-3-yl)-3-hydroxyphenylmethane<br>Chemical Formula: $C_{25}H_{22}N_2O_3$<br>Molecular Weight: 398.46<br>Yield: 90% |
| 5-methoxyindole | 4-nitrobenzaldehyde | SP-BIM 20 | Name: bis(6-methoxyindol-3-yl)-4-nitrophenylmethane<br>Chemical Formula: $C_{25}H_{21}N_3O_4$<br>Molecular Weight: 427.46<br>Yield: 95% |

TABLE 1-continued

Substituted phenyl bis(indolyl)methanes (BIMs) described in this application

| Indole | Aldehyde | Product | Details |
|---|---|---|---|
| 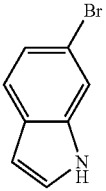 | 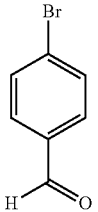 | 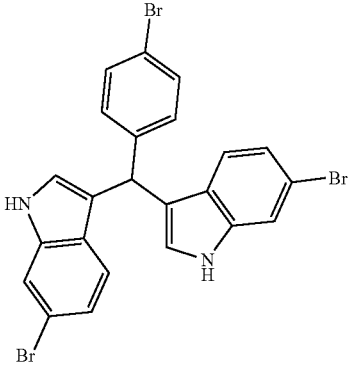 SP-BIM 21 | Name: 3,3'-((4-bromophenyl)-methylene)bis(6-bromo-1H indole)<br>Chemical formula: $C_{23}H_{15}Br_3N_2$<br>Molecular weight: 559.0990<br>Yield: 72%<br>TLC $R_f$ (7:3 (v/v) PE: EtOAc) = 0.46 |
| 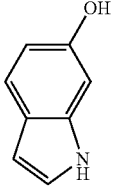 | 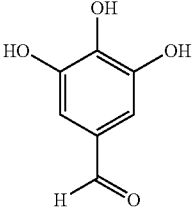 | 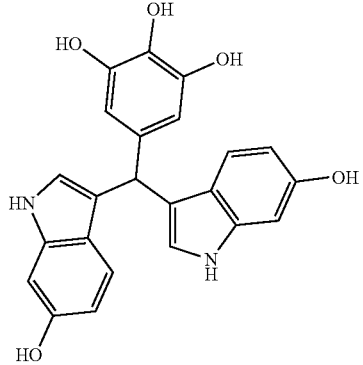 SP-BIM 22 | Name: 5-(bis(6-hydroxy-1H-indol-3-yl)methyl)benzene-1,2,3-triol<br>Chemical formula: $C_{23}H_{18}N_2O_5$<br>Molecular weight: 402.4060<br>Yield: 95% |
| 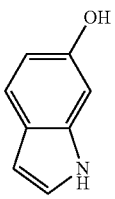 | 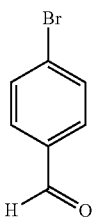 | 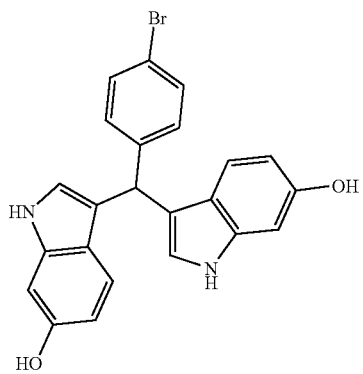 SP-BIM 23 | Name: 3,3'-((4-bromophenyl)-methylene)bis(1H-indol-6-ol)<br>Chemical formula: $C_{23}H_{17}BrN_2O_2$<br>Molecular weight: 433.3050<br>Yield: 89% |

TABLE 1-continued

Substituted phenyl bis(indolyl)methanes (BIMs) described in this application

| Indole | Aldehyde | Product | Details |
|---|---|---|---|
| 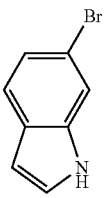 | 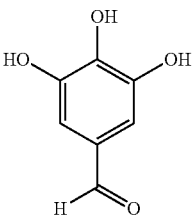 | 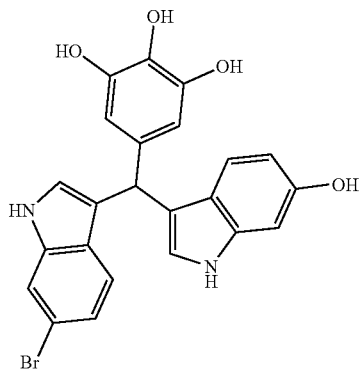<br>SP-BIM 24 | Name: 5-(bis(6-bromo-1H-indol-3-yl)methyl)benzene-1,2,3-triol<br>Chemical formula: $C_{23}H_{16}Br_2N_2O_3$<br>Molecular weight: 528.2000<br>Yield: 80% |
| 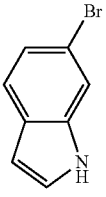 | 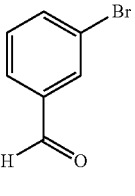 | 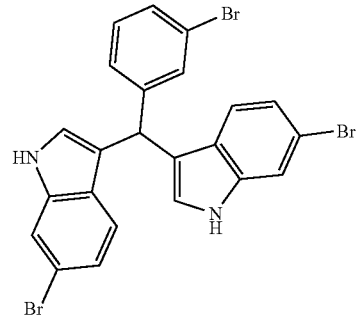<br>SP-BIM 25 | Name: 3,3'-((3-bromophenyl)-methylene)bis(6-bromo-1H-indole)<br>Chemical formula: $C_{23}H_{15}Br_3N_2$<br>Molecular weight: 559.0990<br>Yield: 91% |
|  | 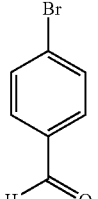 | 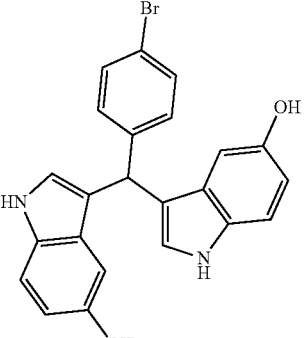<br>SP-BIM 26 | Name: 3,3'-((4-bromophenyl)-methylene)bis(1H-indol-5-ol)<br>Chemical formula: $C_{23}H_{17}BrN_2O_2$<br>Molecular weight: 433.3050<br>Yield: 58% |

TABLE 1-continued

Substituted phenyl bis(indolyl)methanes (BIMs) described in this application

| Indole | Aldehyde | Product | Details |
|---|---|---|---|
| | | SP-BIM 27 | Name: 5-(bis(5-hydroxy-1H-indol-3-yl)methyl)benzene-1,2,3-triol<br>Chemical formula: $C_{23}H_{18}N_2O_5$<br>Molecular weight: 402.4060<br>Yield: 67%<br>TLC $R_f$ (6:4 (v/v) PE:EtOAc, run twice) = 0.01 |
| | | SP-BIM 28 | Name: 3,3'-((3-bromophenyl)-methylene)bis(1H-indol-5-ol)<br>Chemical formula: $C_{23}H_{17}BrN_2O_2$<br>Molecular weight: 433.3050<br>Yield: 54%<br>TLC $R_f$ (8:2 (v/v) PE:EtOAc, run twice) = 0.05 |
| | | SP-BIM 29 | Name: 3,3'-((3-bromophenyl)-methylene)bis(1H-indol-6-ol)<br>Chemical formula: $C_{23}H_{17}BrN_2O_2$<br>Molecular weight: 433.3050<br>Yield: 77%<br>TLC $R_f$ (6:4 (v/v) PE:EtOAc, run twice) = 0.08 |

Example 1: Isolation, Synthesis and Derivatization of [bis(indol-3-yl)-phenyl]methane Bis(Indol-3-yl)-phenylmethane (SP-BIM 1) was initially isolated from *Pseudomonas aeruginosa* strain UWI-1. All the SP-BIMs in this study were synthesized according to Schemes 1 and 2. Water was used as the protic solvent, but due to the insolubility of the indoles and aldehydes in this medium, a small amount (1%) of the surfactant sodium dodecyl sulfate (SDS) was added to the reaction as it forms micelles and solubilizes organic compounds. IDC-136 $C_3$ Scheme 1. Indole and substituted benzaldehyde in 1% sodium dodecyl sulfate (SDS) results in the formation of substituted bis(indol-3-yl)-phenylmethane.

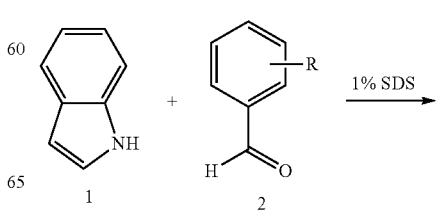

-continued

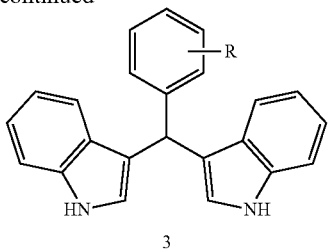

3

Scheme 2. Proposed mechanism for the formation of bis(indolyl)methanes using water as a Lewis acid.

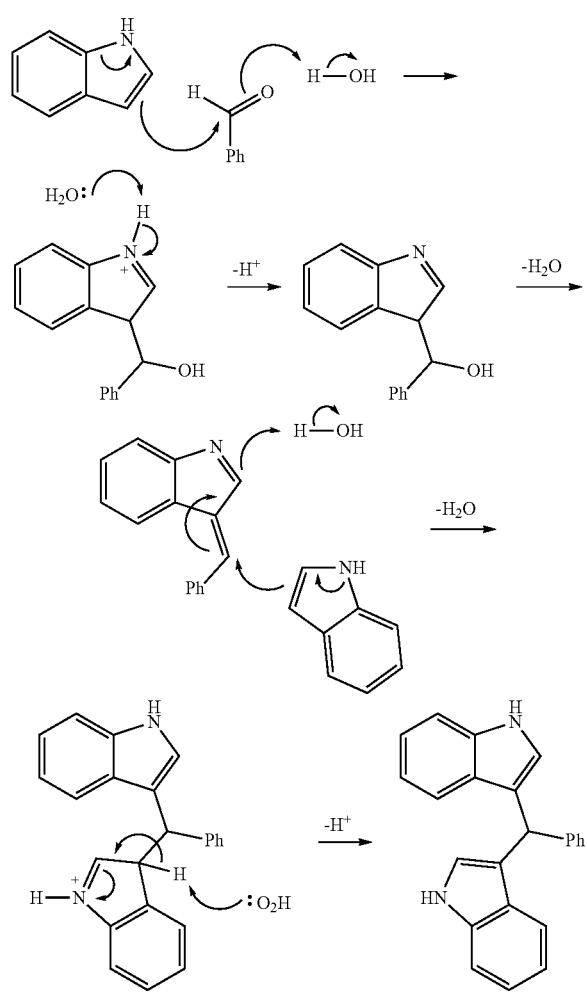

To synthesize bis(indol-3-yl)-phenylmethane SP-BIM 1, indole (2 mmol) and benzaldehyde (1 mmol) were dissolved in 10 mL 1% SDS and stirred at room temperature for 6 hours. Two volumes of ethyl acetate were added to the reaction and stirred vigorously to extract the organic material. SDS was precipitated by the slow addition of $CaCl_2$) to the aqueous/organic mixture while vigorously stirring. The organic phase was collected and dried under reduced pressure and the product purified by gravity column chromatography using petroleum ether-ethyl acetate (6:4) as the eluent. The same method using various substituted benzaldehydes was used to synthesize the other SP-BIMs (Table 1).

SP-BIM 1 was initially isolated as an amorphous red solid and displayed antibiotic activity against only the Gram-positive organisms screened. Both $^1H$ and $^3C$ NMR data compared well with literature data (Table 2), while the ESI mass spectrum showed a pseudomolecular ion at m/z 321.1363 $[M+H]^+$ consistent with the molecular formula of [bis(indol-3-yl)-phenyl]methane, $C_{23}H_{18}N_2$. All SP-BIMs were successfully synthesized with relatively high yields (Table 1).

Scheme 3. Position assignments for SP-BIM 1.

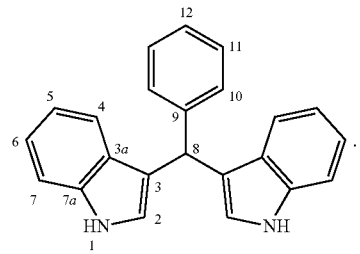

TABLE 2

Spectroscopic data for SP-BIM 1 in $CDCl_3$.

| | HSQC | | Reference Spectra* | |
|---|---|---|---|---|
| Position | $\delta H$ | $\delta C$ | $\delta H$ | $\delta C$ |
| 1 | 7.79 | — | 7.92 (brs, 2H) | — |
| 2 | 6.68 | 123.6 | 6.67 (s, 2H) | 123.6 |
| 3 | — | 136.7 | — | 136.7 |
| 3a | — | 119.7 | — | 119.9 |
| 4 | 7.37 | 119.9 | 7.35-7.40 (m) | 119.7 |
| 5 | 7.15 | 121.9 | 7.14-7.23 (m) | 121.9 |
| 6 | 6.99 | 119.2 | 7.00 (t, J = 7.5 Hz, 2H) | 119.2 |
| 7 | 7.30 | 111.0 | 7.35-7.40 (m) | 111.0 |
| 7a | — | 127.0 | — | 127.0 |
| 8 | 5.86 | 40.20 | 5.89 (s, 1H) | 40.20 |
| 9 | — | 144.0 | — | 144.1 |
| 10 | 7.32 | 128.7 | 7.35-7.40 (m) | 128.7 |
| 11 | 7.26 | 128.2 | 7.24-7.30 (m, 2H) | 128.2 |
| 12 | 7.20 | 126.1 | 7.14-7.23 (m) | 126.1 |

*Hirashita et al., Bull. Chem. Soc. Japan 2015, 88: 1760-1764 was used as reference data.

Example 2: Antibacterial Activity of SP-BIMs

Reference microorganisms used in this study included: Bacillus cereus (American Type Culture Collection (ATCC) No. 14579), Streptococcus pyogenes (ATCC No. 19615), Staphylococcus aureus (ATCC No. 12600), Enterococcus faecium (ATCC No. 19434), Corynebacterium diphtheriae (ATCC No. 27010), Escherichia coli (ATCC No. 35218), Salmonella typhimurium (ATCC No. 14028), Pseudomonas aeruginosa (ATCC No. 27853), Klebsiella pneumoniae (ATCC No. 49472), and Candida albicans (ATCC No. 22972).

Clinical strains of MRSA (n=8) and Enterococcus faecium (n=10) were provided by the Department of Para-Clinical Sciences, University of the West Indies, St. Augustine, Trinidad. All bacterial cultures were cryopreserved in 30% glycerol/Brain Heart Infusion (BHI) at −80° C. Cultures were revived on BHI agar (Oxoid Ltd, Basingstoke, Hampshire, England) and maintained at 4° C. until needed.

Prior to each experiment, cultures were streaked onto clean BHI agar plates and incubated at 35° C. for 24 hours.

Colonies of the respective cultures were selected and inoculated in phosphate buffer saline (pH 7.5) to a 0.5 McFarland turbidity standard (equivalent to $10^8$ CFU mL$^{-1}$). The bacterial suspension was then diluted 1:100 in cation adjusted Mueller Hinton Broth (ca-MHB) (Oxoid Ltd, Basingstoke, Hampshire, England).

Antibiotic powders and standard antibiotic discs were purchased from Himedia Ltd. (PA, USA). Antibiotic stock solutions were made at 50 mg mL$^{-1}$ according to Andrews, *Antimicrob. Agents Chemother.* 2001, 48:5-16 and working solutions were prepared 24 hours before needed and stored at 4° C.

Stock solutions (50 mg mL$^{-1}$) of the SP-BIM test compounds were prepared in DMSO and stored at 4° C. Working preparations of each compound was made up to 1 mg/mL in sterile deionized water with a final DMSO concentration of 10%.

To assess the antibiotic properties of the library of SP-BIMs, the broth microdilution assay was performed in 96-well microplates according to the Clinical and Laboratory Standards Institute 2014 Guidelines (CLSI 2014). The broth microdilution assay was used to determine the minimum inhibitory concentration (MIC). MIC represents the lowest concentration of the compound that would directly inhibit the growth of the pathogen. Bacterial cells (~$10^6$ CFU mL$^{-1}$) were inoculated into cation adjusted-Mueller Hinton broth containing the test compound in a twofold serial dilution ranging between 250 μg mL$^{-1}$ and 0.02 μg mL$^{-1}$. Plates were incubated at 35° C. for 18 hours after which 50 μL of 5% resazurin solution was added to each well. Resazurin is a blue dye which, upon reduction by living cells, turns to a pink resorufin product. Plates were shaken for 1 hour after the addition of the dye. The MIC was recorded as the well with the lowest concentration of test compound where no color change was observed.

The antimicrobial activity of the library of substituted [bis(indol-3yl)]methanes was assessed against a panel of ATCC reference pathogen strains of clinical relevance. Some of the SP-BIM derivatives in this study did not possess any antibacterial activity toward any pathogens used. SP-BIM 1 and SP-BIM 4 displayed antibacterial activity, and only against Gram-positive bacteria (Table 3). The MICs of SP-BIM 1 ranged from an average of 52 μg mL$^{-1}$ to 250 μg mL$^{-1}$, whereas SP-BIM 4 had MICs ranging from 104 μg mL$^{-1}$ to 166 μg mL$^{-1}$.

TABLE 3

Antibacterial activities of BIM derivatives. MIC (μg/mL)

| Compound | Gram-Positive Bacteria | | | | |
|---|---|---|---|---|---|
| | *Streptococcus pyogenes* ATCC 19615 | *Bacillus cereus* ATCC 14579 | *Enterococcus faecium* ATCC 19434 | *Corynebacterium diphtheriae* ATCC 27010 | *Staphylococcus aureus* ATCC 12600 |
| SP-BIM 1 | 83 | 83 | 52 | 125 | >250 |
| SP-BIM 2 | >250 | >250 | >250 | >250 | >250 |
| SP-BIM 3 | >250 | >250 | >250 | >250 | >250 |
| SP-BIM 4 | 104 | 125 | 104 | 166 | 166 |
| SP-BIM 5 | >250 | >250 | >250 | >250 | >250 |
| SP-BIM 6 | >250 | >250 | >250 | >250 | >250 |
| SP-BIM 7 | >250 | >250 | >250 | >250 | >250 |
| SP-BIM 8 | >250 | >250 | >250 | >250 | >250 |
| SP-BIM 9 | >250 | >250 | >250 | >250 | >250 |
| SP-BIM 10 | >250 | >250 | >250 | >250 | >250 |
| SP-BIM 11 | >250 | >250 | >250 | >250 | >250 |
| SP-BIM 12 | >250 | >250 | >250 | >250 | >250 |
| SP-BIM 13 | 125 | 125 | 125 | >250 | >250 |
| SP-BIM 14 | 125 | 125 | 125 | >250 | >250 |
| SP-BIM 15 | 125 | 125 | 125 | >250 | >250 |
| SP-BIM 16 | >250 | >250 | >250 | >250 | >250 |
| SP-BIM 17 | >250 | >250 | >250 | >250 | >250 |
| SP-BIM 18 | >250 | >250 | >250 | >250 | >250 |
| SP-BIM 19 | >250 | >250 | >250 | >250 | >250 |
| SP-BIM 20 | >250 | >25 | >250 | >250 | >250 |

| Compound | Gram-Negative Bacteria | | | | Yeast |
|---|---|---|---|---|---|
| | *Klebisella pneumoniae* ATCC 49472 | *Escherichia coli* ATCC 35218 | *Salmonella typkimurium* ATCC 14028 | *Pseudomonas aeruginosa* ATCC 27853 | *Candida albicans* ATCC 22972 |
| SP-BIM 1 | >250 | >250 | 250 | 250 | 250 |
| SP-BIM 2 | >250 | >250 | 250 | 250 | 250 |
| SP-BIM 3 | >250 | >250 | 250 | 250 | 250 |
| SP-BIM 4 | >250 | >250 | 250 | 250 | 250 |
| SP-BIM 5 | >250 | >250 | 250 | 250 | 250 |
| SP-BIM 6 | >250 | >250 | 250 | 250 | 250 |
| SP-BIM 7 | >250 | >250 | 250 | 250 | 250 |
| SP-BIM 8 | >250 | >250 | 250 | 250 | 250 |
| SP-BIM 9 | >250 | >250 | 250 | 250 | 250 |
| SP-BIM 10 | >250 | >250 | 250 | 250 | 250 |
| SP-BIM 11 | >250 | >250 | 250 | 250 | 250 |
| SP-BIM 12 | >250 | >250 | 250 | 250 | 250 |
| SP-BIM 13 | >250 | >250 | 250 | 250 | 250 |

TABLE 3-continued

Antibacterial activities of BIM derivatives.
MIC (µg/mL)

| | | | | | |
|---|---|---|---|---|---|
| SP-BIM 14 | >250 | >250 | 250 | 250 | 250 |
| SP-BIM 15 | >250 | >250 | 250 | 250 | 250 |
| SP-BIM 16 | >250 | >250 | 250 | 250 | 250 |
| SP-BIM 17 | >250 | >250 | 250 | 250 | 250 |
| SP-BIM 18 | >250 | >250 | 250 | 250 | 250 |
| SP-BIM 19 | >250 | >250 | 250 | 250 | 250 |
| SP-BIM 20 | >250 | >250 | 250 | 250 | 250 |

Example 3: SP-BIM Derivatives Potentiate a Broad Range of Antibiotics

To assess the antibiotic potentiating capacity of the library of SP-BIMs, a similar broth microdilution assay was performed according to CLSI 2014, with modifications. Respective antibiotics were added to each well in a twofold serial dilution ranging between 250 µg mL$^{-1}$ and 0.02 µg mL$^{-1}$. To each well, the SP-BIM to be tested was added to a final concentration of 50 µg mL$^{-1}$. The SP-BIMs were screened with 12 antibiotics (imipenem, erythromycin, trimethoprim, ciprofloxacin, streptomycin, aztreonam, cefalexin, vancomycin, ampicillin, doxycycline, chloramphenicol, and kanamycin) against *Staphylococcus aureus* (ATCC BAA 2312), *Bacillus cereus* (ATCC 11778), *Enterococcus faecalis* (ATCC 51299), *Pseudomonas aeruginosa* (ATCC 9027), *Enterobacter cloacae* (ATCC BAA 1143), *Streptococcus pneumoniae*, *Klebsiella pneumoniae* (ATCC BAA 2814), and *Escherichia coli* (O157:H$_7$ ATCC 35150). The antibiotics represent different chemical classes (imipenem-carbapenem, erythromycin-macrolide, trimethoprim-inhibits folic acid synthesis, ciprofloxacin-fluroquinolone, streptomycin-aminoglycoside, aztreonam-monobactam, cefalexin-cephalosporin, vancomycin-glycopeptide, ampicillin-β-lactam, doxycycline-tetracycline, chloramphenicol-inhibits protein synthesis, and kanamycin-aminoglycoside). SP-BIMs were assessed as potential adjuvants based on their ability to reduce the MIC of the antibiotic against respective pathogen.

Based on the results shown in Tables 4-7, five of the twenty selected SP-BIMs displayed the ability to reduce the concentration of antibiotic needed to kill the respective pathogen. These included:

3-(di(1H-indol-3-yl)methyl)benzaldehyde (SP-BIM 6): MICs of all antibiotics except trimethoprim were reduced at least 4-fold for MRSA and *Streptococcus*. No potentiating activity was observed for Gram-negative bacteria.

3-(di(1H-indol-3-yl)methyl)phenol (SP-BIM 9): MICs of all antibiotics except trimethoprim were reduced at least 4-fold for MRSA and *Streptococcus*. Potentiating activity was observed for the Gram-negative *E. coli* but only for kanamycin (MICs decreased from 32 µg mL$^{-1}$ to 8 µg mL$^{-1}$) and ciprofloxacin (MICs decreased from 125 µg mL$^{-1}$ to 8 µg mL$^{-1}$).

4-(di(1H-indol-3-yl)methyl)aniline (SP-BIM 10): MICs of all antibiotics except trimethoprim were reduced at least 4-fold for MRSA and *Streptococcus*. No potentiating activity was observed for Gram-negative bacteria.

5-(di(1H-indol-3-yl)methyl)benzene-1,2,3-triol (SP-BIM 13): MICs of all antibiotics except trimethoprim were reduced at least 4-fold for MRSA and *Streptococcus*. No potentiating activity was observed for Gram-negative bacteria.

5-bromo-2-(di(1H-indol-3-yl)methyl)phenol (SP-BIM 15): MICs of all antibiotics except trimethoprim were reduced at least 4-fold for MRSA and *Streptococcus*. No potentiating activity was observed for Gram-negative bacteria.

TABLE 4

Adjuvant activity of SP-BIMs 1-20 with antibiotics against MRSA.

| | MIC (µg/mL) | | | | | |
|---|---|---|---|---|---|---|
| Treatment | Ampicillin | Imipenem | Cephalexin | Erythromycin | Aztreonam | Trimethoprim |
| No compound | >250 | 4 | 16 | 4 | >250 | 250 |
| SP-BIM 1 | >250 | 4 | 16 | 4 | >250 | 250 |
| SP-BIM 2 | >250 | 4 | 16 | 4 | >250 | 250 |
| SP-BIM 3 | >250 | 4 | 16 | 4 | >250 | 250 |
| SP-BIM 4 | >250 | 4 | 16 | 4 | >250 | 250 |
| SP-BIM 5 | >250 | 4 | 16 | 4 | >250 | 250 |
| SP-BIM 6 | 0.5 | 1 | 2 | 0.5 | >250 | ND |
| SP-BIM 7 | >250 | 4 | 16 | 4 | >250 | 250 |
| SP-BIM 8 | >251 | 4 | 16 | 4 | >251 | 250 |
| SP-BIM 9 | 0.2 | 0.2 | 0.5 | 4 | 8 | 2 |
| SP-BIM 10 | 0.5 | 0.2 | 2 | <0.2 | 63 | 125 |
| SP-BIM 11 | >250 | 4 | 16 | 4 | >250 | 250 |
| SP-BIM 12 | >250 | 4 | 16 | 4 | >250 | 250 |
| SP-BIM 13 | 0.5 | 0.5 | 0.5 | 0.5 | 16 | 16 |
| SP-BIM 14 | >250 | 4 | 16 | 4 | >250 | 250 |
| SP-BIM 15 | 0.5 | 1 | 2 | 4 | 32 | 125 |
| SP-BIM 16 | >250 | 4 | 16 | 4 | >250 | 250 |
| SP-BIM 17 | >250 | 4 | 16 | 4 | >250 | 250 |
| SP-BIM 18 | >250 | 4 | 16 | 4 | >250 | 250 |
| SP-BIM 19 | >250 | 4 | 16 | 4 | >250 | 250 |
| SP-BIM 20 | >250 | 4 | 16 | 4 | >250 | 250 |

TABLE 4-continued

Adjuvant activity of SP-BIMs 1-20 with antibiotics against MRSA.

| | MIC (μg/mL) | | | | |
|---|---|---|---|---|---|
| Treatment | Streptomycin | Ciprofloxacin | Vancomycin | Doxycycline | Kanamycin |
| No compound | 63 | 2 | 4 | 8 | 16 |
| SP-BIM 1 | 63 | 2 | 4 | 8 | 16 |
| SP-BIM 2 | 63 | 2 | 4 | 8 | 16 |
| SP-BIM 3 | 63 | 2 | 4 | 8 | 16 |
| SP-BIM 4 | 63 | 2 | 4 | 8 | 16 |
| SP-BIM 5 | 63 | 2 | 4 | 8 | 16 |
| SP-BIM 6 | 1 | ND | 1 | 0.2 | 1 |
| SP-BIM 7 | 63 | 2 | 4 | 8 | 16 |
| SP-BIM 8 | 63 | 2 | 4 | 8 | 16 |
| SP-BIM 9 | 1 | 0.5 | 0.2 | 2 | 1 |
| SP-BIM 10 | 2 | <0.2 | 2 | 0.5 | 0.5 |
| SP-BIM 11 | 63 | 2 | 4 | 8 | 16 |
| SP-BIM 12 | 63 | 2 | 4 | 8 | 16 |
| SP-BIM 13 | 1 | 0.5 | 0.2 | 0.2 | 1 |
| SP-BIM 14 | 63 | 2 | 4 | 8 | 1 |
| SP-BIM 15 | 1 | 0.2 | 0.2 | 0.2 | 1 |
| SP-BIM 16 | 63 | 2 | 4 | 8 | 16 |
| SP-BIM 17 | 63 | 2 | 4 | 8 | 16 |
| SP-BIM 18 | 63 | 2 | 4 | 8 | 16 |
| SP-BIM 19 | 63 | 2 | 4 | 8 | 16 |
| SP-BIM 20 | 63 | 2 | 4 | 8 | 16 |

ND = not determined

TABLE 5

Adjuvant activity of SP-BIMs 1-20 with antibiotics against *Streptococcus pneumonia*.
MIC (μg/mL)

| Treatment | Ampicillin | Kanamycin | Cephalexin | Erythromycin | Aztreonam | Trimethoprim |
|---|---|---|---|---|---|---|
| Nocompound | 0.5 | 125 | 250 | 4 | >250 | ND |
| SP-BIM1 | 0.5 | 125 | 250 | 4 | >250 | ND |
| SP-BIM2 | 0.5 | 125 | 250 | 4 | >250 | ND |
| SP-BIM3 | 0.5 | 125 | 250 | 4 | >250 | ND |
| SP-BIM4 | 0.5 | 125 | 250 | 4 | >250 | ND |
| SP-BIM5 | 0.5 | 125 | 250 | 4 | >250 | ND |
| SP-BIM6 | <0.2 | 4 | 32 | 0.5 | 16 | ND |
| SP-BIM7 | 0.5 | 125 | 250 | 4 | >250 | ND |
| SP-BIM8 | 0.5 | 125 | 250 | 4 | >250 | ND |
| SP-BIM9 | <0.2 | 4 | 64 | 0.2 | 16 | ND |
| SP-BIM10 | <0.2 | 4 | 32 | 0.5 | 32 | ND |
| SP-BIM11 | 0.5 | 125 | 250 | 4 | >250 | ND |
| SP-BIM12 | 0.5 | 125 | 250 | 4 | >250 | ND |
| SP-BIM13 | <0.2 | 4 | 16 | 1 | 16 | ND |
| SP-BIM14 | 0.5 | 125 | 250 | 4 | >250 | ND |
| SP-BIM15 | <0.2 | 4 | 32 | 1 | 32 | ND |
| SP-BIM16 | 0.5 | 125 | 250 | 4 | >250 | ND |
| SP-BIM17 | 0.5 | 125 | 250 | 4 | >250 | ND |
| SP-BIM18 | 0.5 | 125 | 250 | 4 | >250 | ND |
| SP-BIM19 | 0.5 | 125 | 250 | 4 | >250 | ND |
| SP-BIM20 | 0.5 | 125 | 250 | 4 | >250 | ND |

| Treatment | Streptomycin | Ciprofloxacin | Vancomycin | Doxycycline |
|---|---|---|---|---|
| Nocompound | 16 | 0.2 | 1 | 63 |
| SP-BIM1 | 16 | 0.2 | 1 | 63 |
| SP-BIM2 | 16 | 0.2 | 1 | 63 |
| SP-BIM3 | 16 | 0.2 | 1 | 63 |
| SP-BIM4 | 16 | 0.2 | 1 | 63 |
| SP-BIM5 | 16 | 0.2 | 1 | 63 |
| SP-BIM6 | 2 | <0.2 | 0.5 | 8 |
| SP-BIM7 | 16 | 0.2 | 1 | 63 |
| SP-BIM8 | 16 | 0.2 | 1 | 63 |
| SP-BIM9 | 1 | <0.2 | 0.2 | 4 |
| SP-BIM10 | 2 | <0.2 | 0.5 | 8 |
| SP-BIM11 | 16 | 0.2 | 1 | 63 |
| SP-BIM12 | 16 | 0.2 | 1 | 63 |
| SP-BIM13 | 1 | <0.2 | <0.2 | 4 |
| SP-BIM14 | 16 | 0.2 | 1 | 63 |

TABLE 5-continued

Adjuvant activity of SP-BIMs 1-20 with antibiotics against *Streptococcus pneumonia*.
MIC (μg/mL)

| | | | | |
|---|---|---|---|---|
| SP-BIM15 | 1 | <0.2 | 0.2 | 8 |
| SP-BIM16 | 16 | 0.2 | 1 | 63 |
| SP-BIM17 | 16 | 0.2 | 1 | 63 |
| SP-BIM18 | 16 | 0.2 | 1 | 63 |
| SP-BIM19 | 16 | 0.2 | 1 | 63 |
| SP-BIM20 | 16 | 0.2 | 1 | 63 |

ND = not determined

TABLE 6

Adjuvant activity of SP-BIMs 1-20 with antibiotics against *Escherichia coli*.
MIC (μg/mL)

| Treatment | Ampicillin | Kanamycin | Cephalexin | Erythromycin | Aztreonam | Trimethoprim |
|---|---|---|---|---|---|---|
| Nocompound | 63 | 32 | >250 | >250 | 125 | 2 |
| SP-BM1 | 63 | 32 | >250 | >250 | 125 | 2 |
| SP-BM2 | 63 | 32 | >250 | >250 | 125 | 2 |
| SP-BM3 | 63 | 32 | >250 | >250 | 125 | 2 |
| SP-BM4 | 63 | 32 | >250 | >250 | 125 | 2 |
| SP-BM5 | 63 | 32 | >250 | >250 | 125 | 2 |
| SP-BM6 | 63 | 32 | >250 | >250 | 125 | 2 |
| SP-BM7 | 63 | 32 | >250 | >250 | 125 | 2 |
| SP-BM8 | 63 | 32 | >250 | >250 | 125 | 2 |
| SP-BM9 | 63 | 8 | >250 | >250 | 125 | 2 |
| SP-BM10 | 63 | 32 | >250 | >250 | 125 | 2 |
| SP-BM11 | 63 | 32 | >250 | >250 | 125 | 2 |
| SP-BM12 | 63 | 32 | >250 | >250 | 125 | 2 |
| SP-BM13 | 63 | 32 | >250 | >250 | 125 | 2 |
| SP-BM14 | 63 | 32 | >250 | >250 | 125 | 2 |
| SP-BM15 | 63 | 32 | >250 | >250 | 125 | 2 |
| SP-BM16 | 63 | 32 | >250 | >250 | 125 | 2 |
| SP-BM17 | 63 | 32 | >250 | >250 | 125 | 2 |
| SP-BM18 | 63 | 32 | >250 | >250 | 125 | 2 |
| SP-BM19 | 63 | 32 | >250 | >250 | 125 | 2 |
| SP-BM20 | 63 | 32 | >250 | >250 | 125 | 2 |

| Treatment | Streptomycin | Ciprofloxacin | Vancomycin | Doxycycline |
|---|---|---|---|---|
| Nocompound | 8 | 125 | 125 | 63 |
| SP-BM1 | 8 | 125 | 125 | 63 |
| SP-BM2 | 8 | 125 | 125 | 63 |
| SP-BM3 | 8 | 125 | 125 | 63 |
| SP-BM4 | 8 | 125 | 125 | 63 |
| SP-BM5 | 8 | 125 | 125 | 63 |
| SP-BM6 | 8 | 125 | 125 | 63 |
| SP-BM7 | 8 | 125 | 125 | 63 |
| SP-BM8 | 8 | 125 | 125 | 63 |
| SP-BM9 | 8 | 8 | 125 | 63 |
| SP-BM10 | 8 | 125 | 125 | 63 |
| SP-BM11 | 8 | 125 | 125 | 63 |
| SP-BM12 | 8 | 125 | 125 | 63 |
| SP-BM13 | 8 | 125 | 125 | 63 |
| SP-BM14 | 8 | 125 | 125 | 63 |
| SP-BM15 | 8 | 125 | 125 | 63 |
| SP-BM16 | 8 | 125 | 125 | 63 |
| SP-BM17 | 8 | 125 | 125 | 63 |
| SP-BM18 | 8 | 125 | 125 | 63 |
| SP-BM19 | 8 | 125 | 125 | 63 |
| SP-BM20 | 8 | 125 | 125 | 63 |

TABLE 7

Adjuvant activity of SP-BIMs 1-20 with antibiotics against *Klebsiella pneumoniae*.
MIC (µg/mL)

| Treatment | Ampicillin | Imipenem | Cephalexin | Enthromycin | Aztreonam | Trimethoprim |
|---|---|---|---|---|---|---|
| Nocompound | >250 | 2 | 8 | 32 | 8 | 16 |
| SP-BIM1 | >250 | 2 | 8 | 32 | 8 | 16 |
| SP-BLM2 | >250 | 2 | 8 | 32 | 8 | 16 |
| SP-BIM3 | >250 | 2 | 8 | 32 | 8 | 16 |
| SP-BIM4 | >250 | 2 | 8 | 32 | 8 | 16 |
| SP-BIM5 | >250 | 2 | 8 | 32 | 8 | 16 |
| SP-BIM6 | >250 | 2 | 8 | 32 | 8 | 16 |
| SP-BIM7 | >250 | 2 | 8 | 32 | 8 | 16 |
| SP-BIM8 | >250 | 2 | 8 | 32 | 8 | 16 |
| SP-BIM9 | >250 | 2 | 8 | 32 | 8 | 16 |
| SP-BIM10 | >250 | 2 | 8 | 32 | 8 | 16 |
| SP-BIM11 | >250 | 2 | 8 | 32 | 8 | 16 |
| SP-BIM12 | >250 | 2 | 8 | 32 | 8 | 16 |
| SP-BIM13 | >250 | 2 | 8 | 32 | 8 | 16 |
| SP-BIM14 | >250 | 2 | 8 | 32 | 8 | 16 |
| SP-BIM15 | >250 | 2 | 8 | 32 | 8 | 16 |
| SP-BIM16 | >250 | 2 | 8 | 32 | 8 | 16 |
| SP-BIM17 | >250 | 2 | 8 | 32 | 8 | 16 |
| SP-BIM18 | >250 | 2 | 8 | 32 | 5 | 16 |
| SP-BIM19 | >250 | 2 | 8 | 32 | 8 | 16 |
| SP-BIM20 | >250 | 2 | 8 | 32 | 8 | 16 |

| Treatment | Streptomycin | Ciprofloxacin | Vancomycin | Doxycycline |
|---|---|---|---|---|
| Nocompound | 32 | 1 | »250 | 32 |
| SP-BIM1 | 32 | 1 | »250 | 32 |
| SP-BLM2 | 32 | 1 | »250 | 32 |
| SP-BIM3 | 32 | 1 | »250 | 32 |
| SP-BIM4 | 32 | 1 | »250 | 32 |
| SP-BIM5 | 32 | 1 | »250 | 32 |
| SP-BIM6 | 32 | 1 | »250 | 32 |
| SP-BIM7 | 32 | 1 | »250 | 32 |
| SP-BIM8 | 32 | 1 | »250 | 32 |
| SP-BIM9 | 32 | 1 | »250 | 32 |
| SP-BIM10 | 32 | 1 | »250 | 32 |
| SP-BIM11 | 32 | 1 | »250 | 32 |
| SP-BIM12 | 32 | 1 | »250 | 32 |
| SP-BIM13 | 32 | 1 | »250 | 32 |
| SP-BIM14 | 32 | 1 | »250 | 32 |
| SP-BIM15 | 32 | 1 | »250 | 32 |
| SP-BIM16 | 32 | 1 | »250 | 32 |
| SP-BIM17 | 32 | 1 | »250 | 32 |
| SP-BIM18 | 32 | 1 | »250 | 32 |
| SP-BIM19 | 32 | 1 | »250 | 32 |
| SP-BIM20 | 32 | 1 | »250 | 32 |

TABLE 8

Adjuvant activity of SP-BIMs 21-29 with antibiotics against MRSA.

MIC (µg/mL)

| | Ampicillin | Vancomycin | Erythromycin | Doxycycline | Chloramphenicol | Kanamycin | Ciprofloxacin |
|---|---|---|---|---|---|---|---|
| No Compound | 4 | 2 | 8 | <0.5 | <0.5 | 8 | 0.5 |
| SP-BIM 21 | 1 | 1 | 8 | ND | ND | 8 | 0.5 |
| SP-BIM 22 | 0.5 | 0.5 | 8 | ND | ND | 4 | 0.5 |
| SP-BIM 23 | <0.5 | <0.5 | <0.5 | ND | ND | <0.5 | 0.5 |
| SP-BIM 24 | <0.5 | <0.5 | <0.5 | ND | ND | 0.5 | 0.5 |
| SP-BIM 25 | 0.5 | 0.5 | 0.5 | ND | ND | 0.5 | 0.5 |
| SP-BIM 26 | 1 | 0.5 | 4 | ND | ND | 8 | 0.5 |
| SP-BIM 27 | 0.5 | 0.5 | 0.5 | ND | ND | 1 | 0.5 |
| SP-BIM 28 | 4 | 1 | 0.5 | ND | ND | 0.5 | 0.5 |
| SP-BIM 29 | 0.5 | 0.5 | 8 | ND | ND | 0.5 | 0.5 |

TABLE 9

Adjuvant activity of SP-BIMs 21-29 with antibiotics against *Bacillus cereus*.

| | MIC (µg/mL) | | | | | | |
|---|---|---|

TABLE 12-continued

Adjuvant activity of SP-BIMs 21-29 with antibiotics against *Klebsiella pneumonia*.

| | MIC (µg/mL) | | | | | | |
|---|---|---|---|---|---|---|---|
| | Ampicillin | Vancomycin | Erythromycin | Doxycycline | Chloramphenicol | Kanamycin | Ciprofloxacin |
| SP-BIM 24 | >250 | >250 | >250 | 8 | >250 | >250 | 250 |
| SP-BIM 25 | >250 | >250 | >250 | 8 | >250 | >250 | 250 |
| SP-BIM 26 | >250 | >250 | >250 | 8 | >250 | >250 | 250 |
| SP-BIM 27 | >250 | >250 | >250 | 8 | >250 | >250 | 250 |
| SP-BIM 28 | >250 | >250 | >250 | 8 | >250 | >250 | 250 |
| SP-BIM 29 | >250 | >250 | >250 | 8 | >250 | >250 | 250 |

TABLE 13

Adjuvant activity of SP-BIMs 21-29 with antibiotics against *Enterobacter cloacae*.

| | MIC (µg/mL) | | | | | | |
|---|---|---|---|---|---|---|---|
| | Ampicillin | Vancomycin | Erythromycin | Doxycycline | Chloramphenicol | Kanamycin | Ciprofloxacin |
| No Compound | >250 | >250 | >250 | 4 | 16 | 4 | <0.5 |
| SP-BIM 21 | >250 | 125 | >250 | 4 | 16 | 2 | <0.5 |
| SP-BIM 22 | >250 | 125 | >250 | 4 | 8 | 2 | <0.5 |
| SP-BIM 23 | >250 | 125 | >250 | 2 | 8 | 2 | <0.5 |
| SP-BIM 24 | >250 | 125 | >250 | 4 | 16 | 2 | <0.5 |
| SP-BIM 25 | >250 | 125 | >250 | 8 | 16 | 4 | <0.5 |
| SP-BIM 26 | >250 | 125 | 64 | 4 | 16 | 2 | <0.5 |
| SP-BIM 27 | >250 | 125 | >250 | 4 | 16 | 2 | <0.5 |
| SP-BIM 28 | >250 | 125 | >250 | 4 | 16 | 2 | <0.5 |
| SP-BIM 29 | >250 | 125 | >250 | 4 | 8 | 2 | <0.5 |

TABLE 14

Adjuvant activity of SP-BIMs 21-29 with antibiotics against *Escherichia coli* O157:H7.

| | MIC (µg/mL) | | | | | | |
|---|---|---|---|---|---|---|---|
| | Ampicillin | Vancomycin | Erythromycin | Doxycycline | Chloramphenicol | Kanamycin | Ciprofloxacin |
| No Compound | 8 | 250 | 250 | 2 | 8 | 8 | <0.5 |
| SP-BIM 21 | 8 | 125 | 125 | 1 | 8 | 2 | <0.5 |
| SP-BIM 22 | 2 | 125 | 250 | 2 | 8 | 4 | <0.5 |
| SP-BIM 23 | 4 | 250 | 125 | 1 | 4 | 2 | <0.5 |
| SP-BIM 24 | 4 | 125 | 64 | 2 | 16 | 2 | <0.5 |
| SP-BIM 25 | 2 | 250 | 250 | 2 | 8 | 4 | <0.5 |
| SP-BIM 26 | 2 | 16 | 64 | 1 | 8 | 2 | <0.5 |
| SP-BIM 27 | 2 | 125 | 125 | 2 | 8 | 4 | <0.5 |
| SP-BIM 28 | 4 | 125 | 250 | 1 | 4 | 1 | <0.5 |
| SP-BIM 29 | 2 | 125 | 64 | 1 | 8 | 2 | <0.5 |

The SP-BIMs were screened at 50 µg mL$^{-1}$ to differentiate the active compounds from those that were less effective. Applicants surprisingly found that the compounds described herein potentiate the antibiotic activities of a range of antibiotic-agents. Without wishing to be bound by any particular theory, it is believed that the presence of electron donating groups (those with a lone pair of electrons) ($NH_2$, OH, CHO, and Br) or $NO_2$ group in the meta or para positions according to the methyl carbon (C8; as shown in Scheme 3) of the SP-BIM might contribute to adjuvant activity. Another key point is that the oxidation of the methyl carbon (C8) to a methylium moiety causes the molecule to lose activity. Also, it was observed that the addition of a methoxy functional group to C5 (as shown in Scheme 3) of the SP-BIM also did not result in any observed adjuvant effect.

Example 4: SP-BIM 9 and SP-BIM 13 Display Potent Antibiotic Adjuvant Activity Against an Extended Range of Pathogens The antibiotic adjuvant activity of SP-BIM 9 and SP-BIM 13 was further evaluated in an extensive synergy study testing the effect of combining them with antibiotics on seven reference pathogen strains (*Bacillus cereus, Streptococcus pyogenes, Enterococcus faecium, Escherichia coli, Klebsiella pneumoniae,* and *Candida albicans*). To assess adjuvant properties of the molecules, a simple checkerboard strategy was used. Concentrations of both agents were systematically diluted to identify concentrations of both drugs that achieve the most potent interaction.

A total of 50 µL of ca-Mueller-Hinton (ca-MHB) broth was distributed into each well of the microdilution plates.

Figure 20:
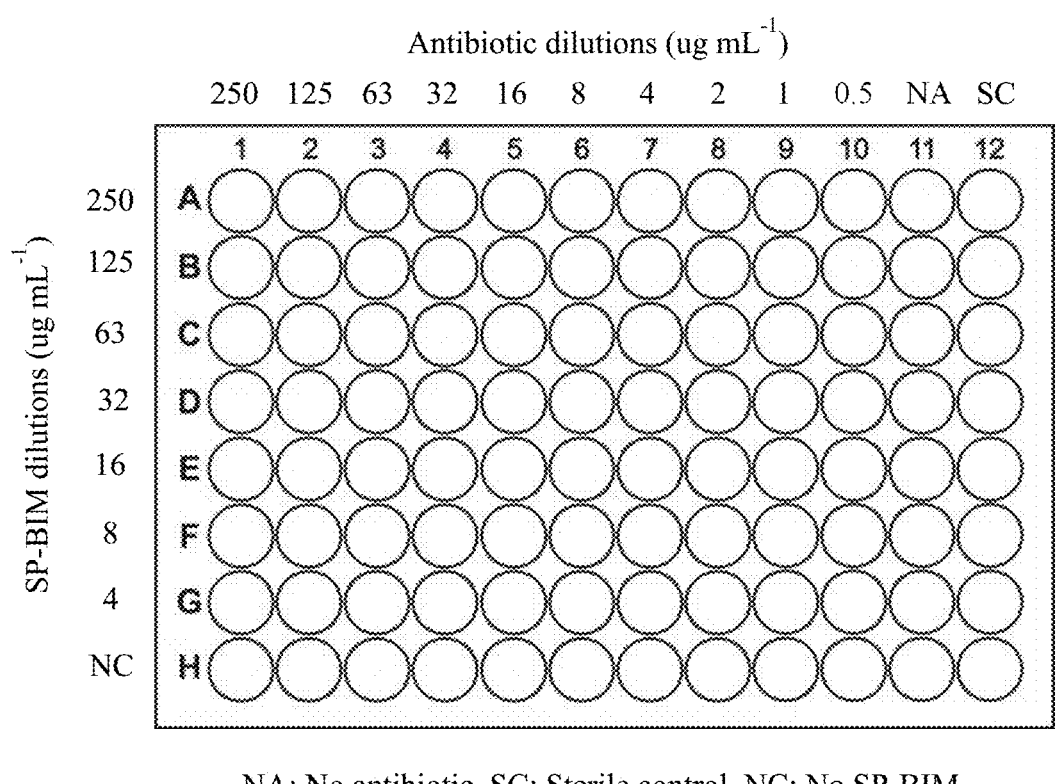
FIG. 20 shows a representation of the test 96-well plates and the respective concentrations used.

The antibiotic was serially diluted along the ordinate (columns) in a twofold serial dilution ranging between 250 µg mL$^{-1}$ and 0.5 µg mL$^{-1}$, while the test SP-BIM was diluted along the abscissa (rows) (250 µg mL$^{-1}$ and 4 µg mL$^{-1}$). Each microtiter well was then inoculated with 100 µl of bacterial inoculum of 10$^6$ CFU/ml in ca-MHB, and the plates were incubated at 35° C. for 24 hours under aerobic conditions. The above-described concentrations are illustrated in FIG. 20 which shows a representation of the test 96 well plates and the respective concentrations used.

The no antibiotic (NA) control was used to determine the MIC of SP-BIM only against the respective pathogen whereas the no SP-BIM (NC) control was used to determine the MIC of antibiotic only against the pathogen. This interaction was quantified using the fractional inhibitory concentration index (FICI) which was calculated using the lowest combination of both antibiotic (A) and SP-BIM (B) that resulted in inhibition of the organism using the following formula (Wright, *Trends Microbiol.* 2016, 24:862-871):

$$FICI = \frac{MIC \text{ of } A \text{ in combination with } B}{MIC \text{ of } A \text{ only}} + \frac{MIC \text{ of } B \text{ in combination with } A}{MIC \text{ of } B \text{ only}}$$

MIC=minimal inhibitory concentration
FICI=fractional inhibitory concentration index
Based on this calculation the interaction effect could be categorized in four classes:
Antagonistic: FICI≥4.0
Indifferent: FICI>1.0-4.0
Additive: FICI>0.5-1.0
Synergy: FICI≤0.5

SP-BIM 9

Tables 15-20 illustrate the results of the FICIs for each antibiotic in combination with SP-BIM 9 against the respective pathogens. Although not displaying any measurable antagonistic activity against any pathogen, SP-BIM 9 demonstrated potent adjuvant activity in combination with most of the antibiotics used in this study (generally good results with all antibiotics except erythromycin and trimethoprim, which gave variable results). Against the Gram-positive pathogens, most of the antibiotics showed high synergy (FICI≤0.5) with SP-BIM 9. Against MRSA, the MICs of all the antibiotics were reduced by at least 4-fold except that of trimethoprim, where an increase in the MIC was observed. The largest reduction in MIC was observed for aztreonam, a monobactam that is not used to treat Gram-positive bacteria because of its ineffectiveness. The MIC of aztreonam only was recorded as 250 µg mL$^{-1}$ but was reduced to 8 µg mL$^{-1}$ in combination with 32 µg mL$^{-1}$ of SP-BIM 9. Against *Streptococcus pneumoniae*, a similar trend was observed where SP-BIM 9 showed the ability to lower the MIC of the antibiotics at least 4-fold as well. However, no effect was observed with erythromycin. Antibiotic MICs were again reduced for all the antibiotics against *Bacillus cereus* and *Enterococcus faecium* except for erythromycin, in which no reduction was observed. Remarkably the *Enterococcus faecium* strain was highly resistant to vancomycin but the MIC was reduced to susceptible levels with 63 µg mL$^{-1}$ SP-BIM 9.

SP-BIM 9 was also able to reduce the MICs of the antibiotics against both Gram-negative strains tested (*E. coli* and *K. pneumoniae*). However, the effect varied between synergy, additive, and indifferent for the different antibiotics that were tested. Even though the MICs of the antibiotics against the Gram-negative strains were reduced significantly, the reduction required higher levels of SP-BIM 9 for the same antibiotics than against the Gram-positive bacteria. As an example, whilst the concentrations of SP-BIM 9 required to achieve a FICI of ≤0.5 for Gram-positive bacteria ranged between 4 µg mL$^{-1}$ and 63 µg mL$^{-1}$, the concentrations required to achieve a similar FICI for *E. coli* and *K. pneumoniae* were mostly 125 and 250 µg mL$^{-1}$.

SP-BIM 13

The FICI results for SP BIM 13 are shown in Tables 21-27. An effect similar to that of SP-BIM 9 was observed against the Gram-positive and Gram-negative pathogens. However, there was generally a considerably greater potentiating effect of SP-BIM 13 on the antibiotics as most MICs were reduced by tenfold or more. Similar to SP-BIM 9, combinations with trimethoprim resulted in an increase in the MIC and hence resulted in an antagonistic effect.

Overall, both SP-BIMs tended to have a greater potentiating effect on the bactericidal antibiotics such as ampicillin, vancomycin, kanamycin, streptomycin, and cephalexin, than on those with bacteriostatic mechanisms of action, including erythromycin and trimethoprim.

TABLE 15

Fractional minimum inhibitory concentrations of antibiotics in combination with SP-BIM 9 against *Staphylococcus aureus*.

| | *Staphylococcus aureus* | | | | | | | |
|---|---|---|---|---|---|---|---|---|
| | MIC antibiotic only | MIC SP-BIM 9 only | MIC in combination | | FIC of | | | |
| | | | Antibiotic | SP-BIM 9 | FIC of antibiotic | SP-BIM 9 | Σ FIC | Interpretation |
| Erythromycin | 0.1 | >250 | 0.05 | 125.0 | 0.20 | 0.50 | <0.70 | Additive |
| Trimethoprim | 1 | >250 | 2.0 | 4.0 | 2.00 | 0.02 | <2.02 | Indifferent |
| Ciprofloxacin | 1 | >250 | 0.5 | 4.0 | 0.50 | 0.02 | <0.52 | Synergy |
| Streptomycin | 8 | >250 | 1.0 | 63.0 | 0.13 | 0.25 | <0.38 | Synergy |
| Aztreonam | >250 | >250 | 8.0 | 32.0 | 0.03 | 0.12 | <0.16 | Synergy |
| Cefalexin | 4 | >250 | 0.5 | 16.0 | 0.13 | 0.06 | <0.19 | Synergy |
| Vancomycin | 2 | >250 | 0.5 | 4.0 | 0.25 | 0.02 | <0.27 | Synergy |
| Ampicillin | 0.5 | >250 | 0.2 | 125.0 | 0.40 | 0.50 | <0.90 | Additive |
| Doxycycline | 8 | >250 | 2.0 | 32.0 | 0.25 | 0.13 | <0.38 | Synergy |
| Kanamycin | 4 | >250 | 1.0 | 4.0 | 0.25 | 0.02 | ≤0.27 | Synergy |

TABLE 16

Fractional minimum inhibitory concentrations of antibiotics in combination with SP-BIM 9 against *Streptococcus pyogenes*.

*Streptococcus pneumonia*

| | MIC antibiotic only | MIC SP-BIM 9 only | MIC in combination Antibiotic | MIC in combination SP-BIM 9 | FIC of antibiotic | FIC of SP-BIM 9 | Σ FIC | Interpretation |
|---|---|---|---|---|---|---|---|---|
| Erythromycin | >250 | >250 | >250 | >250 | 1.00 | 1.00 | <2.00 | Indifference |
| Trimethoprim | 32 | >250 | 8 | 16 | 0.25 | 0.06 | <0.31 | Synergy |
| Ciprofloxacin | 2 | >250 | 0.02 | 64 | 0.01 | 0.26 | <0.27 | Synergy |
| Streptomycin | 32 | >250 | 0.2 | 16 | 0.01 | 0.06 | <0.07 | Synergy |
| Aztreonam | 125 | >250 | ND | ND | ND | ND | <0.00 | ND |
| Cefalexin | 250 | >250 | 32 | 125 | 0.13 | 0.50 | <0.63 | Additive |
| Vancomycin | 2 | >250 | 0.2 | 64 | 0.10 | 0.26 | <0.36 | Synergy |
| Ampicillin | >250 | >250 | 0.1 | 16 | 0.00 | 0.06 | <0.06 | Synergy |
| Doxycycline | 16 | >250 | 4 | 125 | 0.25 | 0.50 | <0.75 | Additive |
| Kanamycin | 32 | >250 | 4 | 8 | 0.13 | 0.03 | <0.16 | Synergy |

ND = not determined

TABLE 17

Fractional minimum inhibitory concentrations of antibiotics in combination with SP-BIM 9 against *Bacillus cereus*.

*Bacillus cereus*

| | MIC antibiotic only | MIC SP-BIM 9 only | MIC in combination Antibiotic | MIC in combination SP-BIM 9 | FIC of antibiotic | FIC of SP-BIM 9 | Σ FIC | Interpretation |
|---|---|---|---|---|---|---|---|---|
| Erythromycin | 16 | >250 | 16 | >250 | 1 | 1 | <2.0 | Indifferent |
| Trimethoprim | >250 | >250 | 2 | 16 | 0.008 | 0.064 | <0.1 | Synergy |
| Ciprofloxacin | 8 | >250 | 2 | 16 | 0.25 | 0.064 | <0.3 | Synergy |
| Streptomycin | 4 | >250 | 0.5 | >250 | 0.125 | 1 | <1.1 | Synergy |
| Aztreonam | >250 | >250 | 63 | 63 | 0.252 | 0.252 | <0.5 | Synergy |
| Cefalexin | >250 | >250 | ND | ND | ND | ND | ND | ND |
| Vancomycin | 2 | >250 | ND | ND | ND | ND | ND | ND |
| Ampicillin | 8 | >250 | ND | ND | ND | ND | ND | ND |
| Doxycycline | 4 | >250 | 0.5 | 125 | 0.125 | 0.5 | <0.6 | Synergy |
| Kanamycin | 2 | >250 | 1 | 8 | 0.5 | 0.032 | <0.5 | Synergy |

ND = not determined

TABLE 18

Fractional minimum inhibitory concentrations of antibiotics in combination with SP-BIM 9 against *Enterococcus faecium*.

*Enterococcus faecium*

| | MIC antibiotic only | MIC SP-BIM 9 only | MIC in combination Antibiotic | MIC in combination SP-BIM 9 | FIC of antibiotic | FIC of SP-BIM 9 | Σ FIC | Interpretation |
|---|---|---|---|---|---|---|---|---|
| Erythromycin | ND | ≥250 | ND | ND | ND | ND | ND | ND |
| Trimethoprim | 4 | ≥250 | ND | ND | ND | ND | ND | ND |
| Ciprofloxacin | 8 | ≥250 | ND | ND | ND | ND | ND | ND |
| Streptomycin | 32 | ≥250 | 8 | 16 | 0.3 | 0.1 | ≤0.3 | Synergy |
| Aztreonam | 125 | ≥250 | ND | ND | ND | ND | ND | ND |
| Cefalexin | 250 | ≥250 | ND | ND | ND | ND | ND | ND |
| Vancomycin | 16 | ≥250 | 0.2 | 64 | 0.013 | 0.3 | ≤0.31 | Synergy |
| Ampicillin | 250 | ≥250 | 0.1 | 64 | 0.0 | 0.3 | ≤0.3 | Synergy |

TABLE 18-continued

Fractional minimum inhibitory concentrations of antibiotics in combination with SP-BIM 9 against *Enterococcus faecium*.

*Enterococcus faecium*

| | MIC antibiotic only | MIC SP-BIM 9 only | MIC in combination | | FIC of | | | |
| --- | --- | --- | --- | --- | --- | --- | --- | --- |
| | | | Antibiotic | SP-BIM 9 | FIC of antibiotic | SP-BIM 9 | Σ FIC | Interpretation |
| Doxycycline | 8 | ≥250 | ND | ND | ND | ND | ND | ND |
| Kanamycin | 125 | ≥250 | ND | ND | ND | ND | ND | ND |

ND = not determined

TABLE 19

Fractional minimum inhibitory concentrations of antibiotics in combination with SP-BIM 9 against *Klebsiella pneumonia*.

*Klebsiella pneumoniae*

| | MIC antibiotic only | MIC SP-BIM 9 only | MIC in combination | | FIC of | | | |
| --- | --- | --- | --- | --- | --- | --- | --- | --- |
| | | | Antibiotic | SP-BIM 9 | FIC of antibiotic | SP-BIM 9 | Σ FIC | Interpretation |
| Erythromycin | 250 | ≥250 | 63 | 125 | 0.252 | 0.5 | <0.8 | Additive |
| Trimethoprim | 8 | ≥250 | 8 | 125 | 1 | 0.5 | <1.5 | Indifferent |
| Ciprofloxacin | 2 | ≥250 | 0.5 | 63 | 0.25 | 0.252 | <0.5 | Synergy |
| Streptomycin | 125 | ≥250 | 16 | 125 | 0.128 | 0.5 | <0.6 | Additive |
| Aztreonam | 125 | ≥250 | 1 | 16 | 0.008 | 0.064 | <0.1 | Synergy |
| Cefalexin | 250 | ≥250 | 4 | 125 | 0.016 | 0.5 | <0.5 | Synergy |
| Vancomycin | 125 | ≥250 | 125 | 250 | 1 | 1 | <2.0 | Indifferent |
| Ampicillin | 250 | ≥250 | 2 | 250 | 0.008 | 1 | <1.0 | Synergy |
| Doxycycline | 16 | ≥250 | 4 | 125 | 0.25 | 0.5 | <0.8 | Additive |
| Kanamycin | 4 | ≥250 | 1 | 250 | 0.25 | 1 | <1.3 | Indifferent |

TABLE 20

Fractional minimum inhibitory concentrations of antibiotics in combination with SP-BIM 9 against *Escherichia coli*.

*Escherichia coli*

| | MIC antibiotic only | MIC SP-BIM 9 only | MIC in combination | | FIC of | | | |
| --- | --- | --- | --- | --- | --- | --- | --- | --- |
| | | | Antibiotic | SP-BIM 9 | FIC of antibiotic | SP-BIM 9 | Σ FIC | Interpretation |
| Erythromycin | 250 | ≥250 | 250 | 250 | 1 | 1 | <2.0 | Indifferent |
| Trimethoprim | 2 | ≥250 | 8 | 32 | 4 | 0.128 | <4.1 | Antagonistic |
| Ciprofloxacin | 2 | ≥250 | 0.5 | 32 | 0.25 | 0.128 | <0.4 | Synergy |
| Streptomycin | 125 | ≥250 | 8 | 250 | 0.064 | 1 | <1.1 | Indifferent |
| Aztreonam | 125 | ≥250 | 32 | 125 | 0.256 | 0.5 | <0.8 | Synergy |
| Cefalexin | 250 | ≥250 | 16 | 125 | 0.064 | 0.5 | <0.6 | Synergy |
| Vancomycin | 125 | ≥250 | 125 | 250 | 1 | 1 | <2.0 | Indifferent |
| Ampicillin | 250 | ≥250 | 4 | 16 | 0.016 | 0.064 | <0.1 | Synergy |
| Doxycycline | 16 | ≥250 | 8 | 125 | 0.5 | 0.5 | <1.0 | Synergy |
| Kanamycin | 32 | ≥250 | 2 | 8 | 0.0625 | 0.032 | <0.1 | Synergy |

TABLE 21

Fractional minimum inhibitory concentrations of antibiotics in combination with SP-BIM 13 against *Staphylococcus aureus*.

| | | | *Staphylococcus aureus* | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Erythromycin | 0.1 | 63 | 0.02 | 32 | 0.2 | 0.5 | 0.7 | Additive |
| Trimethoprim | 1 | 125 | 4 | 63 | 4.0 | 0.5 | 4.5 | Antagonistic |
| Ciprofloxacin | 1 | 125 | 0.5 | 63 | 0.5 | 0.5 | 1.0 | Additive |
| Streptomycin | 8 | 125 | 0.25 | 32 | 0.0 | 0.3 | 0.3 | Synergy |
| Aztreonam | >250 | 125 | 32 | 63 | 0.1 | 0.5 | <0.6 | Additive |
| Cefalexin | 4 | 125 | 0.5 | 63 | 0.1 | 0.5 | 0.6 | Additive |
| Vancomycin | 2 | 125 | 0.25 | 32 | 0.1 | 0.3 | 0.4 | Synergy |
| Ampicillin | 0.5 | 125 | 0.5 | 4 | 1.0 | 0.0 | 1.0 | Additive |
| Doxycycline | 8 | 125 | 1 | 32 | 0.1 | 0.3 | 0.4 | Synergy |
| Kanamycin | 4 | 125 | 0.25 | 32 | 0.1 | 0.3 | 0.3 | Synergy |

TABLE 22

Fractional minimum inhibitory concentrations of antibiotics in combination with SP-BIM 13 against *Streptococcus pneumoniae*.

| | | | *Streptococcus pneumoniae* | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Erythromycin | ND | ND | ND | ND | ND | ND | ND | ND |
| Trimethoprim | 32 | >250 | 125 | 250 | 3.9 | 1.0 | <4.9 | Antagonistic |
| Ciprofloxacin | 2 | >250 | 1 | 125 | 0.5 | 0.5 | <1.0 | Additive |
| Streptomycin | 32 | >250 | 1 | 63 | 0.0 | 0.3 | <0.3 | Synergy |
| Aztreonam | 125 | >250 | 8 | 63 | 0.1 | 0.3 | <0.3 | Synergy |
| Cefalexin | 250 | >250 | 2 | 63 | 0.0 | 0.3 | <0.3 | Synergy |
| Vancomycin | 2 | 125 | 0.5 | 8 | 0.3 | 0.1 | 0.3 | Synergy |
| Ampicillin | 250 | >250 | 2 | 63 | 0.0 | 0.3 | <0.3 | Synergy |
| Doxycycline | 16 | >250 | 1 | 63 | 0.1 | 0.3 | <0.3 | Synergy |
| Kanamycin | 32 | >250 | 0.5 | 63 | 0.0 | 0.3 | <0.3 | Synergy |

ND = not determined

TABLE 23

Fractional minimum inhibitory concentrations of antibiotics in combination with SP-BIM 13 against *Enterococcus faecium*.

| | | | *Enterococcus faecium* | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Erythromycin | ND | ND | ND | ND | ND | ND | ND | ND |
| Trimethoprim | 4 | 125 | 16 | 125 | 4.0 | 1.0 | 5.0 | Antagonistic |
| Ciprofloxacin | 8 | 125 | 1 | 63 | 0.1 | 0.5 | 0.6 | Additive |
| Streptomycin | 32 | 125 | 4 | 63 | 0.1 | 0.5 | 0.6 | Additive |
| Aztreonam | 125 | 125 | 125 | 125 | 1.0 | 1.0 | 2.0 | Indifferent |
| Cefalexin | 250 | 125 | 8 | 63 | 0.0 | 0.5 | 0.5 | Synergy |
| Vancomycin | 16 | ≥250 | 8 | 125 | 0.5 | 0.5 | <1.0 | Additive |
| Ampicillin | 250 | ≥250 | 16 | 125 | 0.1 | 0.5 | <0.6 | Additive |

TABLE 23-continued

Fractional minimum inhibitory concentrations of antibiotics in combination with SP-BIM 13 against *Enterococcus faecium*.

| | *Enterococcus faecium* | | | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Doxycycline | 8 | 125 | 1 | 63 | 0.1 | 0.5 | 0.6 | Additive |
| Kanamycin | 125 | ≥250 | 4 | 63 | 0.0 | 0.3 | <0.3 | Synergy |

ND = not determined

TABLE 24

Fractional minimum inhibitory concentrations of antibiotics in combination with SP-BIM 13 against *Bacillus cereus*.

| | *Bacillus cereus* | | | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Erythromycin | 16 | 125 | 0.05 | 63 | 0.01 | 0.5 | 0.5 | Synergy |
| Trimethoprim | 250 | 125 | 250 | 125 | 1.00 | 1.0 | 2.0 | Indifferent |
| Ciprofloxacin | 0.5 | 125 | 0.5 | 4 | 1.00 | 0.0 | 1.0 | Additive |
| Streptomycin | 4 | >250 | 0.5 | 32 | 0.13 | 0.1 | <0.3 | Synergy |
| Aztreonam | 250 | 125 | 250 | 63 | 1.00 | 0.5 | 1.5 | Indifferent |
| Cefalexin | 250 | >250 | 4 | 32 | 0.02 | 0.1 | <0.1 | Synergy |
| Vancomycin | 2 | 125 | 0.25 | 0.05 | 0.13 | 0.0 | 0.1 | Synergy |
| Ampicillin | 8 | 125 | 0.5 | 32 | 0.06 | 0.3 | 0.3 | Synergy |
| Doxycycline | 4 | 125 | 1 | 32 | 0.25 | 0.3 | 0.5 | Synergy |
| Kanamycin | 2 | 125 | 0.25 | 63 | 0.13 | 0.5 | 0.6 | Additive |

TABLE 25

Fractional minimum inhibitory concentrations of antibiotics in combination with SP-BIM 13 against *Klebsiella pneumoniae*.

| | *Klebsiella pneumoniae* | | | | | | | |
|---|---|---|---|---|---|---|---|---|
| | MIC antibiotic only | MIC SP-BIM 13 only | MIC in combination | | FIC of | | | |
| | | | Antibiotic | SP-BIM 13 | FIC of antibiotic | SP-BIM 13 | Σ FIC | Interpretation |
| Erythromycin | 16 | >250 | 16 | 250 | 1.0 | 1.0 | <2.0 | Indifferent |
| Trimethoprim | 8 | >250 | 16 | 250 | 2.0 | 1.0 | <3.0 | Indifferent |
| Ciprofloxacin | 2 | >250 | 0.5 | 32 | 0.3 | 0.1 | <0.4 | Synergy |
| Streptomycin | 125 | >250 | 32 | 8 | 0.3 | 0.0 | <0.3 | Synergy |
| Aztreonam | 125 | >250 | 8 | 63 | 0.1 | 0.3 | <0.3 | Synergy |
| Cefalexin | 250 | >250 | 63 | 63 | 0.3 | 0.3 | <0.5 | Synergy |
| Vancomycin | 125 | >250 | 125 | 250 | 1.0 | 1.0 | <2.0 | Indifferent |
| Ampicillin | 250 | >250 | 250 | 63 | 1.0 | 0.3 | <1.3 | Indifferent |
| Doxycycline | 16 | >250 | 2 | 63 | 0.1 | 0.3 | <0.4 | Synergy |
| Kanamycin | 4 | >250 | 2 | 250 | 0.5 | 1.0 | <1.5 | Indifferent |

TABLE 26

Fractional minimum inhibitory concentrations of antibiotics
in combination with SP-BIM 13 against *Escherichia coli*.

*Escherichia coli*

| | MIC antibiotic only | MIC SP-BIM 13 only | MIC in combination Antibiotic | MIC in combination SP-BIM 13 | FIC of antibiotic | FIC of SP-BIM 13 | Σ FIC | Interpretation |
|---|---|---|---|---|---|---|---|---|
| Erythromycin | 16 | >250 | 16 | 250 | 1.0 | 1.0 | <2.0 | Indifferent |
| Trimethoprim | 2 | >250 | 8 | 250 | 4.0 | 1.0 | <5.0 | Antagonistic |
| Ciprofloxacin | 2 | >250 | 1 | 32 | 0.5 | 0.1 | <0.6 | Additive |
| Streptomycin | 125 | >250 | 4 | 63 | 0.0 | 0.3 | <0.3 | Synergy |
| Aztreonam | 125 | >250 | 125 | 250 | 1.0 | 1.0 | <2.0 | Indifferent |
| Cefalexin | >250 | >250 | 125 | 63 | 0.5 | 0.3 | <0.8 | Additive |
| Vancomycin | 125 | >250 | 125 | 250 | 1.0 | 1.0 | <2.0 | Indifferent |
| Ampicillin | >250 | >250 | 4 | 125 | 0.0 | 0.5 | <0.5 | Synergy |
| Doxycycline | 16 | >250 | 2 | 63 | 0.1 | 0.3 | <0.4 | Synergy |
| Kanamycin | 32 | >250 | 4 | 32 | 0.1 | 0.1 | <0.3 | Synergy |

TABLE 27

Fractional minimum inhibitory concentrations of antibiotics
in combination with SP-BIM 13 against *Candida albicans*.

*Candida albicans*

| | MIC antibiotic only | MIC SP-BIM 13 only | MIC in combination Antibiotic | MIC in combination SP-BIM 13 | FIC of antibiotic | FIC of SP-BIM 13 | Σ FIC | Interpretation |
|---|---|---|---|---|---|---|---|---|
| Erythromycin | 16 | >250 | 1 | 250 | 0.1 | 1.0 | <1.1 | Indifferent |
| Trimethoprim | >250 | >250 | 250 | 250 | 1.0 | 1.0 | <2.0 | Indifferent |
| Ciprofloxacin | 63 | >250 | 63 | 250 | 1.0 | 1.0 | <2.0 | Indifferent |
| Streptomycin | >250 | >250 | 16 | 32 | 0.1 | 0.1 | <0.2 | Synergy |
| Aztreonam | >250 | >250 | 250 | 250 | 1.0 | 1.0 | <2.0 | Indifferent |
| Cefalexin | >250 | >250 | 63 | 125 | 0.3 | 0.5 | <0.8 | Additive |
| Vancomycin | 16 | >250 | 8 | 32 | 0.5 | 0.1 | <0.6 | Additive |
| Ampicillin | >250 | >250 | 0.5 | 125 | 0.0 | 0.5 | <0.5 | Synergy |
| Doxycycline | 16 | >250 | 2 | 125 | 0.1 | 0.5 | <0.6 | Additive |
| Kanamycin | 125 | >250 | 4 | 63 | 0.0 | 0.3 | <0.3 | Synergy |

Example 5: SP-BIM 13 Breaks the Antibiotic Resistance in Clinical Strains of MRSA and *Enterococcus faecium*

SP-BIM 13 was tested against clinical antibiotic resistant isolates of MRSA (n=8) and *Enterococcus faecium* (n=10) to investigate its ability to break antibiotic resistance. First, the resistance profile for each strain was determined by the Kirby Bauer disc diffusion test outlined in CLSI (2014). After incubating at 35° C. for 24 hours, the zones of clearance were measured and the average value (n=3) was recorded. Each isolate was classified as resistant, intermediate, or susceptible based on the size of zone of inhibition from a particular antibiotic. In this study, only those antibiotics to which the bacterial strain was classified as resistant were evaluated. The checkerboard assay as previously described was used to assess the ability of SP-BIM 13 to reduce the MIC breakpoint of the antibiotic to that susceptibility. Each experiment was performed in duplicate and values are represented as the average FICI.

The average zones of inhibition of MRSA (Table 28) and *E. faecium* (Table 29) were referenced against the clinical breakpoints for bacteria published by the European Society for Clinical Microbiology and Infections Disease (EUCAST, Version 8.1) (2018) to determine their resistance for each antibiotic (Tables 30 and 31). The strains were then classified as resistant or susceptible accordingly (Tables 32 and 33). SP-BIM 13 was only used with the antibiotics to which the respective strain was resistant.

Table 34 shows the results of the antibiotic resistance breaking capability of SP-BIM 13 against antibiotic resistant strains of MRSA. Without addition of the compound, the MIC of each antibiotic for the respective MRSA strain fell over the resistant breakpoint outlined by EUCAST in 2018. However, SP-BIM 13 reduced the MIC of the antibiotic to below the susceptible breakpoint. Table 34 also shows the corresponding concentration of SP-BIM 13 that was required to break the bacteria's resistance to the antibiotic which ranged from 1 $\mu g\ mL^{-1}$ to 63 $\mu g\ mL^{-1}$. All MRSA strains were resistant to ampicillin (MIC≥250 $\mu g\ mL^{-1}$). However, SP-BIM 13 reduced the MICs for 100-fold in most cases ranging from 4 $\mu g\ mL^{-1}$ to 0.5 $\mu g\ mL^{-1}$. Similarly, the MIC of streptomycin ranged between 63 $\mu g\ mL^{-1}$ to 125 $\mu g\ mL^{-1}$ but addition of SP-BIM 13 (16 $\mu g\ mL^{-1}$) resulted in a reduction of MIC to 0.5 $\mu g\ mL^{-1}$ to 2 $\mu g\ mL^{-1}$.

The resistance breaking effect of SP-BIM 13 against clinical strains of *E. faecium* is shown in Table 35. All strains displayed resistance toward Vancomycin, MIC=32 $\mu g\ mL^{-1}$ to 63 $\mu g\ mL^{-1}$, well above the resistant breakpoint of 4 $\mu g\ mL^{-1}$. Addition of SP-BIM 13 reduced the MIC of vancomycin between 0.2 $\mu g\ mL^{-1}$ to 2 $\mu g\ mL^{-1}$. The resistant breaking effect was extended to the other antibiotics used to treat *E. faecium*.

These results are especially important as MRSA and vancomycin-resistant *Enterococcus faecium* are listed on the World Health Organization's list of priority bacteria to which new antibiotics are needed.

TABLE 28

Susceptibility profile of MRSA strains.

| MRSA strain | Zone of clearance (mm) | | | | | | |
|---|---|---|---|---|---|---|---|
| | Ampicillin | Chloramphenicol | Ciprofloxacin | Streptomycin | Erythromycin | Kanamycin | Doxycycline |
| 1621 | 11.5 | 24.5 | 31.5 | 17.0 | 21.5 | 19.5 | 21.0 |
| 5455 | 14.5 | 22.0 | 29.5 | 17.0 | 20.5 | 19.5 | 22.5 |
| 7698 | 10.5 | 16.5 | 22.5 | 12.0 | 17.5 | 8.5 | 10.5 |
| 10132 | 14.0 | 21.5 | 9.5 | 8.5 | 9.0 | 8.0 | 12.0 |
| 7172 | 14.5 | 19.5 | 26.5 | 18.5 | 17.5 | 20.5 | 19.0 |
| 7153 | 13.5 | 18.0 | 22.5 | 16.0 | 18.5 | 19.5 | 18.0 |
| 5872 | 9.0 | 20.5 | 14.5 | 8.0 | 0.0 | 0.0 | 15.0 |
| 1594 | 13.0 | 18.5 | 26.0 | 11.5 | 19.0 | 11.5 | 12.5 |

TABLE 29

Susceptibility profile of *Enterococcus faecium* strains.

| E. faecium strain | Zone of clearance (mm) | | | |
|---|---|---|---|---|
| | Ampicillin | Vancomycin | Ciprofloxacin | Streptomycin |
| 24169 | 33 | 10 | 33 | 19 |
| 21024 | 32 | 9 | 30 | 17 |
| 21955 | 32 | 15 | 35 | 13 |
| 15134 | 37 | 12 | 33 | 20 |
| RC63 | 12 | 8 | 8 | 5 |
| 23668 | 39 | 10 | 35 | 13 |
| 22870 | 10 | 10 | 12 | 29 |
| 22003 | 37 | 16 | 35 | 18 |
| 23230 | 36 | 5 | 37 | 14 |
| 23227 | 26 | 9 | 37 | 25 |

TABLE 30

Antibiotic breakpoints for MRSA strains obtained from EUCAST in 2018.

| Antibiotic | Interpretation of zone diameters (mm) | |
|---|---|---|
| | Resistant< | Susceptible > |
| Ampicillin | 18 | 18 |
| Chloramphenicol | 14 | 15 |

TABLE 30-continued

Antibiotic breakpoints for MRSA strains obtained from EUCAST in 2018.

| Antibiotic | Interpretation of zone diameters (mm) | |
|---|---|---|
| | Resistant< | Susceptible > |
| Ciprofloxacin | 13 | 14 |
| Streptomycin | 13 | 16 |
| Erythromycin | 16 | 20 |
| Kanamycin | 13 | 18 |
| Doxycycline | 19 | 20 |

TABLE 31

Antibiotic breakpoints for *E. faecium* strains obtained from EUCAST in 2018.

| Antibiotic | Interpretation of zone diameters (mm) | |
|---|---|---|
| | Resistant < | Susceptible > |
| Ampicillin | 19 | 20 |
| Vancomycin | 12 | 13 |
| Ciprofloxacin | 15 | 15 |
| Streptomycin | 14 | 14 |

TABLE 32

Interpretive standards for MRSA strains.

| MRSA Strain | Ampicillin | Chloramphenicol | Ciprofloxacin | Streptomycin | Erythromycin | Kanamycin | Doxycycline |
|---|---|---|---|---|---|---|---|
| 1621 | R | S | S | S | S | S | S |
| 5455 | R | S | S | S | S | S | S |
| 7698 | R | S | S | R | S | R | R |
| 10132 | R | S | R | R | R | R | R |
| 7172 | R | S | S | S | S | S | R |
| 7153 | R | S | S | I | S | S | R |
| 5872 | R | S | S | R | R | R | R |
| 1594 | R | S | S | R | S | R | R |

R = Resistant,
S = Susceptible,
I = Intermediate

TABLE 33

Interpretive standards for *E. faecium* strains.

| E. faecium strain | Ampicillin | Vancomycin | Ciprofloxacin | Streptomycin |
|---|---|---|---|---|
| 24169 | S | R | S | S |
| 21024 | S | R | S | S |
| 21955 | S | S | S | R |
| 15134 | S | S | S | S |
| RC63 | R | R | R | R |
| 23668 | S | R | S | R |
| 22870 | R | R | R | S |
| 22003 | S | S | S | S |
| 23230 | S | R | S | S |
| 23227 | S | R | S | S |

R = Resistant,
S = Susceptible,
I = Intermediate

TABLE 34

Reduction of MICs of antibiotics against MRSA to below susceptible breakpoint values by SP-BIM 13.

| MRSA strain | Antibiotic | MIC of antibiotic only | MIC of antibiotic in combination (µg/mL) | Rescue concentration of SP-BIM 13 (µg/mL) | FIC antibiotic | FIC compound | ΣFIC | Interpretation |
|---|---|---|---|---|---|---|---|---|
| 10132 | Ampicillin | 250 | 0.5 | 16 | 0.002 | 0.064 | <0.07 | Synergy |
|  | Ciprofloxacin | 125 | 0.5 | 32 | 0.004 | 0.128 | <0.13 | Synergy |
|  | Streptomycin | 63 | 0.5 | 16 | 0.008 | 0.064 | <0.07 | Synergy |
|  | Erythromycin | 250 | 1 | 32 | 0.004 | 0.128 | <0.13 | Synergy |
|  | Doxycycline | 8 | 0.5 | 8 | 0.063 | 0.032 | <0.09 | Synergy |
| 7172 | Ampicillin | 250 | 2 | 32 | 0.008 | 0.128 | <0.14 | Synergy |
|  | Doxycycline | 8 | 2 | 32 | 0.250 | 0.128 | <0.38 | Synergy |
| 5872 | Ampicillin | 250 | 0.5 | 32 | 0.002 | 0.128 | <0.13 | Synergy |
|  | Streptomycin | 125 | 0.5 | 16 | 0.004 | 0.064 | <0.07 | Synergy |
|  | Doxycycline | 32 | 4 | 16 | 0.125 | 0.064 | <0.19 | Synergy |
|  | Erythromycin | 250 | 4 | 32 | 0.016 | 0.128 | <0.14 | Synergy |
| 1621 | Ampicillin | 250 | 0.5 | 32 | 0.002 | 0.128 | <0.13 | Synergy |
| 5455 | Ampicillin | 250 | 1 | 63 | 0.004 | 0.252 | <0.26 | Synergy |
| 7698 | Ampicillin | 250 | 2 | 32 | 0.008 | 0.128 | <0.14 | Synergy |
|  | Streptomycin | 125 | 2 | 8 | 0.016 | 0.032 | <0.05 | Synergy |
|  | Doxycycline | 16 | 1 | 32 | 0.063 | 0.128 | <0.19 | Synergy |
| 7153 | Ampicillin | 250 | 0.5 | 63 | 0.002 | 0.252 | <0.25 | Synergy |
|  | Streptomycin | 63 | 1 | 16 | 0.016 | 0.064 | <0.08 | Synergy |
|  | Doxycycline | 8 | 1 | 32 | 0.125 | 0.128 | <0.25 | Synergy |
| 1594 | Ampicillin | 250 | 4 | 32 | 0.016 | 0.128 | <0.14 | Synergy |
|  | Streptomycin | 63 | 8 | 16 | 0.127 | 0.004 | <0.13 | Synergy |
|  | Doxycycline | 8 | 1 | 63 | 0.125 | 0.3 | <0.43 | Synergy |

TABLE 35

Fractional minimum inhibitory concentrations of antibiotic resistant strains of clinical strains of resistant *Enterococcus faecium* treated with ineffective antibiotics and SP-BIM 13.

| E. faecium strain | Antibiotic | MIC of antibiotic only | MIC of antibiotic in combination (µg/mL) | Rescue concentration of SP-BIM 13 (µg/mL) | FIC antibiotic | FIC compound | ΣFIC | Interpretation |
|---|---|---|---|---|---|---|---|---|
| 24169 | Vancomycin | 63 | 0.5 | 32 | 0.008 | 0.128 | <0.14 | Synergy |
| 21024 | Vancomycin | 63 | 1 | 32 | 0.016 | 0.128 | <0.14 | Synergy |
| 21955 | Streptomycin | 125 | 0.5 | 63 | 0.004 | 0252 | <0.26 | Synergy |
| RC63 | Ampicillin | 250 | 2 | 63 | 0.008 | 0252 | <0.26 | Synergy |
|  | Vancomycin | 32 | 0.2 | 63 | 0.006 | 0252 | <0.26 | Synergy |
|  | Streptomycin | 125 | 1 | 8 | 0.008 | 0.032 | <0.04 | Synergy |
|  | Ciprofloxacin | 32 | 0.5 | 32 | 0.016 | 0.128 | <0.14 | Synergy |
| 23668 | Vancomycin | 32 | 1 | 16 | 0.031 | 0.064 | <0.10 | Synergy |
|  | Streptomycin | 63 | 1 | 16 | 0.016 | 0.064 | <0.08 | Synergy |
| 22870 | Ampicillin | 250 | 2 | 32 | 0.008 | 0.128 | <0.14 | Synergy |
|  | Vancomycin | 32 | 2 | 1 | 0.063 | 0.004 | <0.07 | Synergy |
|  | Ciprofloxacin | 63 | 1 | 8 | 0.016 | 0.032 | <0.05 | Synergy |

TABLE 35-continued

Fractional minimum inhibitory concentrations of antibiotic resistant strains of clinical strains of resistant *Enterococcus faecium* treated with ineffective antibiotics and SP-BIM 13.

| E. faecium strain | Antibiotic | MIC of antibiotic only | MIC of antibiotic in combination (µg/mL) | Rescue concentration of SP-BIM 13 (µg/mL) | FIC antibiotic | FIC compound | ΣFIC | Interpretation |
|---|---|---|---|---|---|---|---|---|
| 23230 | Vancomycin | 32 | 2 | 16 | 0.063 | 0.064 | <0.13 | Synergy |
| 23227 | Vancomycin | 32 | 1 | 8 | 0.031 | 0.032 | <0.06 | Synergy |

TABLE 36

Rescue concentrations of SP-BIM 23 that reactivate chloramphenicol against *Pseudomonas aeruginosa*. Chloramphenicol vs *P. aeruginosa*

| | |
|---|---|
| MIC of chloramphenicol | 250 µg/mL |
| MIC of SP-BIM 23 | >250 µg/mL |
| MIC of chloramphenicol in combination in combination with 64 µg/mL SP-BIM 23 | 4 µg/mL |

TABLE 37

Rescue concentrations of SP-BIM 26 that reactivate vancomycin against *Escherichia coli* O157:H7. Vancomycin vs. *E. coli* O157:H7

| | |
|---|---|
| MIC of vancomycin | 250 µg/mL |
| MIC SP-BIM 26 | >250 µg/mL |
| MIC of vancomycin in combination with 125 µg/mL SP-BIM 26 | 4 µg/mL |

TABLE 38

Rescue concentrations of SP-BIM 27 that reactivate ampicillin against *Escherichia coli* O157:H7. Ampicillin vs. *E. coli* O157:H7

| | |
|---|---|
| MIC of Ampicillin | 16 µg/mL |
| MIC of SP-BIM 27 | >250 µg/mL |
| MIC of Ampicillin in combination with 125 µg/mL SP-BIM 27 | 2 µg/mL |

TABLE 39

Rescue concentrations of SP-BIM 28 that reactivate kanamycin against *Escherichia coli* O157:H7. Kanamycin vs. *E. coli* O157:H7

| | |
|---|---|
| MIC of Kanamycin | 8 µg/mL |
| MIC SP-BIM 28 | 250 µg/mL |
| MIC of Kanamycin in combination with 32 µg/mL SP-BIM 28 | 1 µg/mL |

Example 6: SP-BIM 13 was Successfully Used to Treat Mice with MRSA Septicemia Infections To determine SP-BIM 13's in vivo adjuvant efficacy, its ability to protect mice from both systemic lethal infections and systemic non-lethal infections by MRSA was tested. The MRSA clinical isolate MRSA HS 10132 was used in this trial, as it was determined to be (3-hemolytic in vitro, and was highly infectious to mice based on preliminary investigations. MRSA HS10132 was also resistant to ampicillin and resulted in rapid colonization of tissues based on preliminary studies.

Ten-week old female Swiss albino mice (18-20 g) were used in all mice studies. Mice care and handling was performed according to Buerge and Weiss, "Handling and Restraint" in The Laboratory Mouse, Elsevier 2004, and ethical approval was granted by The University of the West Indies, Campus Research Ethics Committee.

For systemic non-lethal infection, overnight cultures of MRSA HS 10132 were washed twice and re-suspended in phosphate buffer saline (PBS). Each mouse received an intra-peritoneal (i.p.) injection of 200 µl of bacterial suspension ($1.5 \times 10^7$ CFU mL$^{-1}$). One hour after infection, the mice were divided into eleven groups (six mice per group) and treated subcutaneously with the respective treatments: T0—Vehicle alone (5% DMSO+5% Polysorbate 20 in PBS); T1—ampicillin (Amp) only (125 mg kg$^{-1}$); T2—Amp+5 mg kg$^{-1}$ SP-BIM 13; T3—Amp+10 mg kg$^{-1}$ SP-BIM 13; T4—Amp+25 mg kg$^{-1}$ SP-BIM 13; T5—vancomycin (Van) only (125 mg kg$^{-1}$); T6—Van+5 mg kg$^{-1}$ SP-BIM 13; T7—Van+10 mg kg$^{-1}$ SP-BIM 13; T8—Van+25 mg kg$^{-1}$ SP-BIM 13; T9—5 mg kg$^{-1}$ SP-BIM 13 only; and T10—10 mg kg$^{-1}$ SP-BIM 13 only.

The mice were then treated once daily for two subsequent days (i.e., 24 and 48 hours). Twenty-four hours after the last dose, the mice were euthanized and their spleen and liver excised, homogenized in PBS and plated onto mannitol salt agar (MSA) plates. The plates were incubated at 35° C. for 24 hours and then MRSA counts determined (CFU/g organ).

For systemic lethal infection, the mice were treated as in the non-lethal infection studies except that the inoculation dose was 200 µl of $9 \times 10^9$ CFU mL$^{-1}$ MRSA HS 10132 suspension. The treated mice were then divided into groups for treatment regimens as described for the non-lethal infection studies and treatment was provided once daily for three days following infection. Mortality was monitored daily for five days and moribund mice were euthanized using cervical dislocation. Results are displayed as the percent mice survival (n=6) per day for the 5-day period.

Figure 10A:
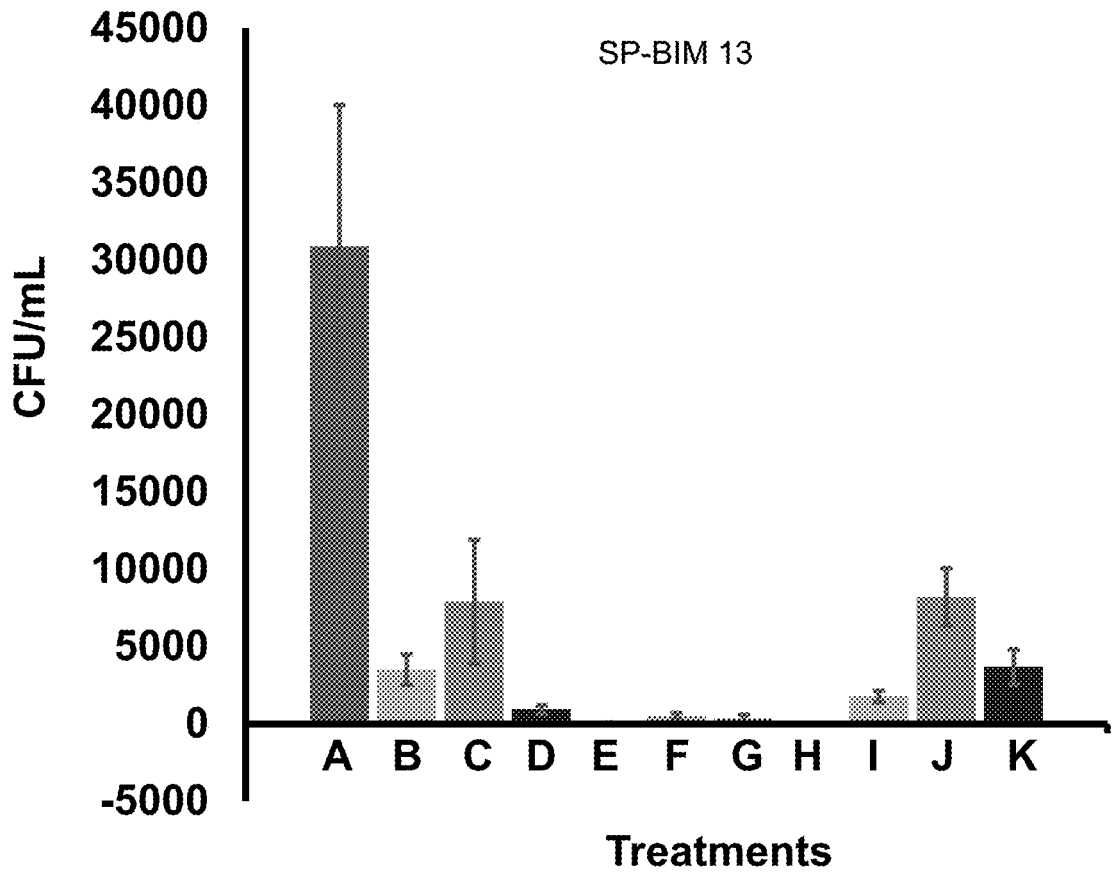
FIG. 10A depicts the in vivo adjuvant efficacy, measured as methicillin-resistant *Staphylococcus aureus* ("MRSA") load in liver, of SP-BIM 13 when administered to mice infected with a non-lethal dose of MRSA HS 10132 strain, according to one or more embodiments.

In the non-lethal infection study, SP-BIM 13 was assessed for its potentiating effect on ampicillin to reduce MRSA load in both livers and spleens of the treated animals. FIG. 10A depicts the MRSA load in mice liver after infected mice were subjected to different treatment regimens including untreated (UT), ampicillin only, ampicillin with SP-BIM 13, vancomycin alone, vancomycin with SP-BIM 13, and SP-BIM 13 only. As depicted in FIG. 10A, untreated mice had significantly higher MRSA counts (31000 CFU mL$^{-1}$) in liver compared to all other treatments. Mice treated with ampicillin only (3500 CFU mL$^{-1}$) and ampicillin+5 mg kg$^{-1}$ SP-BIM 13 (7900 CFU mL$^{-1}$) did not have a significant difference in bacterial load. However, ampicillin+10 mg kg$^{-1}$ SP-BIM 13 (900 CFU mL$^{-1}$) and ampicillin+25 mg kg$^{-1}$ SP-BIM 13 (63 CFU mL$^{-1}$) almost completely cleared MRSA from the liver. It should be noted that combinations of vancomycin and the three levels of SP-BIM 13 also resulted in almost total clearance of the MRSA from the liver. Treatments with SP-BIM 13 only at the various levels did not result in a significant clearance of the bacteria from the liver.

Figure 10B:
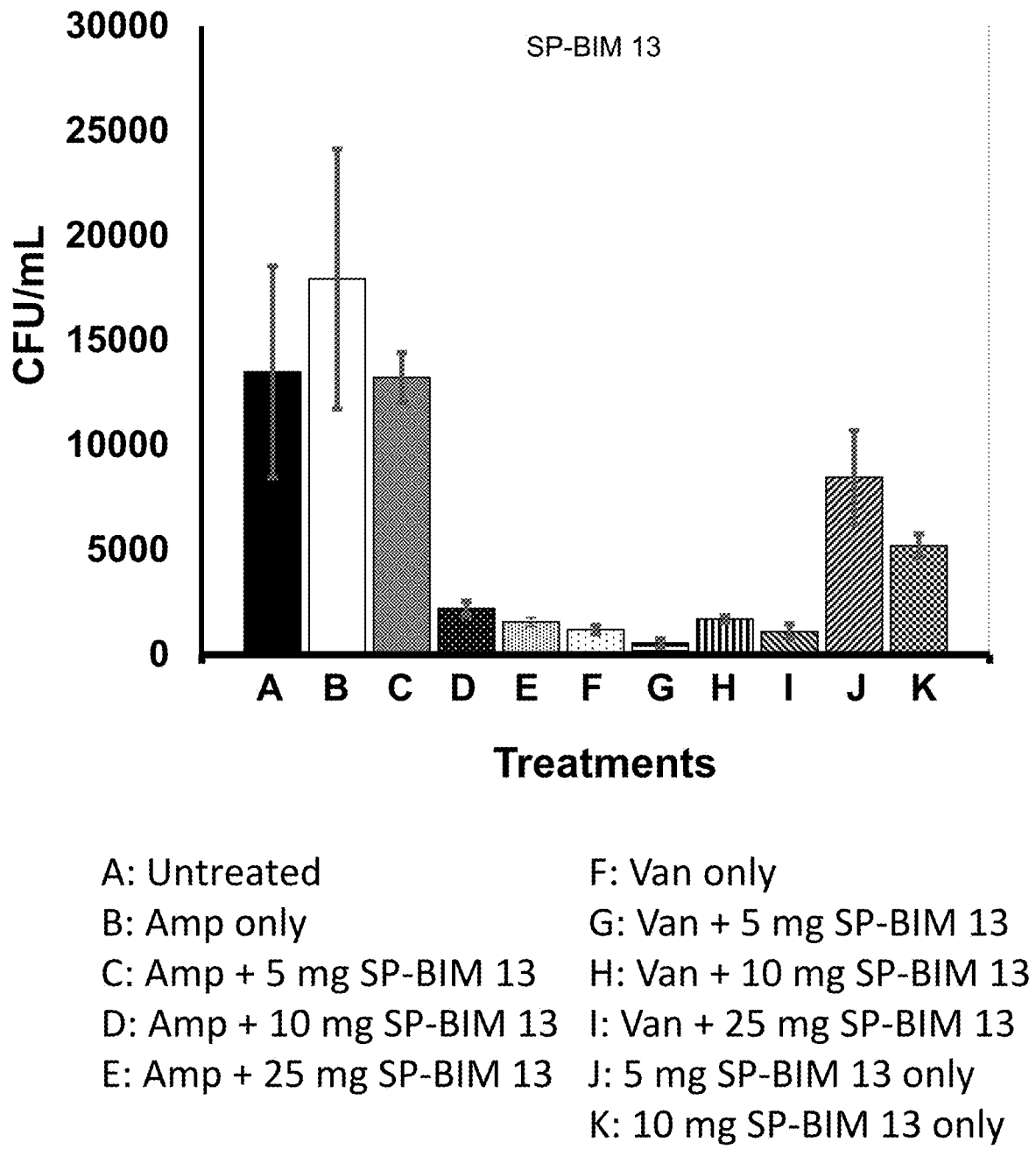
FIG. 10B depicts the in vivo adjuvant efficacy, measured as MRSA load in spleen, of SP-BIM 13 when administered to mice infected with a non-lethal dose of MRSA HS 10132 strain, according to one or more embodiments.

Similarly, MRSA load in the spleen (FIG. 10B) was significantly lower in mice that received combinations of ampicillin and SP-BIM 13 at 10 mg kg- and 25 mg kg$^{-1}$, when compared to mice that received no treatment, ampicillin only, and ampicillin+5 mg kg$^{-1}$. Treatment with both levels of SP-BIM 13 only did not significantly reduce MRSA load in the spleen.

Figure 11A:
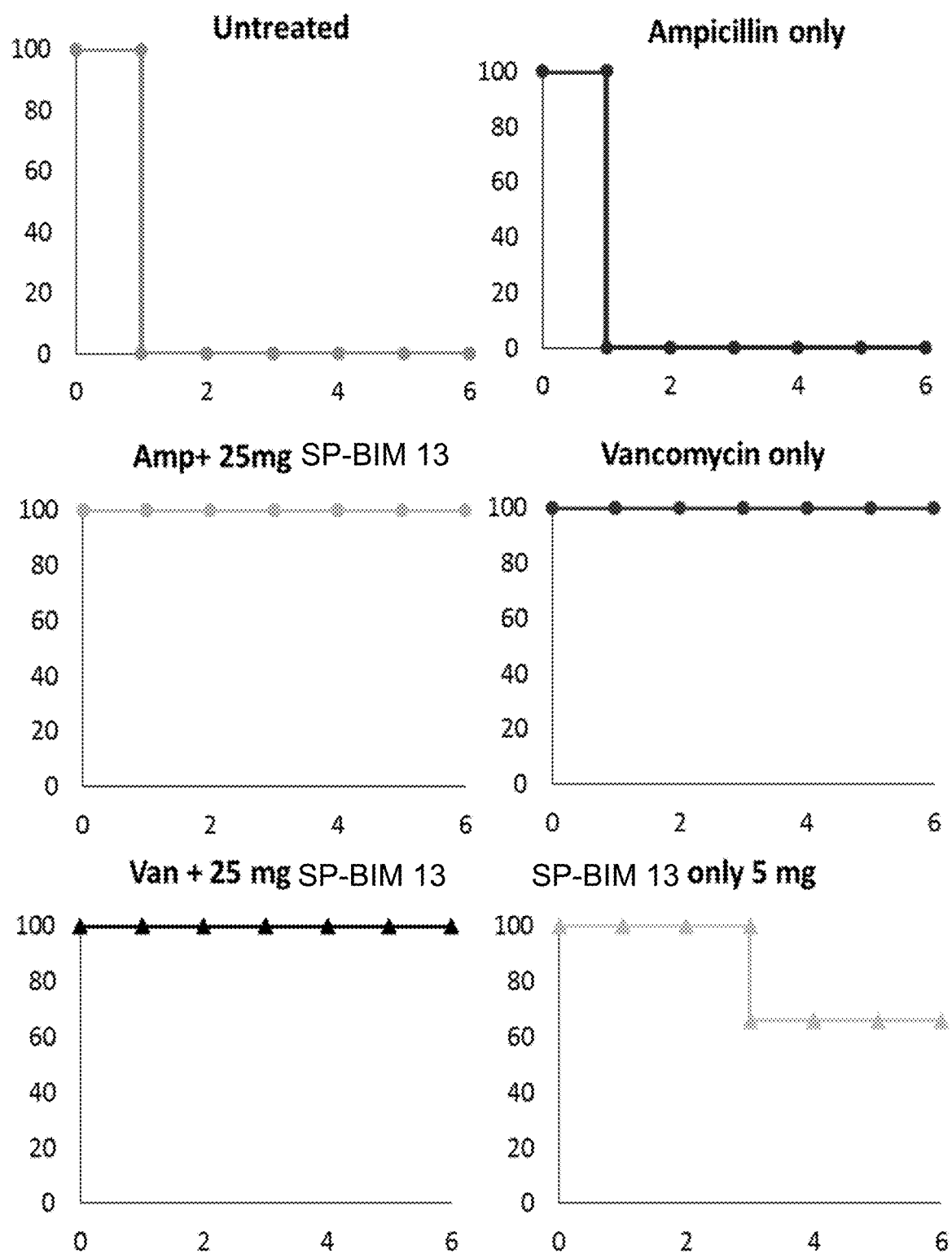
FIGS. 11A-11B depict the in vivo adjuvant efficacy of SP-BIM 13 when administered to mice infected with a lethal dose of MRSA HS 10132 strain, according to one or more embodiments.
Figure 11B:
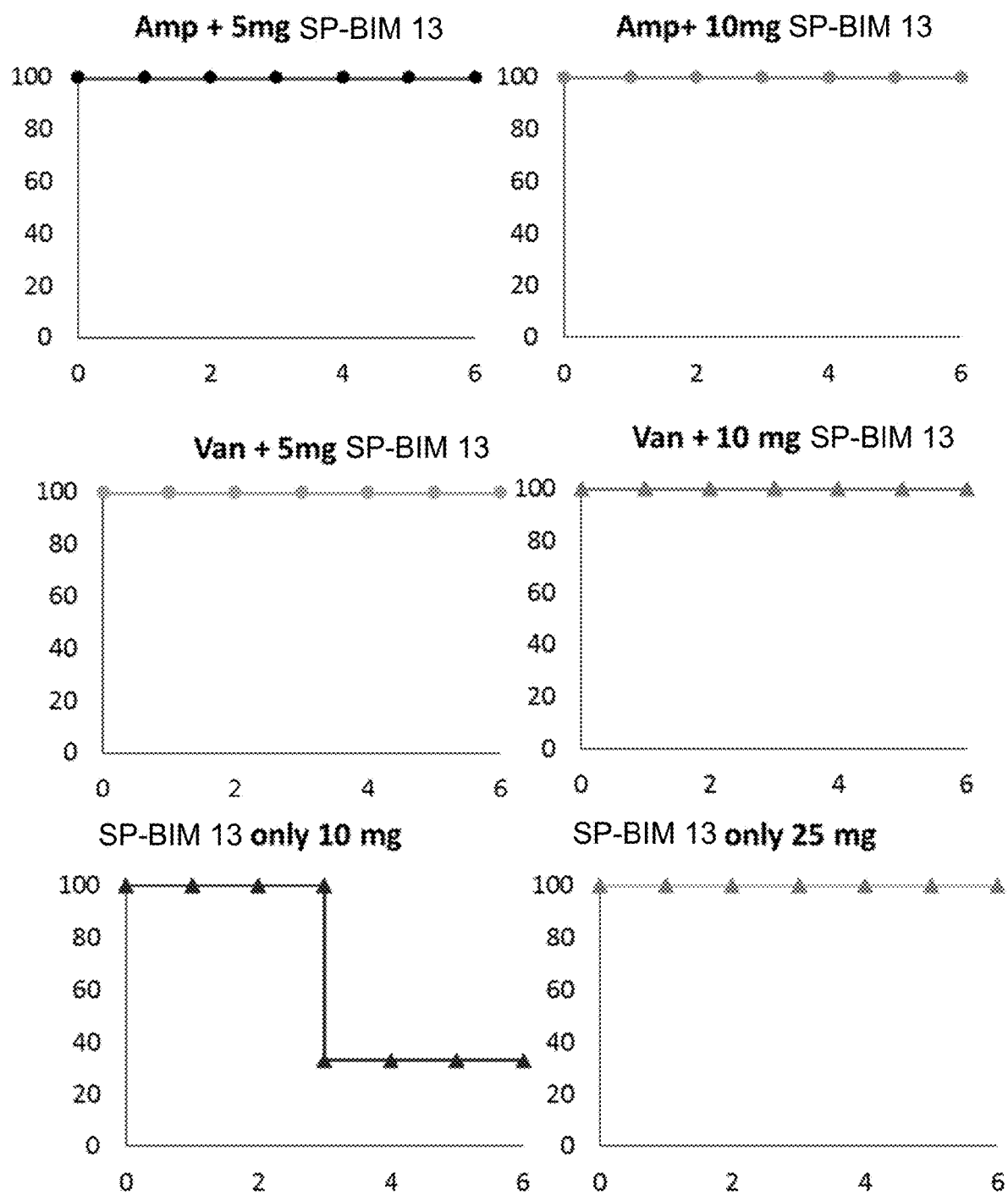

In the lethal septicemia studies mice were infected with a lethal dose of MRSA HS10132 and treated as in the non-lethal septicemia study. Mice were monitored for a total of five days post-infection. Percentage of survived animals was plotted against days of treatments. Different treatment regimens include untreated, ampicillin only, ampicillin with SP-BIM 13, vancomycin alone, vancomycin with SP-BIM 13, and SP-BIM 13 only. The survival rate of mice treated with ampicillin in combination with three levels SP-BIM 13 dramatically increased (0% mortality), compared to mice that were untreated and treated with ampicillin only (100% mortality) (FIG. 11A-B). A similarly high survival rate was observed for mice that were treated with vancomycin only and vancomycin in combination with the three levels of SP-BIM 13. Mice treated with SP-BIM 13 only had lower survival rates but deaths occurred after treatment stopped (40% mortality with 5 mg kg$^{-1}$, 60% mortality with 10 mg kg$^{-1}$, and 0% mortality with 25 mg kg$^{-1}$).

These results show that the potent in vitro antibiotic adjuvant properties displayed by SP-BIM 13 translates in vivo as it can be used with an ineffective antibiotic to protect the mice from systemic infections of MRSA. Even without antibiotics, SP-BIM 13 alone increased survival rate of the infected mice. SP-BIM 13 alone was not able to reduce MRSA counts significantly in the spleen and liver, thus the effect of reducing mortality may be due to a reduction of virulence as was observed in the in vitro studies (reduced biofilm formation and hemolysis of blood as shown below). It must be noted, however, that the mice that survived with treatment by SP-BIM 13 alone were not as active and did not appear to be as healthy as those that received the compound in combination with the antibiotic (data not shown).

Example 7: Screening SP-BIM 9 for its Ability to Reduce Sub-Lethal MRSA Infections in Mice The ability of SP-BIM 9 to clear MRSA in mice was also evaluated at a sub-lethal level of inoculation.

Mice were inoculated with a sub-lethal dose of MRSA HS10132 as in Example 6. The infected mice were then treated with different combinations of ampicillin (125 mg kg$^{-1}$) and SP-BIM 9 (5 mg kg$^{-1}$ and 10 mg kg$^{-1}$) and the liver and spleen harvested and analyzed for MRSA counts.

Figure 12:
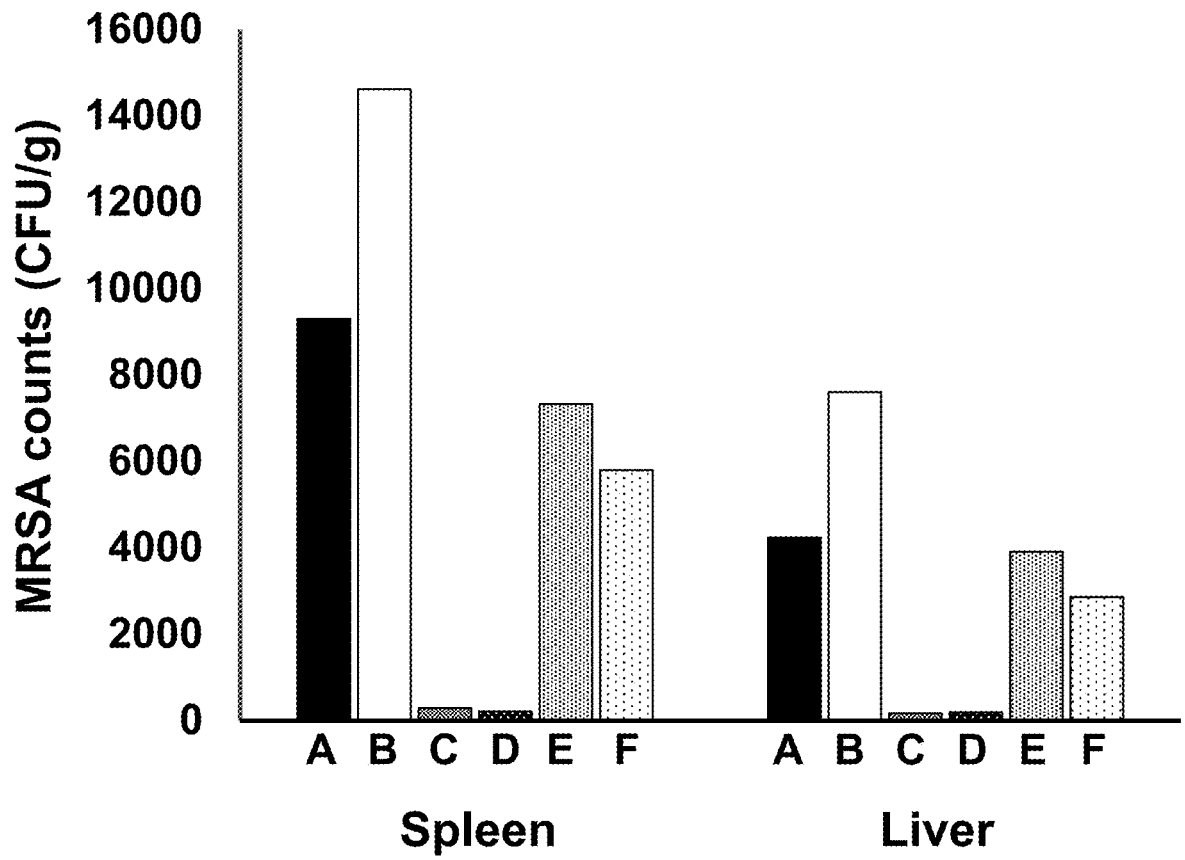
FIG. 12 depicts the in vivo adjuvant efficacy of SP-BIM 9 when administered to mice infected with a non-lethal dose of MRSA HS 10132 strain, according to one or more embodiments.

The results show that MRSA counts were significantly reduced in liver and spleen of mice treated with combinations of ampicillin and SP-BIM 9 (FIG. 12). The infected mice were subjected to different treatment regimens including untreated (UT), ampicillin only, ampicillin with SP-BIM 9, and SP-BIM 9 only. The liver and spleen of the treated mice were harvested and analyzed for MRSA counts. MRSA load in the spleen of untreated mice (9,300 CFU g$^{-1}$) and mice treated with ampicillin only (14,622 CFU g$^{-1}$) were significantly higher than mice treated with combinations of ampicillin and SP-BIM 9 at 5 mg kg$^{-1}$ and 10 mg kg$^{-1}$ (288 and 211 CFU g$^{-1}$, respectively).

However, treatment with SP-BIM 9 only, at both 5 mg kg$^{-1}$ and 10 mg kg$^{-1}$, resulted in elevated bacterial loads (7327 CFU g$^{-1}$ and 5800 CFU g$^{-1}$, respectively). The same trend was observed for MRSA loads in the liver of infected mice. Animals that were treated with combinations of ampicillin and SP-BIM 9 at 5 mg kg$^{-1}$ and 10 mg kg$^{-1}$ had significantly lower MRSA counts (167 CFU g$^{-1}$ and 189 CFU g$^{-1}$, respectively) when compared to untreated mice (4238 CFU g$^{-1}$), ampicillin only (7605 CFU g$^{-1}$), and those that received SP-BIM 9 only at 5 mg kg$^{-1}$ (3911 CFU g$^{-1}$) and 10 mg kg$^{-1}$ (2861 CFU g$^{-1}$). These results show that SP-BIM 9 cannot clear MRSA cells from the body of the host as it is not per se an antimicrobial compound. The high levels of bacterial load obtained from mice treated with ampicillin only may be as a result of the stress response of the resistant bacterium toward this antibiotic. The potentiating effect of SP-BIM 9 however, was proven as combinations of ampicillin and SP-BIM 9 resulted in almost total clearance of the bacterium from the host's organs.

Example 8: SP-BIMs can Inhibit Biofilm Formed by *Staphylococcus aureus*

Biofilm inhibition was determined for 9 SP-BIMs (4 active and 5 inactive) using the crystal violet dye retention assay as outlined by O'Toole, *J. Vis. Exp.* 2010, 47:2437 in standard 96-well microtiter plates. Each SP-BIM was added in a twofold serial dilution with final concentrations ranging from 250 µg mL$^{-1}$ to 0.2 µg mL$^{-1}$. An overnight culture of *Staphylococcus aureus* was adjusted to a 2.0 McFarland standard (equivalent to 6×10$^8$ CFU mL$^{-1}$) in PBS. Cultures were diluted 1:100 in BHI medium and each well seeded with 100 µL. Untreated wells were seeded with 10% DMSO. Plates were incubated for 24 hours without shaking. After incubation, unbound cells and media were aspirated and wells were washed twice with PBS. To each well, 200 µL of 0.1% crystal violet (CV) solution was added and incubated at room temperature for 15 minutes. Plates were washed twice with excess water and 200 µL of 30% acetic acid was used to solubilize the CV and the solution transferred to clean 96-well plates and absorbance measured at 550 nm. Biofilm formation was expressed as a percentage of the untreated controls. All assays were performed in triplicate.

Figure 13:
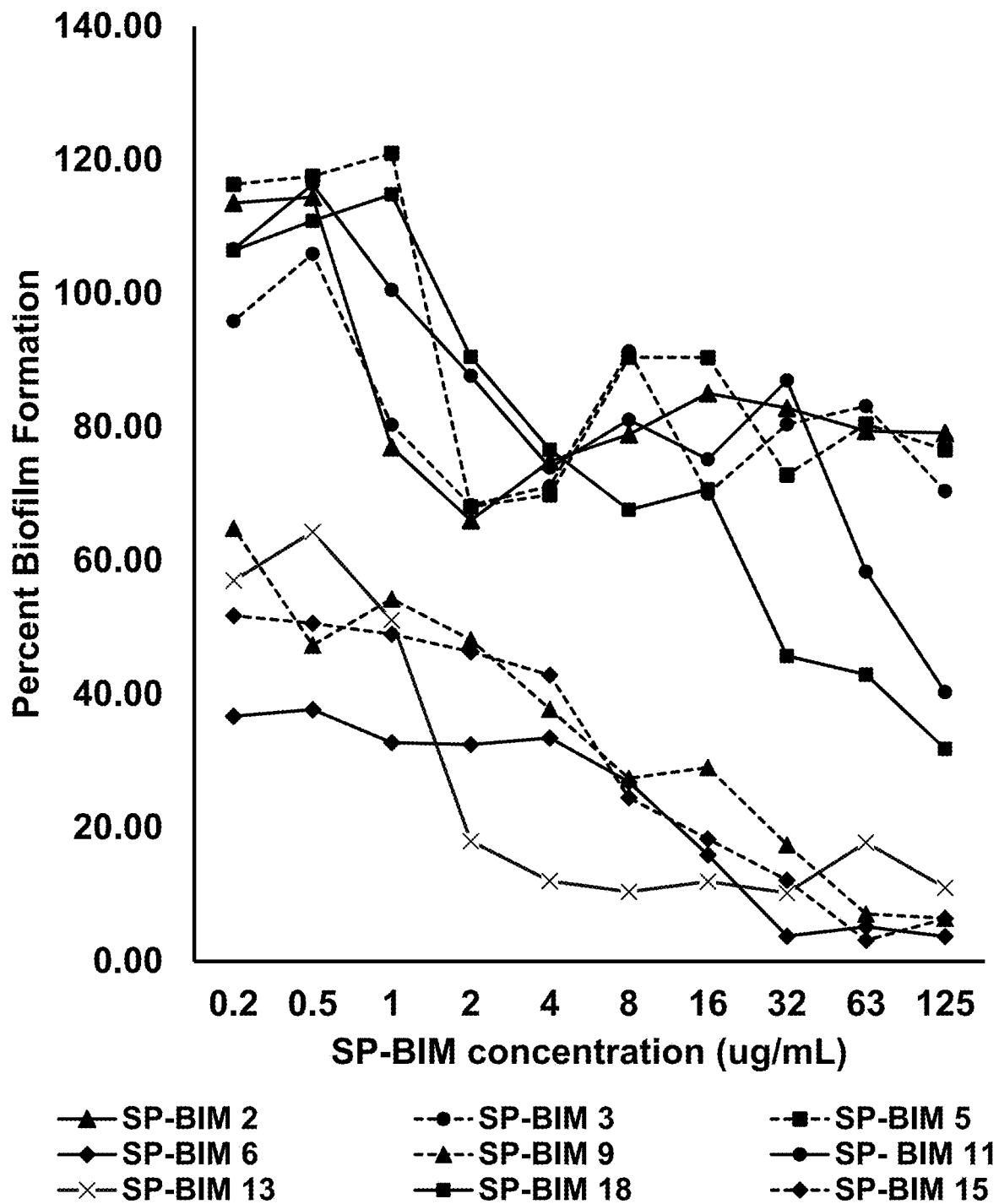
FIG. 13 depicts the efficacy of SP-BIMs 2, 3, 5, 6, 9, 11, 13, 15, and 18 in inhibiting biofilm formation of *Staphylococcus aureus* at different concentrations, according to one or more embodiments.

FIG. 13 shows the percentage of biofilm formation of *Staphylococcus aureus* cells treated with various SP-BIMs. SP-BIMs that demonstrated antibiotic adjuvant properties (SP-BIMs 6, 9, 13, 15) were compared against some of those that did not (SP-BIMs 2, 3, 5, 11, 18). The biofilm formation at different concentrations of the SP-BIMs was also assessed. There was a significant difference in biofilm inhibition between the SP-BIMs that demonstrated ("active") and those that did not ("inactive") demonstrate adjuvant activity. With the active SP-BIMs, the percentage of *S. aureus* biofilm formations ranged between 6% and 65%, whereas with the inactive SP-BIMs, the formation rate was much higher, between 32% and 121%. All SP-BIMs demonstrated an inverse correlation between the percentage of biofilm formation and the concentration of the SP-BIMs that were used. In other words, the higher the SP-BIM concentration was used, the lower percentage of biofilm was formed.

Biofilms play an important role in the pathogenicity and defense of bacteria. Biofilms essentially are a coherent cluster of bacterial cells embedded in a matrix, which is more tolerant of antimicrobials and host defenses compared with planktonic bacterial cells. The bacteria in these aggregates are physically joined together and they produce an extracellular matrix that contains many different types of extracellular polymeric substances (EPS) including proteins, DNA, and polysaccharides.

The ability of SP-BIMs to reduce biofilm formation along with enhancing antibiotic activity directly is essential to reversing resistance as planktonic cells are easier to kill than cells embedded within a biofilm.

Example 9: SP-BIM 13 Prevents Hemolysis of Sheep Erythrocytes

SP-BIM 13 was further tested in an inhibition assay of hemolysin production. The sheep blood hemolytic assay is a functional assay measuring the release of hemoglobin from erythrocytes due to the hemolytic activity of α-hemolysin (Khodaverdian et al., $Antimicrob.\ Agents\ Chemother.$ 2013, 57:3645-3652). $Staphylococcus\ aureus$ was grown at 37° C. for 24 hours and adjusted to a 2.0 McFarland standard (equivalent to $6\times10^8$ CFU $mL^{-1}$) in PBS. SP-BIM 13 was added in a twofold serial dilution with final concentrations ranging from 250 μg $mL^{-1}$ to 0.2 μg $mL^{-1}$ and incubated for 6 h at 37° C. 100 μL of bacterial culture was filtered using a 0.2 μm filter and added to 900 μL hemolysin buffer (0.145 M NaCl, 0.02 M CaCl2)) and 25 μL of defibrinated sheep blood. The solution was incubated for 15 minutes at 37° C. Samples were centrifuged (5,500×g, room temperature, 1 minute) to pellet any un-lysed blood cells. Hemolytic activity was determined by measuring the optical density at 541 nm. Sterile culture medium served as the standard for 0% hemolysis, and untreated bacterial culture was designated as the standard for 100% hemolysis. The percentage of hemolysis inhibition was calculated by comparison with the control culture. Assays were performed in triplicate.

Figure 14:
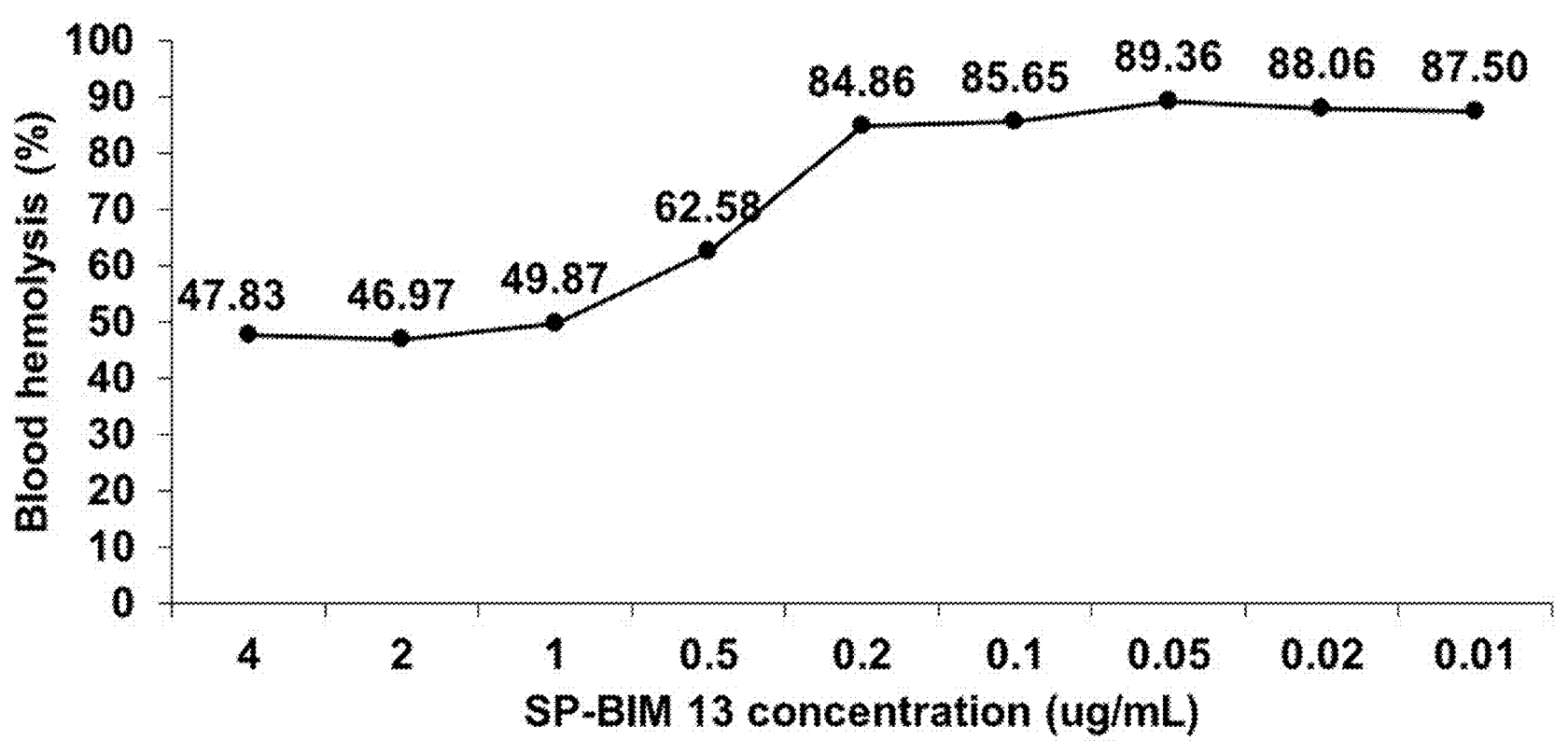

SP-BIM 13 was tested for its ability to prevent hemolysin production in $Staphylococcus\ aureus$. Bacterial cells were incubated with varying concentrations of the compound and sheep erythrocytes were incubated with the culture supernatants. The results (FIG. 14) demonstrate that SP-BIM 13 inhibits hemolysin production in $S.\ aureus$ cells. The results also show that concentration of SP-BIM 13 was adversely correlated to the percent red blood cell (RBC) lysis as the higher concentration of SP-BIM 13 resulted in lower lysis. Concentrations as low as 1 μg $mL^{-1}$ resulted in less than 50% lysis of RBCs.

Example 10: SP-BIM 13 Binds to the Catalytic Domain of Histidine Kinase walK

In silico predictions using Maestro Software (Version 11.7) suggest binding of several SP-BIM 13 to the ATP-binding domain of $B.\ cereus$ Histidine Kinase (HK) walK (PDB: 3SL2, chain A, residues 451-611). The software predicts that SP-BIM 13 docks in the ATP binding site in a mode similar to that of the natural product ADP. This suggests that SP-BIM 13 may be actively competing with ATP at its binding site on histidine kinase, which then inhibits phosphorylation of the enzyme that is necessary for the stress response of the bacteria.

Figure 15A:
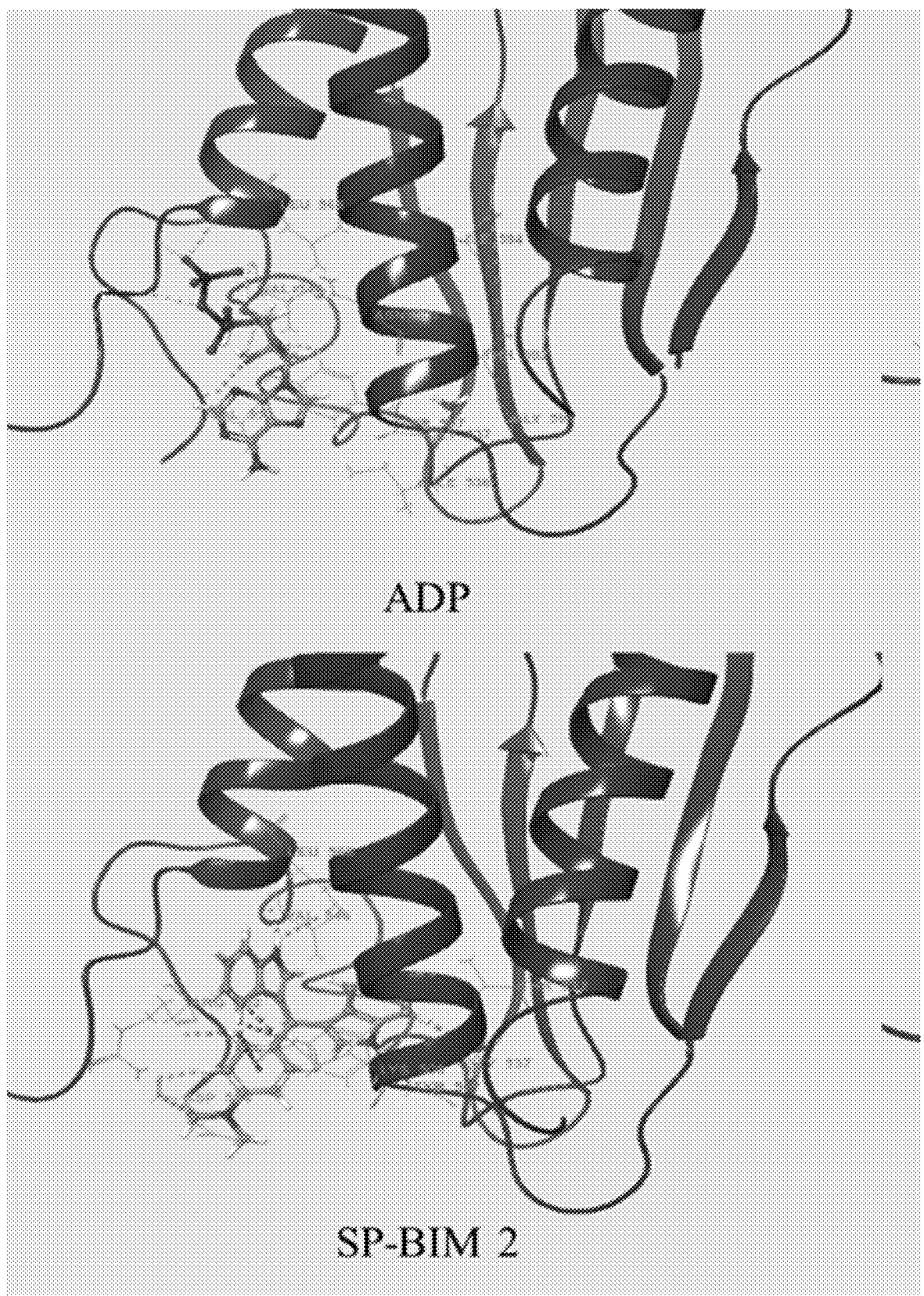
FIGS. 15A-15C depict in silico predictions of the six best docking poses of SP-BIMs 2, 9, 12, 13, and 17 onto the catalytic domain of *Bacillus cereus* histidine kinase (HK) walK (PDB: 3SL2, chain A, residues 451-611), according to one or more embodiments.
Figure 15B:
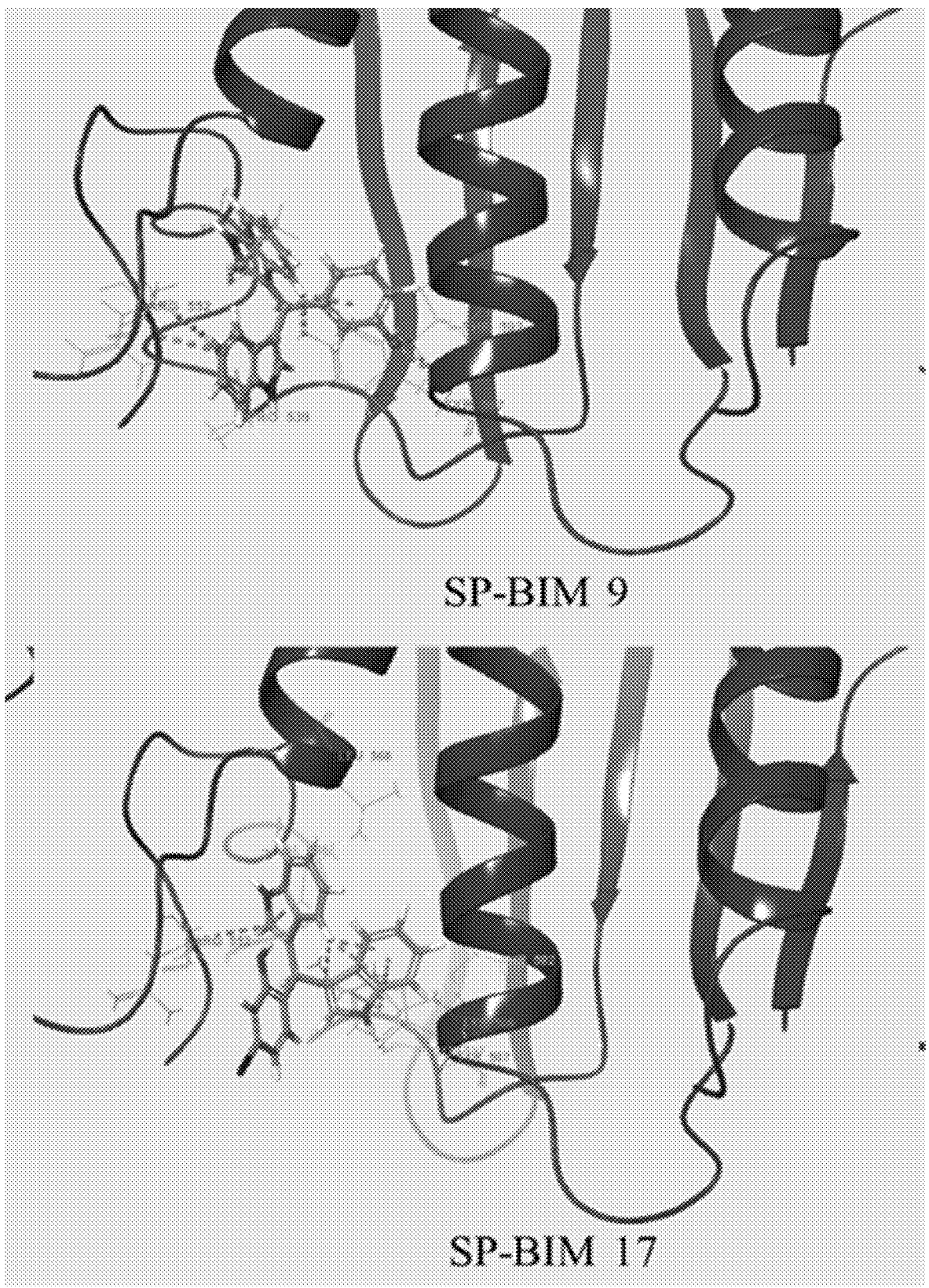
Figure 15C:
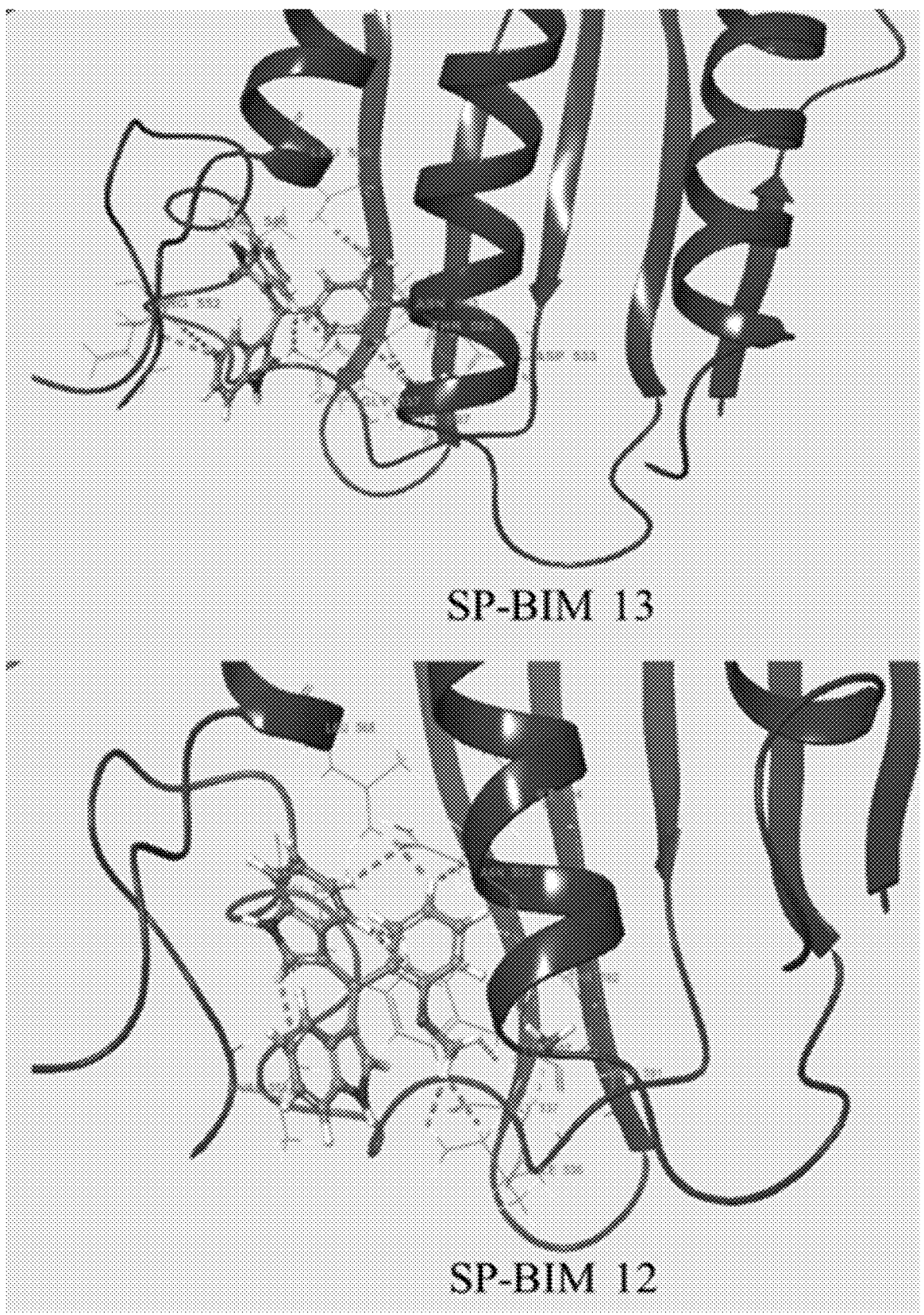

FIGS. 15A-C shows representative docking poses based on the GLIDE docking scoring function used to assess the in silico molecular docking of the library of SP-BIMs to the CA portion of the enzyme. Among the compounds shown in FIGS. 15A-C, the natural ligand (ADP) had the most favorable ligand binding free energy score, but SP-BIM 9 and 13 had similar binding scores and poses. These were then followed by SP-BIM 2, 17, and 12. The predicted higher binding affinity of SP-BIM 9 and 13 was mirrored in the in vitro studies where these compounds displayed the highest antibiotic potentiating effects.

In some embodiments, the compound disclosed herein is selected from the group consisting of the compounds in Table 40. The SP-BIMs shown below in Table 40 have even more favorable docking scores than those of SP-BIM 9 and SP-IM 13, suggesting these compounds may possess further improved antibiotic adjuvant properties.

Figure 19A:
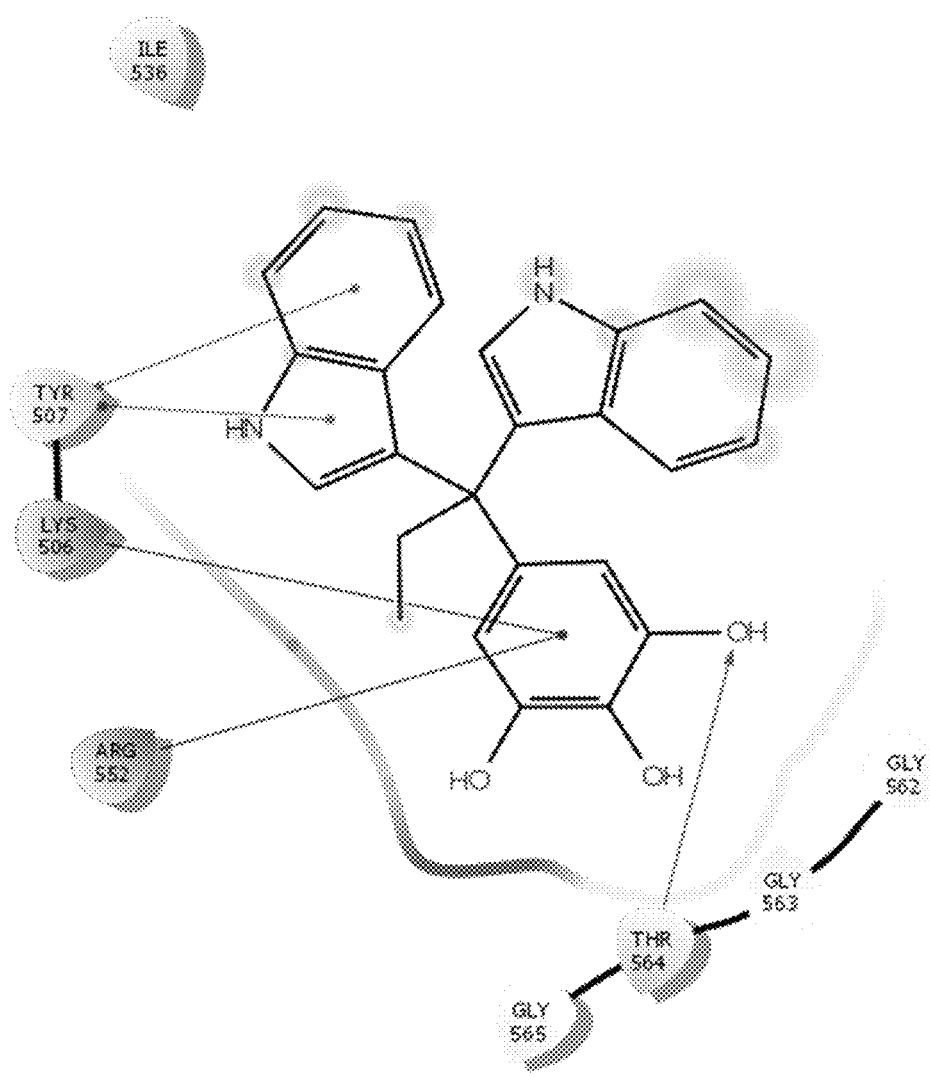
FIG. 19A shows in silico docking pose of SP-BIM 33 onto the catalytic domain of *Bacillus cereus* histidine kinase (HK) walK (PDB: 3SL2, chain A, residues 451-611), according to one or more embodiments.
Figure 19B:
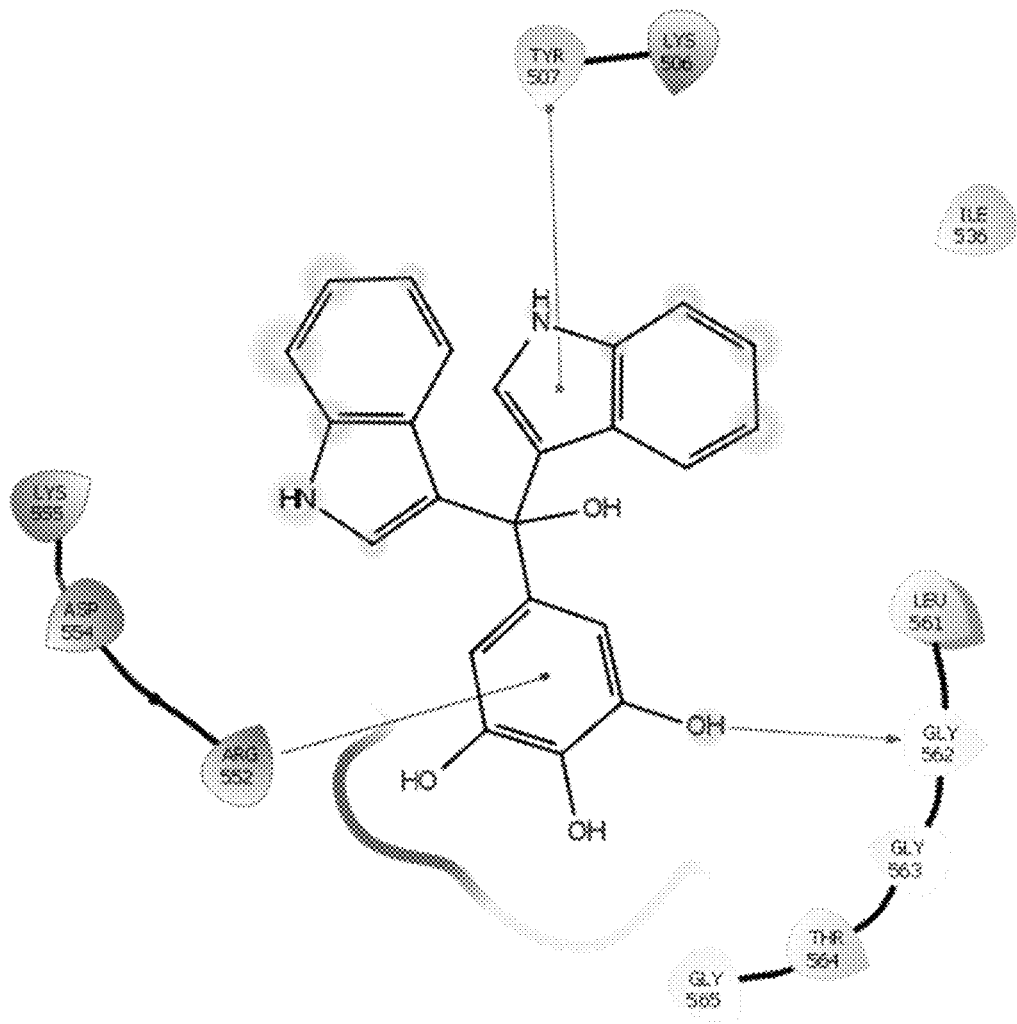
FIG. 19B shows in silico docking pose of SP-BIM 34 onto the catalytic domain of *Bacillus cereus* histidine kinase (HK) walK (PDB: 3SL2, chain A, residues 451-611), according to one or more embodiments.

FIGS. 19A-B show in silico docking poses of SP-BIMs 33 and 34, respectively.

TABLE 40

Docking scores for SP-BIMs 21-24 and 30-32.

| Structure | Name | SP-BIM Number | Docking Score |
|---|---|---|---|
| 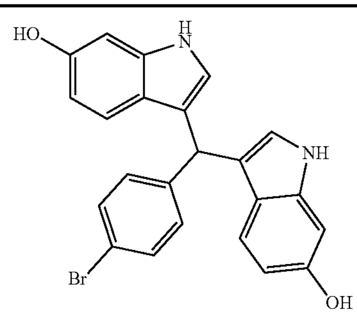 | 3,3'-((4-bromophenyl)-methylene)bis(1H-indol-6-ol) | 23 | −12.273 |
| 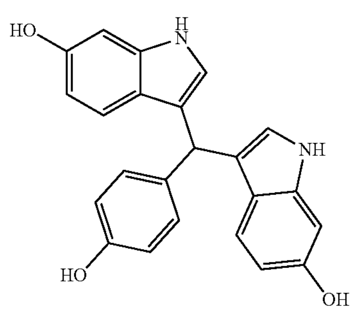 [SMILES: Oc1ccc(C(c2c[nH]c3cc(O)ccc23)c2c[nH]c3cc(O)ccc23)cc1] | 3,3'-(4-hydroxyphenyl)-methylene)bis(1H-indol-6-ol) | 30 | −8.6 |

TABLE 40-continued

Docking scores for SP-BIMs 21-24 and 30-32.

| Structure | Name | SP-BIM Number | Docking Score |
|---|---|---|---|
| 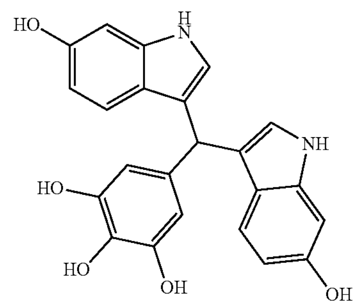 [SMILES: Oc1ccc2c(C(c3cc(O)c(O)c(O)c3)c3c[nH]c4cc(O)ccc34)c[nH]c2c1] | 5-(bis(6-hydroxy-1H-indol-3-yl)methyl)-benzene-1,2,3-triol | 22 | −8.457 |
| 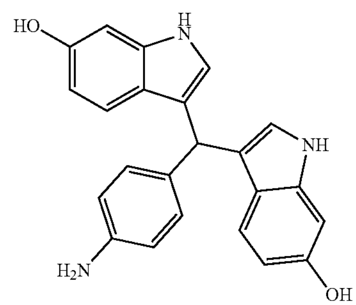 [SMILES: Nc1ccc(C(c2c[nH]c3cc(O)ccc23)c2c[nH]c3cc(O)ccc23)cc1] | 3,3'-((4-aminophenyl)-methylene)bis(1H-indol-6-ol) | 31 | −8.428 |
| 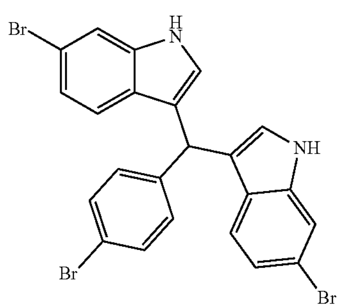 [SMILES: Brc1ccc(C(c2c[nH]c3cc(Br)ccc23)c2c[nH]c3cc(Br)ccc23)cc1] | 3,3'-((4-bromophenyl)-methylene)bis(6-bromo-1H-indole) | 21 | −8.331 |
| 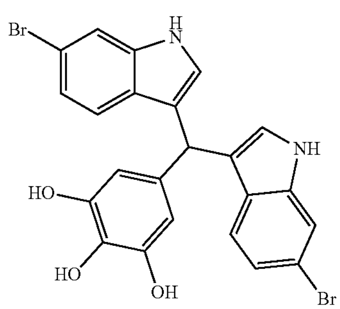 [SMILES: Oc1cc(C(c2c[nH]c3cc(Br)ccc23)c2c[nH]c3cc(Br)ccc23)cc(O)c1O] | 5-(bis(6-bromo-1H-indol-3-yl)methyl)-benzene-1,2,3-triol | 24 | −7.703 |
| 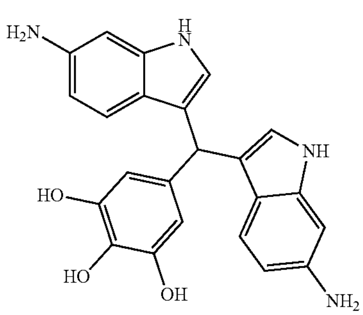 [SMILES: Nc1ccc2c(C(c3cc(O)c(O)c(O)c3)c3c[nH]c4cc(N)ccc34)c[nH]c2c1] | 5-(bis(6-amino-1H-indol-3-yl)methyl)benzene-1,2,3-triol | 32 | −7.321 |

TABLE 40-continued

Docking scores for SP-BIMs 21-24 and 30-32.

| Structure | Name | SP-BIM Number | Docking Score |
|---|---|---|---|
| (structure: benzene-1,2,3-triol with di-indolyl-propyl substituent, CH₃) | 5-(1,1-di(1H-indol-2-yl)-propyl)benzene-1,2,3-triol | 33 | −40.73 |
| (structure: benzene-1,2,3-triol with hydroxydi-indolyl-methyl substituent, OH) | 5-(hydroxydi(1H-indol-2-yl)methyl)benzene-1,2,3-triol | 34 | −47.48 |

Example 11: SP-BIM 13 Downregulates MRSA Global Regulator Genes Involved in Resistance and Pathogenicity The HK walK of Gram-positive bacteria is part of a two-component system that regulates prokaryote responses to environmental stress. The second part of this system is the corresponding cognate response regulator. In response to an environmental stimulus, the HK auto-phosphorylates a highly conserved His residue. The His residue is then transferred to an Asp residue on the response regulator molecule, altering its activity.

It has been suggested that the walk-R two component system is, at least in part, responsible for the expression of genes involved in stress responses of the bacteria (Velikova et al., *ACS Med. Chem. Lett.* 2016, 4:891-894; Zheng et al., *J Nat. Sci.* 2015, 1). The expression of the Staphylococcal accessory regulator (sarA) and accessory gene regulator (agr) was examined, which are two global regulator genes in MRSA which are involved in defense and virulence. sarA is a pleiotropic transcriptional regulator of virulence factors that can bind to the promoter regions of a subset of genes that it regulates. In contrast, agr locus plays an essential role in up-regulating exo-protein gene expression, e.g., alpha hemolysin gene (hla) and Staphylococcal enterotoxin-B (seb), while down-regulating the synthesis of cell-surface adhesins during the transition from exponential to post exponential phase (Morrison et al., *Front. Cell. Infect. Microbiol.* 2012, 2:26).

To assess the effect of SP-BIM 13 on antibiotic resistance and virulence, gene expression analysis was performed on MRSA cells exposed to a sub-lethal concentration of ampicillin. The exposure was used as a stressor on the cells to elicit a response from the bacteria. In brief, actively dividing cells were treated with ampicillin only (125 µg mL$^{-1}$), ampicillin in combination with SP-BIM 13 at 5 µg mL$^{-1}$ and 10 µg mL$^{-1}$, respectively, and SP-BIM 13 only at 5 µg mL$^{-1}$ and 10 µg mL$^{-1}$, respectively. Total RNA was extracted two hours after exposure to the compounds and converted to cDNA. Real time gene expression was monitored using the Analytik Jena Qtower and reactions were performed using SYBR® Green JumpStart™ Taq ReadyMix™ (Sigma-Aldrich). The cycling program was carried out as recommended by the manufacturer with an annealing temperature of 60° C. for 35 cycles. Result data was analyzed using the 2-ΔCT method; samples induced with 10% DMSO were used as the control. 16S rRNA gene was used as the reference housekeeping gene to normalize gene expression. cDNA synthesis was performed using the cDNA mastermix (5× All-In-One kit, Bioland) starting with 2 µg of RNA.

Figure 16A:
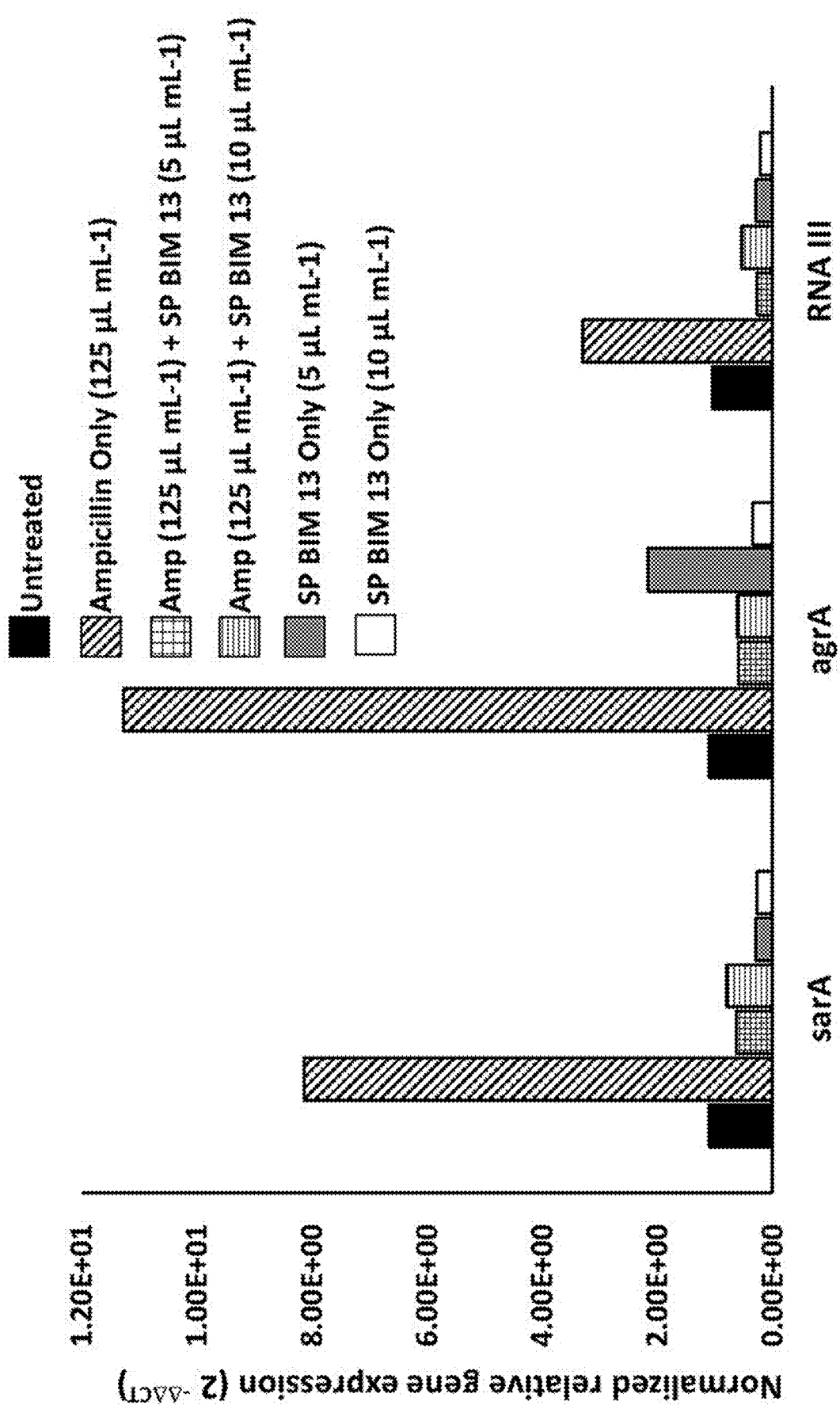
FIG. 16A depicts the efficacy of SP-BIM 13 in regulating expression of the global regulator genes Staphylococcal accessory regulator (sarA), accessory gene regulator (agr), and RNA III, according to one or more embodiments.
Figure 16B:
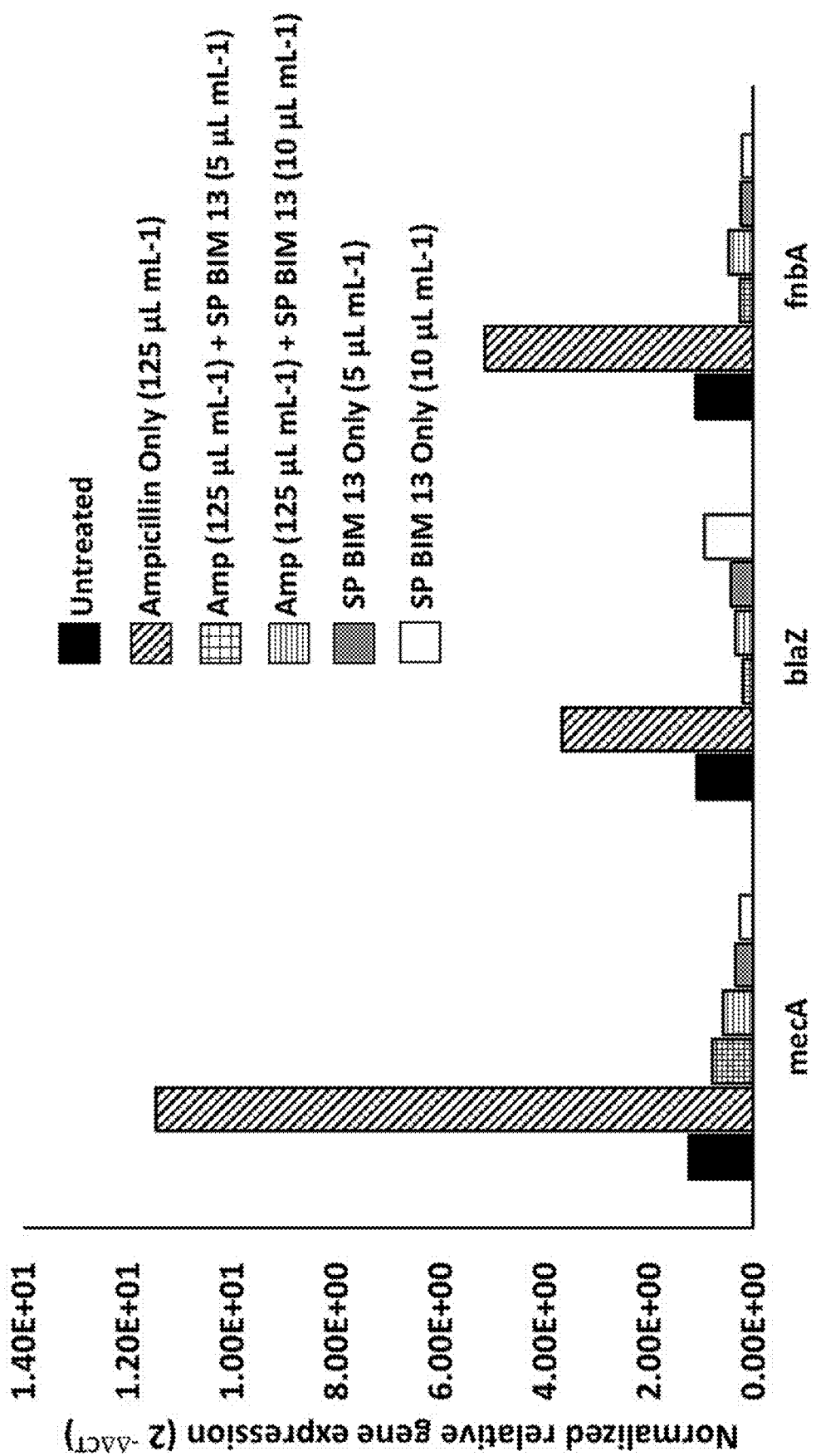
FIG. 16B depicts the efficacy of SP-BIM 13 on expression of downstream Staphylococcal genes including mecA, blaZ and fnbA, according to one or more embodiments.

The expression of the global regulators sarA, agrA and RNA III genes (FIG. 16A) were upregulated profoundly in cells exposed to ampicillin only. This could be because the bacteria recognized the antibiotic as a threat, and deployed stress response mechanisms to circumvent cell death. The expression of the mecA and blaZ genes, which are responsible for the bacteria's resistance to the antibiotic, was upregulated too (FIG. 16B). The fnbA gene (FIG. 16B) was also upregulated, indicating that exposure to the antibiotic also increased the bacterium's virulence.

Remarkably, the expression of both the downstream and regulator genes were significantly reduced when the cells were exposed to SP-BIM 13 only, or to SP-BIM 13 in combination with ampicillin. This result (FIGS. 16A and 16B) indicated that the compound was effective in controlling MRSA resistance and virulence by blocking the expression of genes responsible for these effects. This effect could be linked back to the compounds' ability to competitively inhibit the walk enzyme and prevent regulation of these genes.

Example 12: Assessment of SP-BIM Toxicity

Evaluation of Hemolysis

Hemotoxicity of the SP-BIMs were assessed following Wauford, "Hemolysis Assay", protocols.io/view/hemolysis-assay-fxkbpkw (2016). Briefly, twofold serial dilutions of each test SP-BIM were added to 2% sheep erythrocyte solution and incubated for 30 minutes at 37° C. Samples were centrifuged at 2500 g for 5 minutes and the absorbance of the supernatants measured at 541 nm. Values were represented as percent hemolysis using freeze thaw cells as 100% lysis.

Figure 17:
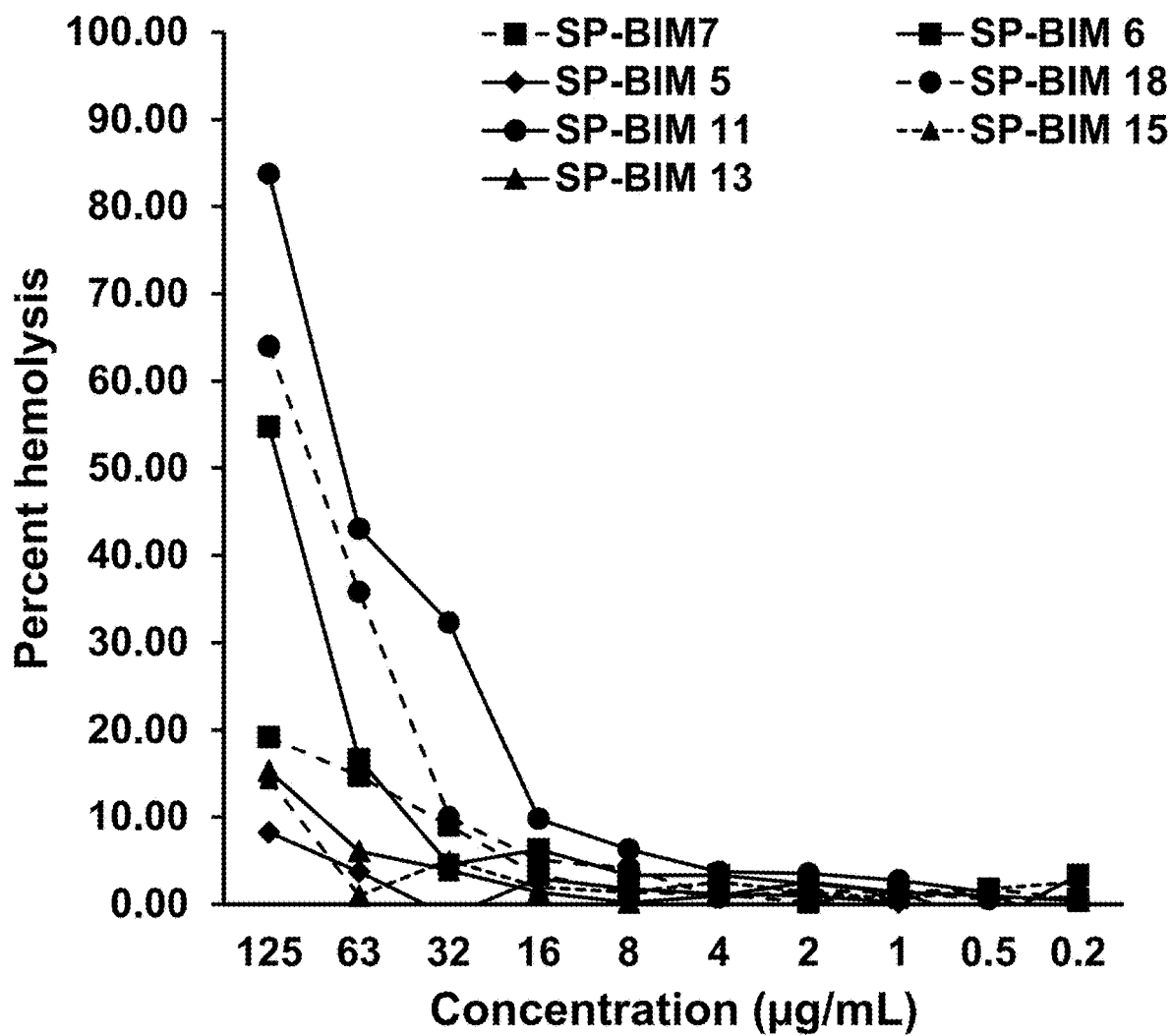
FIG. 17 depicts the hemotoxicity of SP-BIMs 5-7, 11, 13, 15, and 18, according to one or more embodiments.

Even though hemotoxicity is rare, it is a useful parameter to assess the toxicity of a potential xenobiotic. Toxicity was measured by hemoglobin release which is an indication of red blood cell (RBC) lysis. Most SP-BIMs displayed low hemotoxicity even at high concentrations. However, SP-BIMs 6, 11 and 18 proved to be very hemotoxic at concentrations between 125-16 µg mL$^{-1}$. The other SP-BIMs tested had a maximum hemolysis of only 19% and decreased as compound concentrations decreased to 0.4% (FIG. 17)

In Vitro Cytotoxicity and In Vivo Acute Toxicity of SP-BIM 13 in Mice

In vitro cytotoxicity of SP-BIM 13 was assessed using the MTT assay against with Human Umbilical Vein Endothelial Cells (HUVEC) in 96-well microtiter plates. Each well was seeded with 10,000 HUVECs and SP-BIM 13 was added to each well in a twofold serial dilution ranging from 250 µg mL$^{-1}$ to 0.1 µg mL$^{-1}$. The MTT assay involves NAD(P)H-dependent cellular oxidoreductase enzyme that converts the yellow tetrazolium MTT [3-(4,5-dimethylthiazolyl-2)-2,5-diphenyltetrazolium bromide] into insoluble (E,Z)-5-(4,5-dimethylthiazol-2-yl)-1,3-diphenylformazan (formazan). The formed formazan can be dissolved with DMSO to give a purple color with characteristic absorption at 540 nm. Intensity of purple color is directly proportional to the cell number and thus indicating the cell viability.

The concentration of SP-BIM 13 that resulted in 50% cell death was recorded as the LC$_{50}$. 750 µM was identified as the LC$_{50}$ of SP-BIM 13. This represented a relatively safe cytotoxic value.

SP-BIM 13 was further assessed for acute toxicity following guidelines from The Organization for Economic Co-Operation and Development (OECD). Mice were given one subcutaneous injection of SP-BIM 13 at two levels (i—2000 mg/kg and ii—300 mg/kg). The health and mortality of the animals was monitored daily and moribund mice were euthanized by cervical dislocation. Average mice weight and mass of food consumed per day was also measured as indicators of health. Mice injected with vehicle served as the untreated control.

Figure 18A:
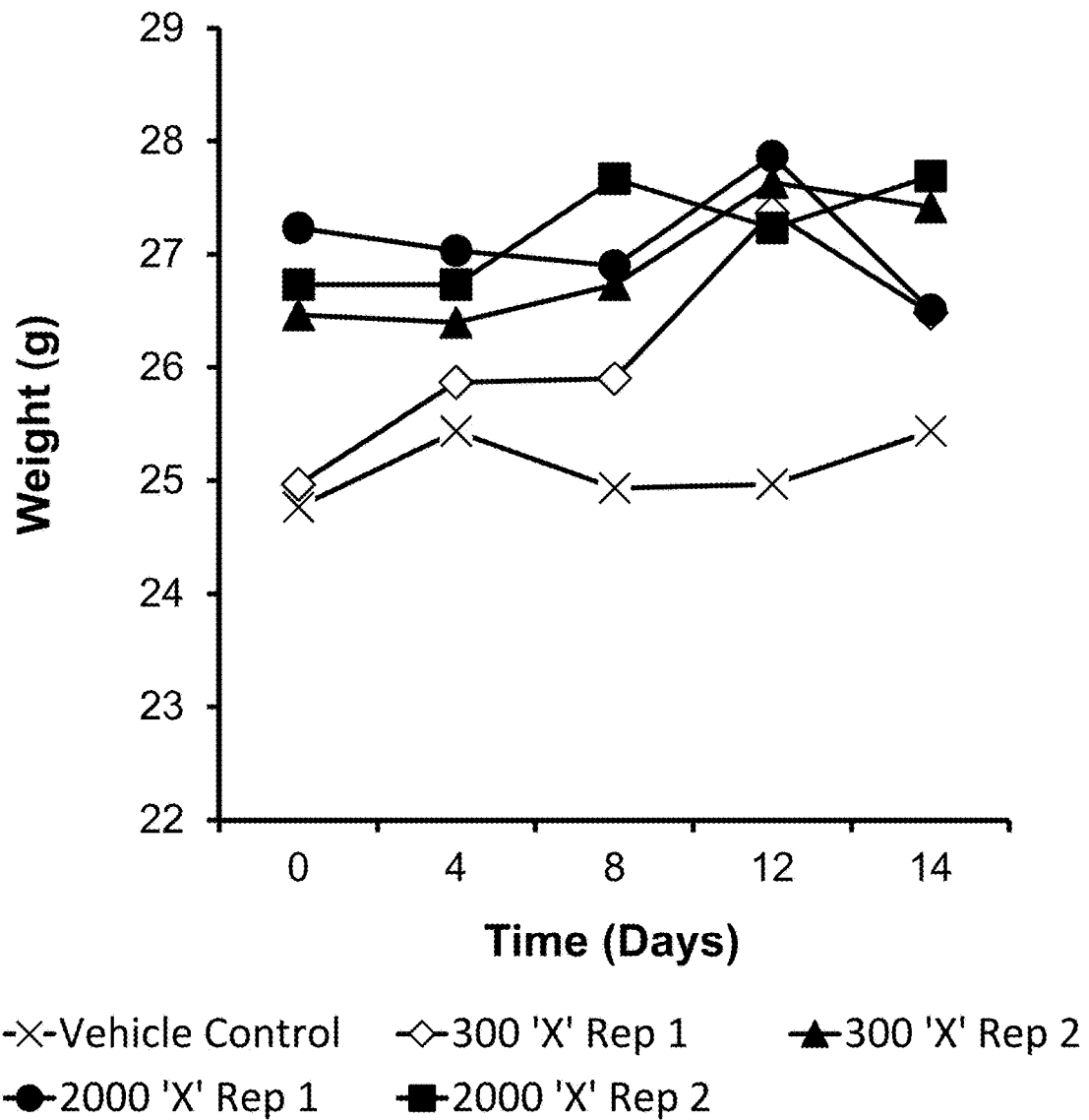
FIG. 18A depicts relative mice weights after treatment with SP-BIM 13, respectively, according to one or more embodiments.
Figure 18B:
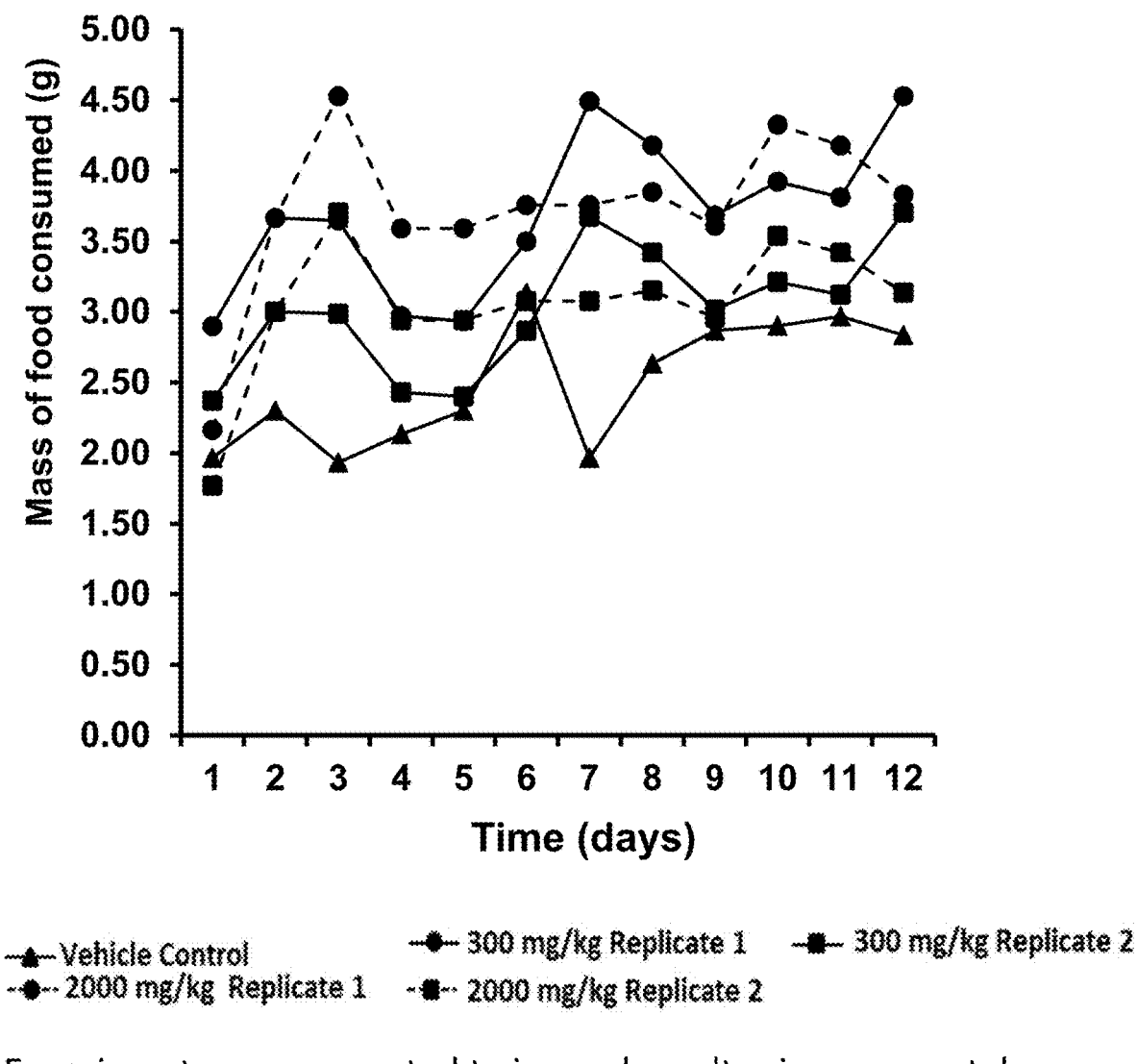
FIG. 18B depicts the mass of food consumed by mice after treatment with SP-BIM 13, respectively, according to one or more embodiments.

Mice treated with SP-BIM 13 were monitored for 14 days and FIGS. 18A and 18B demonstrate the relative mice weights and mass of food consumed after treatment with SP-BIM 13, respectively. During the observation period there was no deterioration in mice health and as a result no mice deaths were recorded. Both mice weight and appetite did not significantly vary from the untreated mice. This shows that SP-BIM 13 does not adversely affect mice.

The invention claimed is:

1. A method of treating, preventing, or reducing the risk of a microbial infection
in a patient, comprising administering to a patient a compound of:

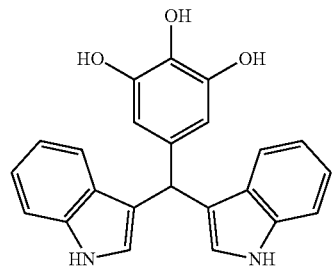 [SMILES: Oc1cc(C(c2c[nH]c3ccccc23)c2c[nH]c3ccccc23)cc(O)c1O]

or a pharmaceutical composition thereof.

2. The method of claim 1, wherein the pharmaceutical composition further comprises an antimicrobial agent.

3. The method of claim 2, wherein the activity of the antimicrobial agent is potentiated by the compound.

4. The method of claim 2, wherein the antimicrobial agent is ampicillin.

5. The method of claim 1, wherein the method further comprises treating, preventing, or reducing the risk of biofilms, hemotoxicity, and/or virulence.

6. The method of claim 1, wherein the microbial infection is a bacterial infection.

7. The method of claim 6, wherein the bacterial infection is clinically antibiotic resistant.

8. The method of claim 6, wherein the bacterial infection comprises Gram-positive bacteria, Gram-negative bacteria, or a mixture thereof.

9. The method of claim 8, wherein the bacterial infection comprises *Bacillus cereus, Streptococcus pyogenes, Streptococcus pneumoniae, Staphylococcus aureus, Enterococcus faecium, Corynebacterium diphtheriae, Escherichia coli, Salmonella typhimurium, Pseudomonas aeruginosa, Klebsiella pneumoniae, Candida albicans*, or mixtures thereof.

10. The method of claim 7, wherein the bacterial infection comprises methicillin-resistant *Staphylococcus aureus* (MRSA).

11. The method of claim 1, wherein the administration is performed once daily.

* * * * *